US012600974B2

(12) United States Patent
Bar-Even et al.

(10) Patent No.: US 12,600,974 B2
(45) Date of Patent: Apr. 14, 2026

(54) GENETICALLY ENGINEERED MICROORGANISM CAPABLE OF GROWING ON FORMATE, METHANOL, METHANE OR CO₂

(71) Applicant: MAX-PLANCK-GESELLSCHAFT ZUR FÖRDERUNG DER WISSENSCHAFTEN E.V., Munich (DE)

(72) Inventors: Arren Bar-Even; Oren Yishai, Emeryville, CA (US); Seohyoung Kim, Suwon-si (KR)

( * ) Notice: Subject to any disclaimer, the term of this patent is extended or adjusted under 35 U.S.C. 154(b) by 829 days.

(21) Appl. No.: 17/784,304

(22) PCT Filed: Dec. 10, 2020

(86) PCT No.: PCT/EP2020/085613
§ 371 (c)(1),
(2) Date: Jun. 10, 2022

(87) PCT Pub. No.: WO2021/116330
PCT Pub. Date: Jun. 17, 2021

(65) Prior Publication Data
US 2022/0348935 A1 Nov. 3, 2022

(30) Foreign Application Priority Data

Dec. 10, 2019 (EP) ..................................... 19214725

(51) Int. Cl.
| | |
|---|---|
| *C12N 15/52* | (2006.01) |
| *C12N 1/21* | (2006.01) |
| *C12N 9/00* | (2006.01) |
| *C12N 9/02* | (2006.01) |
| *C12N 9/04* | (2006.01) |
| *C12N 9/06* | (2006.01) |
| *C12N 9/10* | (2006.01) |
| *C12N 9/78* | (2006.01) |
| *C12N 9/88* | (2006.01) |
| *C12P 7/40* | (2006.01) |

(52) U.S. Cl.
CPC ........... *C12N 15/52* (2013.01); *C12N 9/0006* (2013.01); *C12N 9/0008* (2013.01); *C12N 9/0014* (2013.01); *C12N 9/0051* (2013.01); *C12N 9/1014* (2013.01); *C12N 9/78* (2013.01); *C12N 9/88* (2013.01); *C12N 9/93* (2013.01); *C12P 7/40* (2013.01); *C12Y 101/01* (2013.01); *C12Y 102/01002* (2013.01); *C12Y 104/04002* (2013.01); *C12Y 105/01005* (2013.01); *C12Y 108/01004* (2013.01); *C12Y 201/02001* (2013.01); *C12Y 201/0201* (2013.01); *C12Y 305/04009* (2013.01); *C12Y 403/01017* (2013.01); *C12Y 603/04003* (2013.01)

(58) Field of Classification Search
None
See application file for complete search history.

(56) References Cited

U.S. PATENT DOCUMENTS

2015/0218528 A1* 8/2015 Bar-Even ................. C12N 9/78
435/254.2

FOREIGN PATENT DOCUMENTS

| WO | 2014004625 A1 | 1/2014 |
|---|---|---|
| WO | 2014020599 A1 | 2/2014 |

OTHER PUBLICATIONS

Uniprot, Accession No. P24186, 2018, www.uniprot.org. (Year: 2018).*
Yishai et al., In Vivo Assimilation of One-Carbon via a Synthetic Reductive Glycine Pathway in *Escherichia coli*, ACS Synth. Biol. 7, 2018, 2023-28. (Year: 2018).*
Cotton et al., Reinforcing carbon fixation: CO2 reduction replacing and supporting carboxylation, Curr. Opinion Biotechnol. 49, 2018, 49-56. (Year: 2018).*
Liu et al., Redox cofactor engineering in industrial microorganisms, J. Indus. Microbiol. Biotechnol. 45, 2018, 313-27. (Year: 2018).*
Bassalo et al., Rapid and Efficient One-Step Metabolic Pathway Integration in *E. coli*, ACS Synthetic Biol. 5, 2016, 561-68. (Year: 2016).*
Israel A. Figueroa et al, "Metagenomics-guided analysis of microbial chemolithoautotrophic phosphite oxidation yields evidence of a seventh natural CO 2 fixation pathway", Proceedings of the National Academy of Sciences,vol. 115, No. 1, Nov. 28, 2017 (Nov. 28, 2017), p. E92-E101, DOI: 10.1073/pnas.1715549114.
Oren Yishai et al, "In Vivo Assimilation of One-Carbon via a Synthetic Reductive Glycine Pathway in *Escherichia coli*", ACS Synthetic Biology,vol. 7, No. 9, May 15, 2018 (May 15, 2018), p. 2023-2028, DOI: 10.1021/acssynbio.8b00131.
Jorge Gonzalez De La Cruz et al, "Core Catalysis of the Reductive Glycine Pathway Demonstrated in Yeast", ACS Synthetic Biology,vol. 8, No. 5, Apr. 19, 2019 (Apr. 19, 2019), p. 911-917, DOI: 10.1021/acssynbio.8b00464.

(Continued)

*Primary Examiner* — Todd M Epstein
(74) *Attorney, Agent, or Firm* — PERDUE IP LAW, APC; Donna O. Perdue

(57) ABSTRACT

The present invention relates to a genetically engineered microorganism expressing (i) formate tetrahydrofolate (THF) ligase, methenyi-THF cyclohydrolase and methylene-THF dehydrogenase, (ii) the enzymes of the glycine cleavage system (GCS), (iii) serine deaminase and serine hydroxymethyltransferase (SHMT), (iv) an enzyme increasing the availability of NADPH, and (v) optionally formate dehydrogenase (FDH), and wherein the genetically engineered microorganism has been genetically engineered to express at least one of the enzymes of (i) to (v), wheren said enzyme is not expressed by the corresponding microorganism that has been used to prepare the genetically engineered microorganism, and wherein the enzymes of (i) to (v) are genomically expressed.

Figure 1:
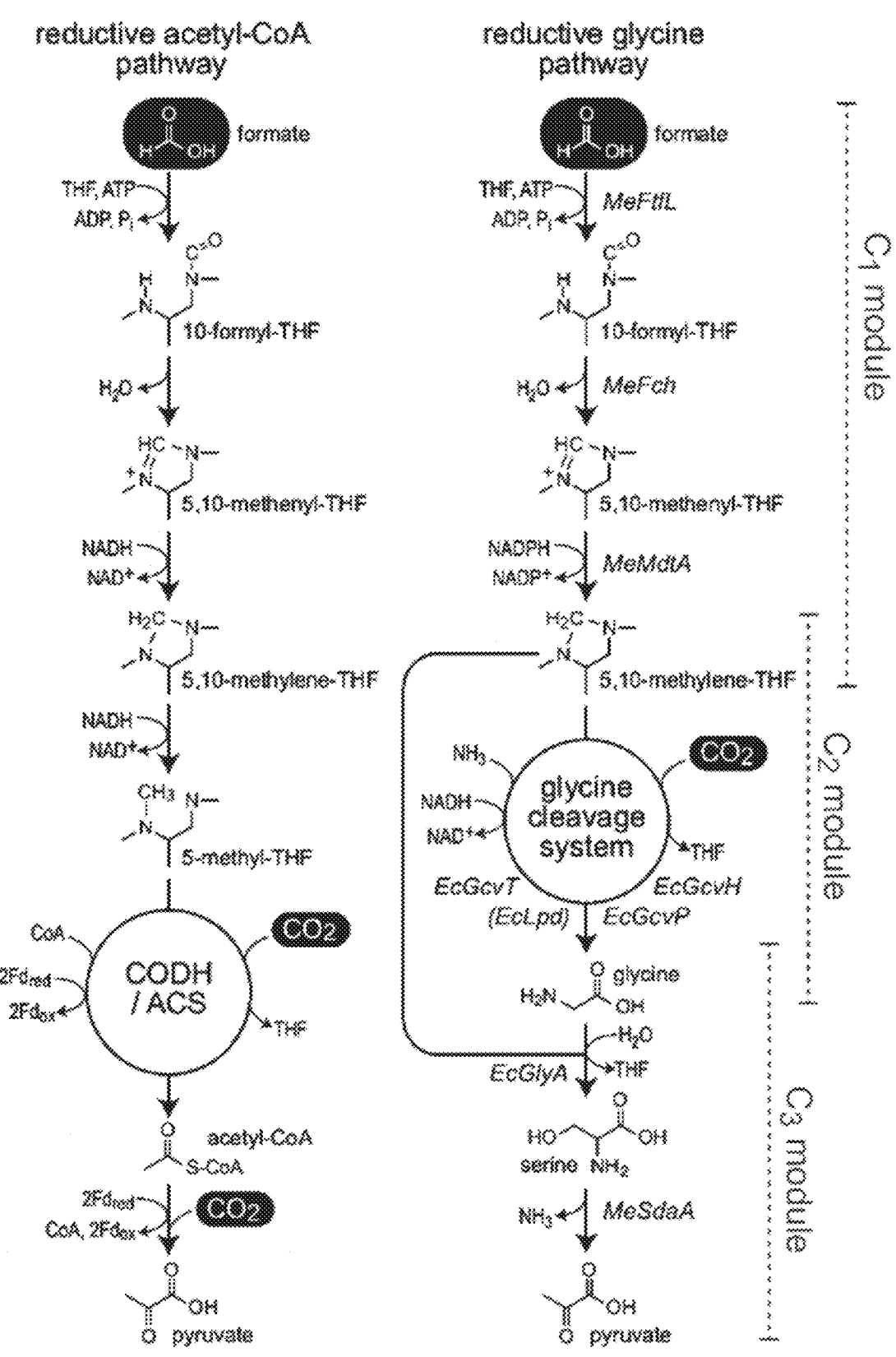

12 Claims, 15 Drawing Sheets
Specification includes a Sequence Listing.

(56)     References Cited

OTHER PUBLICATIONS

Tashiro Yohei et al, "Electrical-biological hybrid system for CO2reduction", Metabolic Engineering, Academic Press, US,vol. 47, Mar. 23, 2018 (Mar. 23, 2018), p. 211-218, DOI: 10.1016/J. YMBEN.2018.03.015.

Arren Bar-Even et al, "Design and analysis of metabolic pathways supporting formatotrophic growth for electricity-dependent cultivation of microbes", Biochimica Et Biophysica Acta (BBA)—Bioenergetics,vol. 1827, No. 8-9, Aug. 1, 2013 (Aug. 1, 2013), p. 1039-1047, DOI: 10.1016/j.bbabio.2012.10.013.

Nico J. Claassens et al. "Synthetic Methanol and Formate Assimilation via Modular Engineering and Selection Strategies", Current Issues in Molecular Biology,vol. 33, Jan. 1, 2019 (Jan. 1, 2019), p. 237-248, DOI: 10.21775/cimb.033.237.

Seohyoung Kim et al, "Growth of *E. coli* on formate and methanol via the reductive glycine pathway", Nature Chemical Biology,Feb. 10, 2020 (Feb. 10, 2020), DOI: 10.1038/s41589-020-0473-5.

* cited by examiner

Figure 4

(A) Mutation in the 5'UTR of FDH (B) Mutation in the promoter of pntAB (A) FDH                    (B) pntA (A) K4 strain (gC₁M gC₂M gC₃M gEM)

(B) K4 strain g-*FDH* g-*PntAB*

(A) K4 strain, evolved (B) K4 strain g-*FDH** g-*PntAB**

(A) $^{13}$C-formate, $^{12}$C-CO$_2$ predominantly anaplerotic flux (B) $^{12}$C-formate, $^{13}$CO$_2$ predominantly anaplerotic flux (C) $^{13}$C-formate, $^{12}$C-CO$_2$ predominantly cyclic flux via TCA cycle (D) $^{12}$C-formate, $^{13}$CO$_2$ predominantly cyclic flux via TCA cycle

GENETICALLY ENGINEERED MICROORGANISM CAPABLE OF GROWING ON FORMATE, METHANOL, METHANE OR CO2

CROSS-REFERENCE TO RELATED APPLICATIONS

This application is a national stage application under 35 U.S.C. § 371, of International Application No. PCT/EP2020/ 085613, filed Dec. 10, 2020, which claims benefit of priority to European Application No. 19214725.4, filed Dec. 10, 2019, each of which is incorporated herein by reference in its entirety.

SUBMISSION OF SEQUENCE LISTING

The sequence listing associated with this application is filed in electronic format via EFS-Web and is hereby incorporated by reference into the specification in its entirety. The text file containing the sequence listing, created on May 25, 2022, is named "SEQ_LIST_PIPL_1111_115.TXT" and is 129 KB in size.

The present invention relates to a genetically engineered microorganism expressing (i) formate tetrahydrofolate (THF) ligase, methenyl-THF cyclohydrolase and methylene-THF dehydrogenase, (ii) the enzymes of the glycine cleavage system (GCS), (iii) serine deaminase and serine hydroxymethyltransferase (SHMT), (iv) an enzyme increasing the availability of NADPH, and (v) optionally formate dehydrogenase (FDH), and wherein the genetically engineered microorganism has been genetically engineered to express at least one of the enzymes of (i) to (v), wheren said enzyme is not expressed by the corresponding microorganism that has been used to prepare the genetically engineered microorganism, and wherein the enzymes of (i) to (v) are genomically expressed.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Carbon dioxide is the focal point of many of our societal challenges and opportunities. The anthropogenic release of $CO_2$ threatens the balance of the planetary climate and could lead to a calamitous increase in global temperatures. On the other hand, $CO_2$ has the potential to replace fossil carbons as the primary feedstock for production of carbon-based value-added chemicals, including fuels, plastics, solvents, feed, and food. Yet, valorization of carbon dioxide remains an open challenge. Biological fixation of $CO_2$ by plants and algae takes place naturally on a massive scale. However, photosynthetic carbon fixation is challenging to harness due to multiple constraints, including competition for agricultural resources which erodes food security, land use which jeopardizes biodiversity, difficult processing of lignocellulosic biomass, and, most fundamentally, the low efficiency by which phototrophs use sunlight[1]. Alternatively, $CO_2$ can be upgraded by purely chemical means, e.g., generating syngas[2,3] which can be used to produce complex hydrocarbons[4]. However, such processes rely on extreme conditions and suffer from limited operational flexibility, narrow product spectrum, and low product selectivity.

An emerging solution is to integrate abiotic and biotic processes, in order to harness their respective advantages while avoiding their specific drawbacks. Physicochemical methods excel in both capturing renewable energy and using it to activate $CO_2$ into energized small molecules. Specifically, one carbon ($C_1$) compounds can be derived from $CO_2$ and renewable energy with high efficiency[5]. Biochemical processes can then convert these $C_1$ compounds into a wide array of chemicals with high specificity under ambient conditions[6]. Of the possible $C_1$ molecules, formate and methanol are especially interesting, as, unlike gases such as carbon monoxide and methane, they are miscible in water, thus avoiding mass transfer limitations. Formate can be produced by the direct electrochemical reduction of $CO_2$ with an energetic efficiency of >40%[5]. Methanol can be produced in a two-step process, where electrolysis first generates hydrogen which is then reacted with $CO_2$; the overall energetic efficiency of this process was demonstrated to be >50%[7].

While anaerobic acetogens and methanogens can consume formate or methanol at very high efficiency, their product spectrum is very limited[8]. Aerobic cultivation, while associated with lower bioconversion efficiency, is generally much more flexible in terms of production capability. Despite considerable progress in developing better genetic tools for engineering natural aerobic formatotrophs and methylotrophs, their biotechnological application is still limited. This is in part due to unfavorable cultivation parameters (e.g., cell concentration and growth rate) and low efficiency of the relevant metabolic pathways[9].

Adapting a microorganism for growth on formate or methanol has therefore been a key goal of the synthetic biology community in the last decade[10-21]. However, so far, the success of these efforts has been limited. This could be partially explained by the complexity of the natural pathways— the Calvin Cycle, the Serine Cycle, and the Ribulose Monophosphate Cycle[22]—the cyclic activity of which strongly overlaps with central metabolism and requires complex regulation of the fluxes that converge into and diverge from the pathway.

An example of a failure to generate a microorganism that can solely grow on formate is described in the article Yishai et al. (2018), ACS Synth. Biol, 7:2023-2028. Here, a genetically engineered *E. coli* was produced expressing (i) formate tetrahydrofolate (THF) ligase, methenyl-THF cyclohydrolase and methylene-THF dehydrogenase, and (ii) the enzymes of the glycine cleavage system (GCS) with the aim of generating *E. coli* which can solely grow on formate as the carbon source. However, it was found that this *E. coli* is still unable to grow on 30 nM formate and requires the addition of glucose as the main source of carbon. The essentially same results were obtained when generating genetically engineered yeast expressing the orthologous genes. Also this yeast cannot grow on formate as the sole carbon source without supplementing glycine (de la Cruz et al. (2019), ACS Synth. Biol, 8:911-9217). It has been suggested in Yishai et al. (2018), ACS Synth. Biol, 7:2023-2028 to further modify the *E. coli* to additionally express serine deaminase and formate dehydrogenase, in order to obtain an *E. coli* being capable of growing on formate as the sole carbon source. However, this has not been put into practice.

The unmet need of the provision of a genetically engineered microorganism that growths in particular under aerobic conditions on a carbon ($C_1$) compound as the sole carbon, such as formate or methanol, is therefore addressed by the present invention.

Hence, the present invention relates in a first aspect to a genetically engineered microorganism expressing (i) formate tetrahydrofolate (THF) ligase, methenyl-THF cyclohydrolase and methylene-THF dehydrogenase, (ii) the enzymes of the glycine cleavage system (GCS), (iii) serine deaminase and serine hydroxymethyltransferase (SHMT), (iv) optionally formate dehydrogenase (FDH), and (v) an enzyme increasing the availability of NADPH.

Most key biotechnological microorganisms, including *E. coli*, cannot naturally grow on $C_1$ feedstocks. As mentioned, already a number of prior art attempts to genetically engineer a microorganism to solely grow on a $C_1$ compound, in particular formate or methanol, failed.

The claimed genetically engineered microorganism of the invention is capable to efficiently grow on a $C_1$ feedstock, such as formate or methanol as the sole carbon source, in particular under aerobic conditions. This is achieved by genetically engineering a microorganism, so that it expresses the enzymes as characterized by the above items (i) to (v), noting that the expression of the enzyme of item (iv) is optional for the reasons that will be provided herein below.

The above enzymes (i) to (iv) are enzymes of the novel so-called reductive glycine pathway (rGlyP) which is illustrated in FIG. 1, right side. The rGlyP was compiled by the inventors with the aim to design and engineer a simple, linear synthetic pathway which could support a microorganism to grow on formate or methanol as sole carbon source. The rGlyP pathway was designed on the basis of the anaerobic reductive acetyl-CoA pathway (rAcCoAP)[23], which assimilates $C_1$ compounds efficiently. The reductive glycine pathway (rGlyP), as shown in FIG. 1, right side, was designed to be the aerobic twin of the unaerobic rAcCoAP[24], as shown in FIG. 1, left side. Both pathways are linear routes with limited overlap with central metabolism, minimizing the need for regulatory optimization. Both pathways start with the ligation of formate and tetrahydrofolate (THF), proceed via reduction into a $C_1$-THF intermediate, which is then condensed, within an enzyme complex, with $CO_2$ to generate a $C_2$ compound (acetyl-CoA or glycine). The $C_2$ compound is finally condensed with another $C_1$ moiety and metabolized to generate pyruvate as biomass precursor. Importantly, both the rAcCoAP and the rGlyP are characterized by a 'flat' thermodynamic profile[24,25], that is, both are mostly reversible such that the direction of the metabolic flux they carry is determined mainly by the concentrations of their substrates and products. This thermodynamic profile, while constraining the driving force of the pathway reactions[26], indicates very high energetic efficiency, where no energetic input, e.g., in the form of ATP hydrolysis, is wasted. Indeed, both pathways are associated with a very low ATP cost: only 1-2 ATP molecules are invested in the metabolism of formate to pyruvate[24]. Yet, unlike the rAcCoAP, the key enzymatic components of which are highly oxygen sensitive, the rGlyP can operate under full aerobic conditions. Due to this oxygen sensitivity of the enzymatic components of the rAcCoAP it is not feasible to use the enzymatic components of this pathway to produce genetically engineered microorganisms. It would be necessary to grow them under unaerobic conditions which is labor and cost intense for commercial large scale uses. The rGlyP overcomes this drawback of the rAcCoAP by implementing only enzymatic components that allow growth under aerobic conditions. Hence, to the best knowledge of the inventors the rGlyP represents the most efficient route—in terms of energy utilization, resources consumption, and biomass yield—to assimilate formate in the presence of oxygen[24].

A recent study suggests that the complete rGlyP might be naturally operating in a phosphite-oxidizing microbe[27]. Moreover, the key enzymatic conversion of the rGlyP, catalyzed by the glycine cleavage system (GCS), was shown to be fully reversible in many organisms[28-30]. Previous studies demonstrated that the GCS can support glycine and serine biosynthesis from formate in an engineered *E. coli* strain at elevated $CO_2$ concentration[31-33]. However, growth of the microorganism on formate (and $CO_2$) as a sole carbon source has not yet been demonstrated and remained an open challenge before the present invention was made.

As discussed above, the rGlyP comprises the four enzymatic modules corresponding to items (i) to (iv), noting that the enzymatic modules (i) to (iii) are designated C1 to C3 in FIG. 1.

According to item (i) THF ligase, methenyl-THF cyclohydrolase, and methylene-THF dehydrogenase are expressed. These enzymes act together to convert the sole $C_1$ carbon source formate into methylene-THF. In more detail, methylene-THF is generated in three steps. As will be further detailed herein below, formate is catalyzed into formyl-THF by the THF ligase, formyl-THF is catalyzed into methenyl-THF by the methenyl-THF cyclohydrolase and methenyl-THF is catalyzed into methylene-THF by the methylene-THF dehydrogenase.

According to item (ii) the enzymes of the glycine cleavage system (GCS) are expressed. These enzymes condense methylene-THF with $CO_2$ and ammonia to glycine. According to item (iii) serine hydroxymethyltransferase (SHMT) and serine deaminase are expressed. These enzymes together condense glycine with another methylene-THF to serine and finally pyruvate. The pyruvate metabolism supplies energy to microorganism when oxygen is present. Hence, once pyruvate is available, the microorganism can be maintained and grown. According to item (iv) formate dehydrogenase (FDH) is expressed. FDH generates reducing power and energy from this $C_1$ feedstock. This reducing power aids in the discussed enzymatic conversions. As will be further explained herein below, under certain conditions the reducing power and energy may also be sufficient to generate enough pyruvate in the absence of the expression of FDH. For this reason the expression of FDH is optional.

In the following further details on all individual enzymes according to items (i) to (iv) are provided.

Enzymes of Item (i):

Formate tetrahydrofolate (THF) ligase (EC 6.3.4.3) is an enzyme that catalyzes the chemical reaction ATP+formate+tetrahydrofolate $\rightleftharpoons$ ADP+phosphate+10-formyltetrahydrofolate. The chemical reaction being catalyzed by the THF ligase is reversible and in connection with the present invention the forward reaction occurs. Hence, the 3 substrates of this enzyme are ATP, formate, and tetrahydrofolate, whereas its 3 products are ADP, phosphate, and 10-formyltetrahydrofolate. This enzyme belongs to the family of ligases, specifically those forming generic carbon-nitrogen bonds. This enzyme participates in glyoxylate and dicarboxylate metabolism and one carbon pool by folate. In the examples herein below the formate tetrahydrofolate having the amino acid sequence of SEQ ID NO: 1 is used which is encoded by the nucleotide sequence of SEQ ID NO: 2. It is therefore preferred that the tetrahydrofolate used herein is at least 80% identical to the amino acid sequence of SEQ ID NO: 1 or is encoded by a nucleotide sequence being at least 80% identical to SEQ ID NO: 2.

Herein above and also herein below sequence identities of at least 80% are envisioned. For each occurrence individually the at least 80% identity is with increasing preference at least 90%, at least 95%, at least 98%, and at least 99% identity. Means and methods for determining sequence identity are known in the art. Preferably, the BLAST (Basic Local Alignment Search Tool) program is used for determining the sequence identities as referred to herein.

Methenyl-THF cyclohydrolase (EC 3.5.4.9) is an enzyme that catalyzes the chemical reaction 5,10-methenyltetrahydrofolate $+H_2O \rightleftharpoons 10$-formyltetrahydrofolate. Thus, the two substrates of this enzyme are 5,10-methenyltetrahydrofolate and $H_2O$, whereas its product is 10-formyltetrahydrofolate. The chemical reaction being catalyzed by the methenyl-THF cyclohydrolase is likewise reversible. In connection with the present invention the reverse reaction occurs. This enzyme belongs to the family of hydrolases, in particular those acting on carbon-nitrogen bonds other than peptide bonds, specifically in cyclic amidines. This enzyme participates in glyoxylate and dicarboxylate metabolism and one carbon pool by folate. In the examples herein below the methenyl-THF cyclohydrolase having the amino acid sequence of SEQ ID NO: 3 is used which is encoded by the nucleotide sequence of SEQ ID NO: 4. It is therefore preferred that the methenyl-THF cyclohydrolase used herein is at least 80% identical to the amino acid sequence of SEQ ID NO: 3 or is encoded by a nucleotide sequence being at least 80% identical to SEQ ID NO: 4.

Methylene-THF dehydrogenase (EC 1.5.1.5) is an enzyme that catalyzes the chemical reaction 5,10-methylenetetrahydrofolate+NADP$\rightleftharpoons$5,10-methenyltetrahydrofolate+NADPH+H+. The two substrates of this enzyme are therefore 5,10-methylenetetrahydrofolate and NADP+, whereas its 3 products are 5,10-methenyltetrahydrofolate, NADPH, and H+. Also the chemical reaction which is catalyzed by the methylene-THF dehydrogenase is reversible and in connection with the present invention the reverse reaction occurs. This enzyme belongs to the family of oxidoreductases, specifically those acting on the CH—NH group of donors with NAD+ or NADP+ as acceptor. In the examples herein below the methylene-THF dehydrogenase having the amino acid sequence of SEQ ID NO: 5 is used which is encoded by the nucleotide sequence of SEQ ID NO: 6. It is therefore preferred that the methylene-THF dehydrogenase used herein is at least 80% identical to the amino acid sequence of SEQ ID NO: 5 or is encoded by a nucleotide sequence being at least 80% identical to SEQ ID NO: 6.

SEQ ID NOs: 1 to 6 are sequences from the microorganism *Methylobacterium extorquens*. *Methylobacterium extorquens* (strain ATCC 14718 / DSM 1338/AM1) is a pink-pigmented facultative methylotrophs Gram-negative bacterium isolated in 1960, as an airborne contaminant growing on methylamine. It was used as a workhorse to characterize the serine cycle for assimilation of the $C_1$-unit of methylene tetrahydrofolate, a central intermediate in methylotrophic metabolism, and more recently the ethylmalonyl-CoA pathway for glyoxylate regeneration. The common trait of all Methylobacterium species is the ability to grow on one or several reduced one carbon ($C_1$) compounds other than methane, most prominently methanol. The genetically engineered microorganism of the invention is illustrated in the appended examples by a genetically engineered *E. coli*. *E. coli* does not naturally express the three enzymes THF ligase, methenyl-THF cyclohydrolase and methylene-THF dehydrogenase. It is therefore required to genetically engineer *E. coli*, so that it expresses the three enzymes.

Enzymes of Item (ii):

The enzymes of the glycine cleavage system (GCS) react the final product of the action of the THF ligase, methenyl- THF cyclohydrolase, and methylene-THF dehydrogenase 5,10-methylene-THF with $CO_2$, ammonia, and NADH to generate the C2 amino acid glycine. Finally, with the help of the enzyme of item (iii) glycine is condensed with another 5,10-methylene-THF molecule to produce the C3 amino acid serine. All reactions from formate to serine are fully reversible, and the overall thermodynamics of the pathway favor the reductive direction with $\Delta rG'm\sim$-6 kJ/mol (change in Gibbs energy at pH 7.5, ionic strength of 0.25 M and reactant concentrations of 1 mM). Hence, from a thermodynamic perspective, net production of serine is largely a matter of keeping the pathway substrates, formate and $CO_2$, at sufficiently high concentrations (Yishai et al. (2018), ACS Synth. Biol., 7, 2023-2028).

The GCS is made up of four enzymes which are called protein T, protein H, protein P, and protein L. The GCS system can be found in a wide variety of bacteria, including aerobic and unaerobic bacteria (Kikuchi et al. (2008), Proc Jpn Acad Ser B Phys Biol Sci., 84(7)). GcvT (glycine cleavage system protein T, EC 2.1.2.10) is an aminomethyltransferase. GcvH (glycine cleavage system protein H, No EC number), interacts with all other components of the GCS in a cycle of reductive methylamination (catalysed by the P-protein), methylamine transfer (catalysed by the T-protein) and electron transfer (catalysed by the L-protein, lipoamide dehdyrogenase, EC 1.8.1.4). GcvP (glycine cleavage system protein P, EC 1.4.4.2) is a glycine dehydrogenase.

While GcvTHP were overexpressed in the examples herein below it is not required to also overexpress lipoamide dehdyrogenase. This is because the wild-type exression of lipoamide dehdyrogenase (Lpd) in *E. coli* on top of the GcvTHP overexpression resulted in a slightly better growth of the *E. coli* as compared to the GcvTHP and Lpd overexpression. Without wishing to be bound by this theory this indicates that i) the natural expression level of GcvL in *E. coli* is enough to support the reductive glycine pathway, and ii) the overexpression of GcvL might slightly impair other metabolic steps in *E. coli*.

Hence, in case the microorganism to be used to produce the genetically engineered microorganism endogenously expressed the enzymes of the GCS it is preferred to overexpress the three enzymes GcvTHP but not the enzyme Lpd. In this connection it is of note that in the GCS complex the ratio of the four enzymes is 1:1:1:1, i.e. for each GcvT/GcvH/GcvP protein there should be one Lpd present. As Lpd is used for other complexes in the cell as well, it is assumed that the endogenous expression of Lpd is higher than that of GcvT/GcvH/GcvP. Based on the expression yields of the four enzymes of the GCS as described in Li et al. (2014), Cell, 157(3):624-635 in *E. coli* the expression level of Lpd is about 10-fold higher as compared to the expression of GcvT, GcvH and GcvP. Hence, in case GcvT, GcvH and GcvP are overexpressed it is preferred that GcvT, GcvH and GcvP are overexpressed at least 5-fold, more preferably at least 7.5-fold and most preferably about 10-fold. The term "about" is preferably ±20% and more preferably ±10%.

In the examples herein below GcvT, GcvH and GcvP having the amino acid sequences of SEQ ID NOs 7, 9 and 11 are used which are encoded by the nucleotide sequences of SEQ ID NOs 8, 10 and 12, respectively. It is therefore preferred that the GcvT, GcvH and GcvP used herein are at least 80% identical to the amino acid sequence of NOs 7, 9 and 11, respectively or are encoded by a nucleotide sequence being at least 80% identical to SEQ NOs 8, 10 and 12, respectively.

SEQ ID NOs: 7 to 12 are sequences from the microorganism *E. coli*. Since the genetically engineered microorganism of the invention is illustrated in the appended examples by a genetically engineered *E. coli* it is noted that *E. coli* also endogenously expresses the enzymes of the GCS. Hence, while GcvT, GcvH and GcvP can be and are preferably overexpressed in *E. coli* by genetically engineering *E. coli* also naturally occurring *E. coli* expresses GcvT, GcvH and GcvP.

The Lpd of *E. coli* has the amino acid sequences of SEQ ID NO: 59 and is encoded by the nucleotide sequences of SEQ ID NO: 60. It is therefore preferred that the Lpd as used herein is at least 80% identical to the amino acid sequence of NO: 59 or is encoded by a nucleotide sequence being at least 80% identical to SEQ NO: 60.

Enzymes of Item (iii):

Serine deaminase (or L-serine dehydratase, EC 4.3.1.17) catalyzes the reversible reaction L-serine pyruvate $\rightleftharpoons NH_3$. The reaction involves the initial elimination of water to form an enamine intermediate followed by tautomerization to an imine form and hydrolysis of the C—N bond. In the examples herein below the serine deaminase having the amino acid sequence of SEQ ID NO: 13 is used which is encoded by the nucleotide sequence of SEQ ID NO: 14. It is therefore preferred that the serine deaminase used herein is at least 80% identical to the amino acid sequence of SEQ ID NO: 13 or is encoded by a nucleotide sequence being at least 80% identical to SEQ ID NO: 14.

Serine hydroxymethyltransferase (SHMT) is a pyridoxal phosphate (PLP) (Vitamin B6) dependent enzyme (EC 2.1.2.1) which plays an important role in cellular one-carbon pathways by catalyzing the reversible, simultaneous conversions of L-serine to glycine and tetrahydrofolate (THF) to 5,10-methylenetetrahydrofolate (5,10-CH2-THF) (5,10-methylenetetrahydrofolate+glycine+$H_2O$<=>tetrahydrofolate+L-serine). In the examples herein below the serine hydroxymethyltransferase having the amino acid sequence of SEQ ID NO: 15 is used which is encoded by the nucleotide sequence of SEQ ID NO: 16. It is therefore preferred that the serine hydroxymethyltransferase used herein is at least 80% identical to the amino acid sequence of SEQ ID NO: 15 or is encoded by a nucleotide sequence being at least 80% identical to SEQ ID NO: 16.

Also SEQ ID NOs: 13 to 16 are sequences from the microorganism *E. coli*. *E. coli* endogenously expresses serine deaminase and SHMT. Serine deaminase and SHMT can be overexpressed in *E. coli* by genetically engineering *E. coli*, but also naturally occurring *E. coli* expresses serine deaminase and SHMT.

Enzyme of Item (iv):

The formate dehydrogenase (FDH, EC 1.17.1.9) which is optionally expressed is preferably expressed. FDH is an NAD-dependent formate dehydrogenase. An NAD-dependent formate dehydrogenase catalyzes the reaction formate+$NAD^+ \rightleftharpoons CO_2+NADH+H^+$. NAD-dependent formate dehydrogenases are important in methylotrophic yeast and bacteria and are vital in the catabolism of $C_1$ compounds, such as formate, methanol, methane and $CO_2$. In the examples herein below the formate dehydrogenase having the amino acid sequence of SEQ ID NO: 17 is used which is encoded by the nucleotide sequence of SEQ ID NO: 18. It is therefore preferred that the formate dehydrogenase used herein is at least 80% identical to the amino acid sequence of SEQ ID NO: 17 or is encoded by a nucleotide sequence being at least 80% identical to SEQ ID NO: 18.

SEQ ID NOs: 17 and 18 are sequences from the microorganism *Pseudomonas* sp. *Pseudomonas* is a genus of Gram-negative, Gammaproteobacteria, belonging to the family of Pseudomonadaceae. The members of the genus demonstrate metabolic diversity and consequently are able to colonize a wide range of niches. *E. coli* does not naturally express FDH, so that *E. coli* has to be genetically engineered to express this enzyme.

The expression of all the above-discussed enzymes according to items (i) to (iv) with the exception of serine hydroxymethyltransferase (SHMT) in *E. coli* is suggested in Yishai et al. (2018), ACS Synth. Biol, 7:2023-2028. It is shown in the examples herein below that a genetically engineered microorganism expressing (i) formate tetrahydrofolate (THF) ligase, methenyl-THF cyclohydrolase and methylene-THF dehydrogenase, (ii) the enzymes of the glycine cleavage system (GCS), (iii) serine deaminase and serine hydroxymethyltransferase (SHMT), and (iv) formate dehydrogenase (FDH) grows on formate as the sole carbon source. An *E. coli* expressing all these enzymes has a doubling time when grown on formate of about 70 h and a growth yield of about 1.5 gCWD/mol-formate.

Since it was desirable to further improve this performance, in particular the quite long doubling time of about 70 h, for commercial uses, but it was totally unclear which further modification is required in order to improve the performance, the inventors applied a short-term evolution approach. Thereby an *E. coli* was obtained that grows on formate with a doubling time of only about 8 h (nearly 9 times faster!) and the growth yield of about 2.3 gCWD/mol-formate is also improved. This performance is suitable for commercial uses. The *E. coli* as obtained by the short-term evolution approach was analyzed and it was found that it overexpresses (13-fold) the gene pntAB.

pntAB is an enzyme increasing the availability of NADPH. For this reason the genetically engineered microorganism of the invention comprises the fifth enzymatic module according to item (v). According to item (v) an enzyme increasing the availability of NADPH is expressed.

An enzyme increasing the availability of NADPH can be any enzyme being involved in the regeneration of NADPH. Insufficient rate of NADPH regeneration may limit the activity of biosynthetic pathways. In such cases the expression of NADPH-regenerating enzymes can be used to address this problem and increase cofactor availability (Lindner et al. (2018), ACS Synth. Biol., 7, 2742-2749). Examples of suitable NADPH-regenerating enzymes will be discussed herein below.

Hence, the microorganism of the present invention is further characterized by having an increased availability of nicotinamide adenine dinucleotide phosphate (NADPH). It was surprisingly found that the relatively slow doubling time on formate of 70 h of a microorganism expressing the enzymes of items (i) to (iv) is due to a lack of NADPH. NADPH is an essential electron donor in all organisms. It provides the reducing power that drives numerous anabolic reactions, including those responsible for the biosynthesis of all major cell components. The efficient synthesis of many of these components, however, is limited by the rate of NADPH regeneration. It is of note that NADPH is also a key factor for rGly which is consumed by methylene-THF dehydrogenase. Without wishing to be bound by this theory it may be the methylene-THF dehydrogenase of the genetically engineered microorganism of the invention which consumes the additional NADPH.

It is accordingly preferred with increasing preference that the genetically engineered microorganism has a doubling time of less than 20 h, less than 15 h, less than 10 h and about 8 h when grown on formate as the sole carbon source. The term "about" is preferably ±10% and more preferably ±5%.

As discussed herein above, Yishai et al. (2018), ACS Synth. Biol, 7:2023-2028 and de la Cruz et al. (2019), ACS Synth. Biol, 8:911-9217 obtained an *E. coli* and yeast, respectively, that can only grow on formate as carbon source if supplemented with glycine. In *E. coli* and yeast the orthologous genes were expressed to obtain these microorganisms. The essentially same results in *E. coli* and yeast as obtained in the prior art show that also the present invention is applicable to microorganism in general and not only to *E. coli* being used in the appended illustrative examples.

Taken together, the present invention provides the first genetically engineered microorganism that can efficiently solely grow on $C_1$ compounds, in particular under aerobic conditions. As is illustrated by the appended examples, this was achieved by the expression of the enzymatic modules (i) to (v) in a microorganism. Establishing synthetic formatotrophy and methylotrophy, as demonstrated herein, paves the way for sustainable bioproduction rooted in $CO_2$ and renewable energy.

In accordance with a preferred embodiment of the first aspect of the invention the enzymes of (i) to (v) are genomically expressed, preferably from genomic safe spots.

In accordance with a more preferred embodiment the first aspect of the invention relates to a genetically engineered microorganism expressing (i) formate tetrahydrofolate (THF) ligase, methenyl-THF cyclohydrolase and methylene-THF dehydrogenase, (ii) the enzymes of the glycine cleavage system (GCS), (iii) serine deaminase and serine hydroxymethyltransferase (SHMT), (iv) an enzyme increasing the availability of NADPH, and (v) optionally formate dehydrogenase (FDH), and wherein the genetically engineered microorganism has been genetically engineered to express at least one of the enzymes of (i) to (v), wheren said enzyme is not expressed by the corresponding microorganism that has been used to prepare the genetically engineered microorganism, and wherein the enzymes of (i) to (v) are genomically expressed, preferably from genomic safe spots.

In the examples herein below the genes as defined in connection with the aspect of the invention were expressed extrachromosomally from plasmids as well as intrachromosomally by introducing them into the genome of *E. coli*. While expression from plasmids and genomic expression both work, genomic expression of the enzymes is preferred since it was found to support more robust growth as compared to expression from plasmids.

Genomic safe spots are genomic loci where genes or other genetic elements can be safely inserted and expressed. Eight genomic safe spots of *E. coli* are described in Bassalo, et al. (2016), ACS 350 synthetic biology 5, 561-568, doi:10.1021/acssynbio.5b00187. These safe spots are used in the appended examples for transgene insertion and this strategy may further support robust growth. The names and map positions of the eight genomic safe spots in the *E. coli* genome are SS2:787571; SS3: 1308935; SS5:2083959; SS6: 2580897; SS7:3099988; SS8:3533732; SS9:3979535; and SS10:4411972.

In accordance with a further preferred embodiment of the first aspect of the invention the enzymes of (i) to (v) are expressed under the control of a strong constitutive promoter and/or a modified ribosome binding site.

Placing a gene under the control of strong constitutively active promoter leads to the robust overexpression of the gene. Examples of strong constitutive promoters are the PGI promoter (preferably the PGI-20 promoter as used in the appended examples) and the T7 promoter. The PGI promoters are a family of synthetic promoters derived from native promoter of glucose-6-phosphate isomerase (pgi) of *E. coli* (Braatsch et al. (2008), Biotechniques, 45(3), pp.335-337).

In bacteria, ribosome binding sites (RBSs) are effective control elements for translation initiation. By modifying an RBS the translation initiation rate can be increased. This in turn can increase protein abundance by several orders of magnitude (Salis et al., Nat Biotechnol. 2009 October ;27 (10):946-50 and Zelcbuch et al., Nucleic Acids Research, 41(9), 1 May 2013, Page e98). Hence, the modified ribosome binding site to be used in connection with the present invention increases protein abundance as compared to the corresponding wild-type RBS. The translation initiation rate of a modified RBS can be determined by the summary effect of multiple molecular interactions, including the hybridization of the 16S rRNA to the RBS sequence, the binding of tRNAfMET to the start codon, the distance between the 16S rRNA binding site and the start codon, and the presence of RNA secondary structures that occlude either the 16S rRNA binding site or the standby site. A modified RBS can be a mutated RBS or a synthetic RBS. Also, as a modified RBS, a set of RBS sequences can be used. The set comprises at least one mutated and/or synthetic RBS sequence and can also comprise native RBS sequences.

Figure 6:
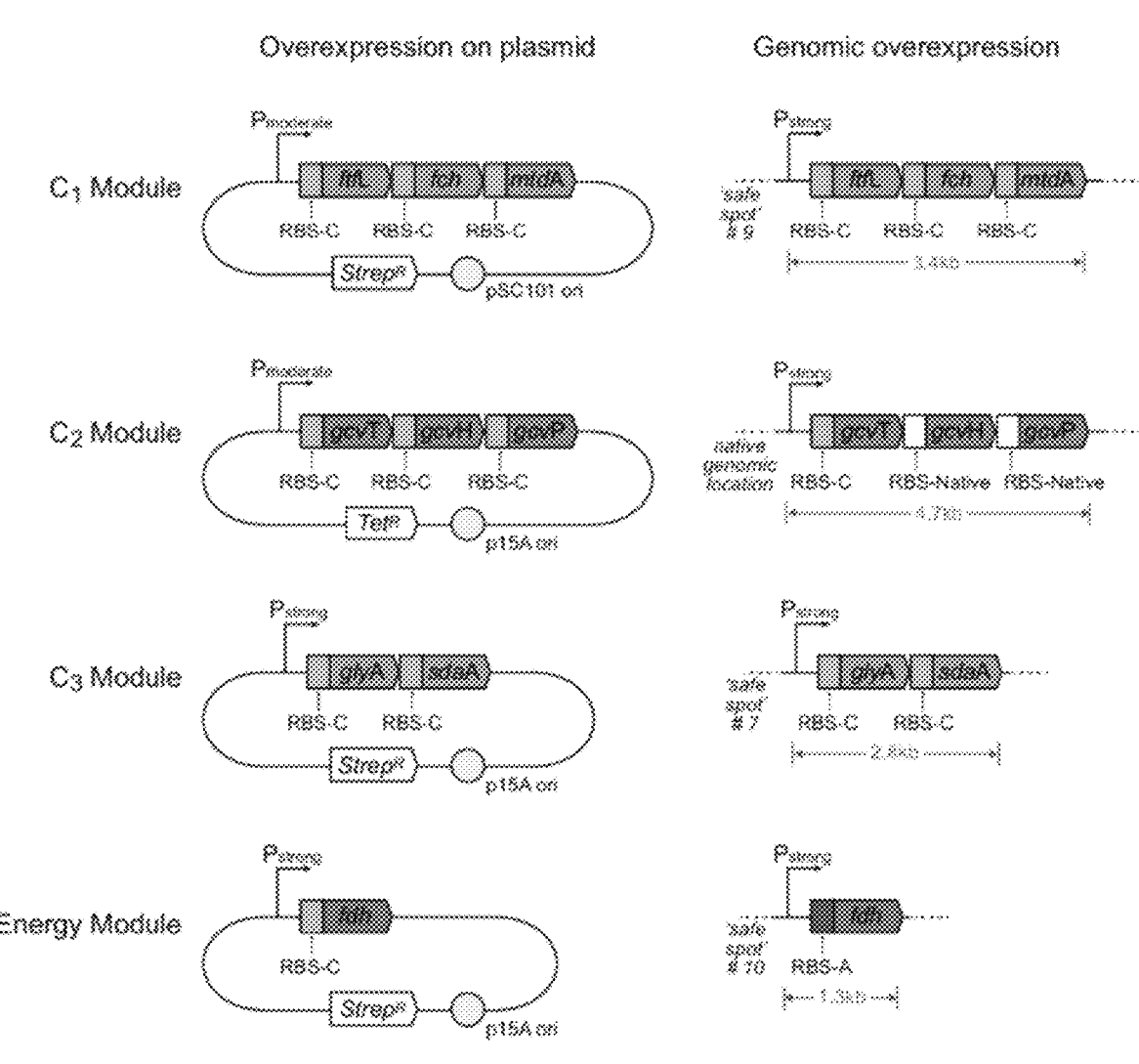

It is preferred to use one or more of the following synthetic RBS sequences: (RBS-A; SEQ ID NO: 43): AGGAGGTTTGGA, (RBS-B, SEQ ID NO: 44): AACAAAATGAGGAGGTACTGAG, (RBS-C, SEQ ID NO: 45): AAGTTAAGAGGCAAGA, (RBS-D, SEQ ID NO: 46): TTCGCAGGGGGAAG, (RBS-E, SEQ ID NO: 47): TAAGCAGGACCGGCGGCG, and (RBS-F, SEQ ID NO: 48): CACCATACACTG which are known from Zelcbuch et al., Nucleic Acids Research, 41(9), 1 May 2013, Page e98. Among this list the use of RBS-A and RBS-C is preferred (FIG. 6). For instance, a set of two or three RBS-C sequences may be used or an RBS-C sequence along with one or two native RBS sequences.

It is also possible and preferred to use a strong constitutive promoter and a modified ribosome binding site in combination as is illustrated in the examples herein below and as discussed in Wenk et al., Methods Enzymol., 608:329-367.

In accordance with another preferred embodiment of the first aspect of the invention the enzyme of (iv) is at least 2-fold, preferably at-least 3-fold, more preferably at least 4-fold and most preferably at least 5-fold higher expressed than the enzymes of (i) to (iii).

In the above discussed *E. coli* having a doubling time of only 8 h on formate a further modification was found, namely a mutation in the FDH gene which increases the expression (2.5-fold) which in turn increases the format oxidation activity 7.4-fold. Hence, the increased expression of the FDH gene is presumbaly the reason why the *E. coli* not only has a superior doubling time of only 8 h but also displays an improved growth yield of about 2.3 gCWD/mol-formate. It is assumed that not the absolute higher expression of the FDH gene is responsible but rather the higher expression as compared to the enzyme of items (i) to (iii).

In accordance with a yet further preferred embodiment of the first aspect of the invention the enzyme increasing the availability of NADPH is membrane transhydrogenase (PntAB), glucose 6-phosphate dehydrogenase (Zwf), 6-phosphogluconate dehydrogenase (Gnd), malic B enzyme (MaeB), or isocitrate dehydrogenase (Icd), and is preferably PntAB.

*E. coli* harbors five enzymes that regenerate NADPH (Lindner et al. (2018), ACS Synth. Biol., 7, 2742-2749). These five enzymes are glucose 6-phosphate dehydrogenase (Zwf, EC 1.1.1.49; SEQ ID NOs 29 and 30) and 6-phosphogluconate dehydrogenase (Gnd, EC 1.1.1.44; SEQ ID NOs 23 and 24) of the oxidative pentose phosphate pathway, a malic enzyme (MaeB, EC 1.1.1.38-40; SEQ ID NOs 27 and 28), isocitrate dehydrogenase (Icd, 1.1.1.41-42; SEQ ID NOs 25 and 26) of the TCA cycle, and a membrane-bound proton-translocating transhydrogenase (PntAB, EC 7.1.1.1; SEQ ID NOs 19 to 22). These enzymes can be found in other microorganisms, as well.

The five enzymes in *E. coli* have the amino acid sequences of SEQ ID NOs: 19, 21, 23, 25, 27, 29 and 31, respectively and are encoded by the nucleotide sequences of SEQ ID NOs: 20, 22, 24, 26, 28 and 30, respectively. It is therefore preferred that the five enzymes used herein are at least 80% identical to any of the amino acid sequences of NOs: 19, 21, 23, 25, 27, 29 and 31, respectively or are encoded by a nucleotide sequence being at least 80% identical to any one of NOs: 20, 22, 24, 26, 28 and 30. It is of note in this respect that PntAB is composed of the A unit and the B unit of SEQ ID NOs: 19 and 21 and is encoded by SEQ ID NOs: 20 and 21.

Among these five enzymes PntAB is preferred since this enzyme was found to be overexpressed in the discussed *E. coli* having a doubling time of only 8 h on formate. Since the overexpression of PntAB increases the availability of NADPH, the same effect as by PntAB can be achieved by any other enzyme increasing the availability of NADPH, as well.

In accordance with a still further preferred embodiment of the first aspect of the invention an overexpression of PntAB is achieved by introducing a mutation into the promoter region of pntAB, wherein the mutation of pntAB is preferably a single-base pair substitution in the promoter region of pntAB.

As discussed, the endogenous PntAB was found to be overexpressed in the *E. coli* having a doubling time of only 8 h on formate as shown in the appended examples. The overexpressed pntAB gene was analyzed and a single-base pair substitution in the promoter region of pntAB was found. Hence, the mutation results in a stronger promoter activity and therefore also in higher expression levels.

The nucleotide sequence of the promoter is shown in SEQ ID NO: 31. SEQ ID NO: 31 can be distinguished from the wild-type promoter by a T in nucleotide position 6 as compared to a C in the wild-type sequence. While it is not considered to be of particular relevance how the overexpression of PntAB is achieved, it is preferred that it is achieved by placing the pntAB gene under the control of a strong promoter, preferably the promoter of SEQ ID NO: 31.

PntAB was found to be overexpressed 13-fold as compared to the expression of PntAB under the control of its wild-type promoter. It is therefore preferred with increasing preference herein that PntAB is overexpressed in the genetically engineered microorganism at least 2-fold, least 3-fold, least 4-fold, least 5-fold, least 6-fold, least 7-fold, least 8-fold, least 9-fold, least 10-fold, least 11-fold, least 12-fold, and least 13-fold as compared to the expression of PntAB under the control of its wild-type promoter. This preference applies mutatis mutandis to all other enzymes increasing the availability of NADPH that can be used in place of PntAB and in particular to glucose 6-phosphate dehydrogenase (Zwf), 6-phosphogluconate dehydrogenase (Gnd), or malic B enzyme (MaeB), and isocitrate dehydrogenase (Icd).

In accordance with a preferred embodiment of the first aspect of the invention an overexpression of FDH is at least partly achieved by introducing a mutation into the 5' untranslated region of FDH, wherein the mutation of FDH is preferably a single-base pair substitution in the 5' untranslated region of FDH.

The overexpression of FDH is achieved in the examples herein below by placing the fdh gene under the control of a strong constitutive promoter and a modified ribosome binding site. As discussed above, a mutation in the FDH gene was found to further increase the expression (2.5-fold). The overexpressed fdh gene was analyzed and a single-base pair substitution was found in the 5' untranslated region (UTR) of the FDH gene. The 5'UTR with the single-base pair substitution is shown in SEQ ID NO: 32.

It is preferred that the FDH gene encoding the overexpressed FDH is characterized by the 5'UTR of SEQ ID NO: 32. SEQ ID NO: 32 can be distinguished from the wild-type 5'UTR by an A in nucleotide position 10 as compared to a C in the wild-type sequence.

In accordance with a further preferred embodiment of the first aspect of the invention the microorganism is auxotrophic for serine, glycine and $C_1$ moieties.

Auxotrophy is the inability of an organism to synthesize a particular organic compound required for its growth. Hence, this genetically engineered microorganism preferably cannot synthesize serine, glycine and $C_1$ moieties.

As discussed herein above, in the prior art Yishai et al. (2018), ACS Synth. Biol, 7:2023 a genetically engineered *E. coli* was produced which cannot solely grow on formate but only if glucosen is supplemented. Hence, in order to ensure that no serine, glycine or any $C_1$ moieties are present in the examples herein below, a microorganism being auxotrophic for serine, glycine and $C_1$ moieties was used to generate the genetically engineered microorganism of the invention. The microorganism being auxotrophic for serine, glycine and $C_1$ moieties preferably comprises the four gene deletions ΔserA Δkbl ΔltaE ΔaceA. The first deletion abolishes native serine biosynthesis, the second and third abolish threonine cleavage to glycine, and the fourth deletion prevents the formation of glyoxylate that could potentially be aminated to glycine[32]. By starting from such a microorganism it was possible to prove that the *E. coli* is capable to grow on formate as the sole carbon source. The combined activity of the enzymes of items (i) to (iii) enables the cell to metabolize formate into C1-THF, glycine, and serine, relieving these auxotrophies (FIG. 2A).

In accordance with another preferred embodiment of the first aspect of the invention the microorganism is a bacterium, preferably a proteobacterium, more preferably an enterobacterium and most preferably *E. coli.*

While the present invention is applicable to microorganisms in general, as is discussed herein above in an illustrative manner for *E. coli* and yeast, the appended examples illustrate the present invention on the basis of *E. coli. E coli* is a bacterium, more specifically a proteobacterium of the family of enterobacteria.

In accordance with a preferred embodiment of the first aspect of the invention the microorganism is capable of converting methanol to formate.

As is illustrated in the appended examples, the genetically engineered microorganism of the invention can be further genetically engineered, so that it can convert methanol to formate. Such a further genetically engineered microorganism is capable of growing on methanol as the sole carbon source.

In order to enable the genetically engineered microorganism of the invention to convert methanol to formate it is preferred to additionally express a NAD-dependent methanol dehydrogenase (EC 1.1.1.244), PQQ-dependent methanol dehydrogenase (EC 1.1.99.8), or oxygen-dependent methanol oxidase (EC 1.1.3.13). The use of a NAD-dependent methanol dehydrogenase is illustrated by the appended examples. The methanol dehydrogenase is an NAD+-dependent methanol dehydrogenase that catalyzes the chemical reaction methanol+NAD+ ⇌ formaldehyde+NADH+H+. Thus, the two substrates of this enzyme are methanol+ NAD+, whereas its 3 products are formaldehyde, NADH, and H+. This enzyme belongs to the family of oxidoreductases, specifically those acting on the CH—OH group of donor with NAD+ or NADP+ as acceptor. The systematic name of this enzyme class is methanol:NAD+ oxidoreductase.

In the examples herein below the methanol dehydrogenase having any one of the amino acid sequences of SEQ ID NOs: 33, 35, 37, 39, and 41 is used which are encoded by the nucleotide sequence of SEQ ID NOs: 34, 36, 38, 40, and 42, respectively. It is therefore preferred that the methanol dehydrogenase as used herein is at least 80% identical to any one of the amino acid sequences of SEQ ID NOs: 33, 35, 37, 39, and 41 or is encoded by a nucleotide sequence being at least 80% identical to any one of SEQ ID NOs: 34, 36, 38, 40, and 42.

SEQ ID NOs: 33/34, 35/36, 37/38, 39/40, and 41/42 are sequences from *Bacillus stearothermophilus* (strain: Unitprot: P42327), *Cupriavidus necator* (strain: Unitprot: F8GNE5), *Corynebacterium glutamicum* (strain: Unitprot: A4QHJ5), *Bacillus methanolicus* (strain: Unitprot: I3E949), and *Bacillus methanolicus* (strain: Unitprot: I3E949) with the mutations Q5L and A363L, respectively.

In a second conversion formaldehyde is reduced to formate. This is done in the exemplified *E. coli* via the endogenous glutationine system, so that once formaldehyde is formed it is reduced to format without the necessity of additional genomic engeneering (Gutheil, et al. (1997), Biochemical and biophysical research communications, 238 (3):693-696). Alternative pathways for reducing formaldehyde to formate are described in Lidstrom (2006), Volume 2: Ecophysiology and Biochemistry, pp.618-634.

It is of note that the reduction of methanol to formate is expected to result in sufficient energy (i.e. reducing power) to enable the genetically engineered microorganism to grow efficiently. Hence, in connection with the microorganism being capable of converting methanol to formate it might not be required to express FDH, thereby providing additional energy (i.e. reducing power). For this reason FDH is optionally present in the genetically engineered microorganism of the invention.

In accordance with a further preferred embodiment of the first aspect of the invention the microorganism is capable of converting methane to formate.

Similarly, the genetically engineered microorganism of the invention can be further genetically engineered, so that it can convert methane to formate. Such a further genetically engineered microorganism is capable of growing on methane as the sole carbon source.

In order to enable the genetically engineered microorganism of the invention to convert methane to formate it is preferred to additionally express methane monooxygenase (MMO). Methane monooxygenase (MMO) is an enzyme capable of oxidizing the C—H bond in methane as well as other alkanes. Methane monooxygenase belongs to the class of oxidoreductase enzymes (EC 1.14.13.25). Methane monooxygenase is the first enzyme in the metabolic pathway of methanotrophs, which are bacteria that use methane as source of carbon and energy. The MMO can be selected from the membrane-bound particulate MMO (pMMO), soluble MMO (sMMO), and the related enzyme ammonia monooxygenase (AMO).

Since, methane hydroxylation results in methanol $(CH_4+\frac{1}{2}O_2\rightarrow CH_3OH)$, the genetically engineered microorganism of the invention being capable of converting methane to formate is generally also engineered to convert methanol to formate, preferably by expressing a methanol dehydrogenase as discussed herein above.

In accordance with a still further preferred embodiment of the first aspect of the invention the microorganism is capable of converting $CO_2$ to formate.

Hence, the genetically engineered microorganism of the invention can also be further genetically engineered, so that it can convert $CO_2$ to formate. Such a further genetically engineered microorganism is capable of growing on $CO_2$ as the sole carbon source.

One option for converting $CO_2$ to formate is the electrochemical reduction of $CO_2$ to formate using formate dehydrogenase, e.g. the metal-independent enzyme type of formate dehydrogenase (FDH) derived from *Candida boidinii* yeast; see Buddhinie et al. Acc. Chem. Res. 2019, 52, 3, 676-685. In more detail, Buddhinie et al. describe the reduction of $CO_2$ to formate using electrochemically reduced methyl-viologen as an artificial electron donor. Another option for catalyzing the reduction of $CO_2$ is the use of a carbon dioxide reductase, in particular the hydrogen-dependent carbon dioxide reductase from *Acetobacterium woodii*; see Schuchmann Müller (2013), Science, 342 (6164):1382-1385. A yet further option is the use of a hydrogenase enzyme to obtain NADH and the use of a formate dehydrogenase using the produced NADH for $CO_2$ reduction.

The present invention relates in a second aspect to a method for growing the microorganism as defined in accordance with the first aspect of the invention which expresses FDH, comprising culturing the microorganism under growth conditions comprising formate as the sole carbon source.

It is of note that in accordance with this method the microorganism also has to express FDH since the activity of this enzyme is required to produce enough energy (i.e. reducing power) to enable the microorganism to grow efficiently.

Means and methods for culturing microorganisms under growth conditions are established in the art; see, for example Lodish (2000), Molecular Cell Biology, 4th edition, section 6.1, W.H. Freeman and Company. Many prokaryotes (i.e., bacteria) and single-celled eukaryotes such as yeast, all of which grow in nature as single cells, can be easily grown in culture dishes.

The present invention relates in a third aspect to a method for growing the microorganism being capable of converting methanol to formate as defined in accordance with the first aspect of the invention, comprising contacting the microorganism under growth conditions comprising methanol as the sole carbon source.

For the reasons discussed above, the microorganism being capable of converting methanol to formate might not be required to express FDH.

The present invention relates in a fourth aspect to a method for growing the microorganism being capable of converting methane to formate as defined in accordance with the first aspect of the invention which expresses FDH, comprising culturing the microorganism under growth conditions comprising methane as the sole carbon source.

In this case the microorganism has to express FDH in order to have enough energy (i.e.

reducing power) for efficient growth.

The present invention relates in a fifth aspect to a method for growing the microorganism being capable of converting $CO_2$ to formate as defined in accordance with the first aspect of the invention which expresses FDH, comprising culturing the microorganism under growth conditions with $CO_2$ as the sole carbon source.

Also in this case the microorganism has to express FDH in order to have enough energy (i.e. reducing power) for efficient growth.

Moreover, in this method generally an electron donor is required in order to reduce $CO_2$ to formate. Hence, culturing the microorganism under growth conditions with $CO_2$ as the sole carbon source is generally under conditions, wherein electrons from an electron donor reduce $CO_2$ to formate. The electron donor is preferably $H_2$ or CO.

The $CO_2$ may be provided in the form of syngas. Syngas is a fuel gas mixture consisting primarily of $H_2$, CO and $CO_2$. Hence, syngas comprises $CO_2$ as the sole carbon source as well as $H_2$ and CO as electron donors to reduce $CO_2$ to formate.

A microorganism is an organism of microscopic or ultra-microscopic size that generally cannot be seen by the naked eye. Viruses are not classified as microorganisms in accordance with the present disclosure. Examples of microorganisms include bacteria, archaea, protozoa, fungi and algae. The microorganism is preferably a bacterium or fungus and is most preferably a bacterium. The fungus is preferably yeast and is most preferably Saccharomyces cerevisiae. Preferred examples of the bacterium will be discussed herein below. The microorganism of the invention is generally capable of converting a $C_1$ feedstock (e.g. formate, methanol, methane or $CO_2$) into pyruvate, glycerate, or acetyl-CoA via the formation of glycine, in particular under aerobic conditions. This conversion provides the microorganism with the required energy to survive and grow.

The term "genetically engineered microorganism" as used herein designates a genetically engineered microorganism that has been genetically engineered to express at least one enzyme that is not expressed by a corresponding (wild-type) microorganism that has been used to prepare the genetically engineered microorganism. It follows that the genetically engineered microorganism has been prepared by technical means and does not occur in nature. In this respect it is to be understood that the term "is not expressed" preferably means that no expression of the at least one enzyme is found in a corresponding (wild-type) microorganism. However, the term "is not expressed" also comprises the situation where essentially no expression of the at least one enzyme is found in a corresponding (wild-type) microorganism.

In this respect, genetic engineering generally means the artificial manipulation, modification, or recombination of DNA or other nucleic acid molecules in order to modify an organism or population of organisms. Genetic engineering can be accomplished using multiple art-established techniques. Non-limiting examples are transformation, transfection and transduction. Transformation is the direct alteration of a genetic component of a cell by passing the genetic material through the cell membrane. The cell membrane can be made amenable for the uptake of the genetic components to be transformed into the cell, for example, by divalent cations (e.g. calcium cations) or electroporation. The process used to insert foreign DNA into a cell is usually called transfection. For instance, liposomes and polymers can be used as vectors to deliver DNA into cultured animal cells via transfection. Positively charged liposomes bind with DNA, while polymers can be designed that interact with DNA.

They form lipoplexes and polyplexes, respectively, which are then taken up by the cells. Other transfection techniques, e.g. including using electroporation and biolistics, are also known in the art.

The term "expression" (or gene expression) designates the process by which information from a gene is used in the synthesis of a functional gene product, which product is in the present case a protein. Hence, expression comprises the steps of transcription of a gene into mRNA and the translation of the mRNA into protein. Expression is preferably overexpression. Overexpression is the excessive or high expression of a gene. Overexpression can be achieved, for example, by placing the gene under the control of a stronger promoter as compared to the promoter controlling the gene in nature, by using a modified ribosomal binding site (as described above) or by increasing the gene copy number in the genome.

Figure 7:
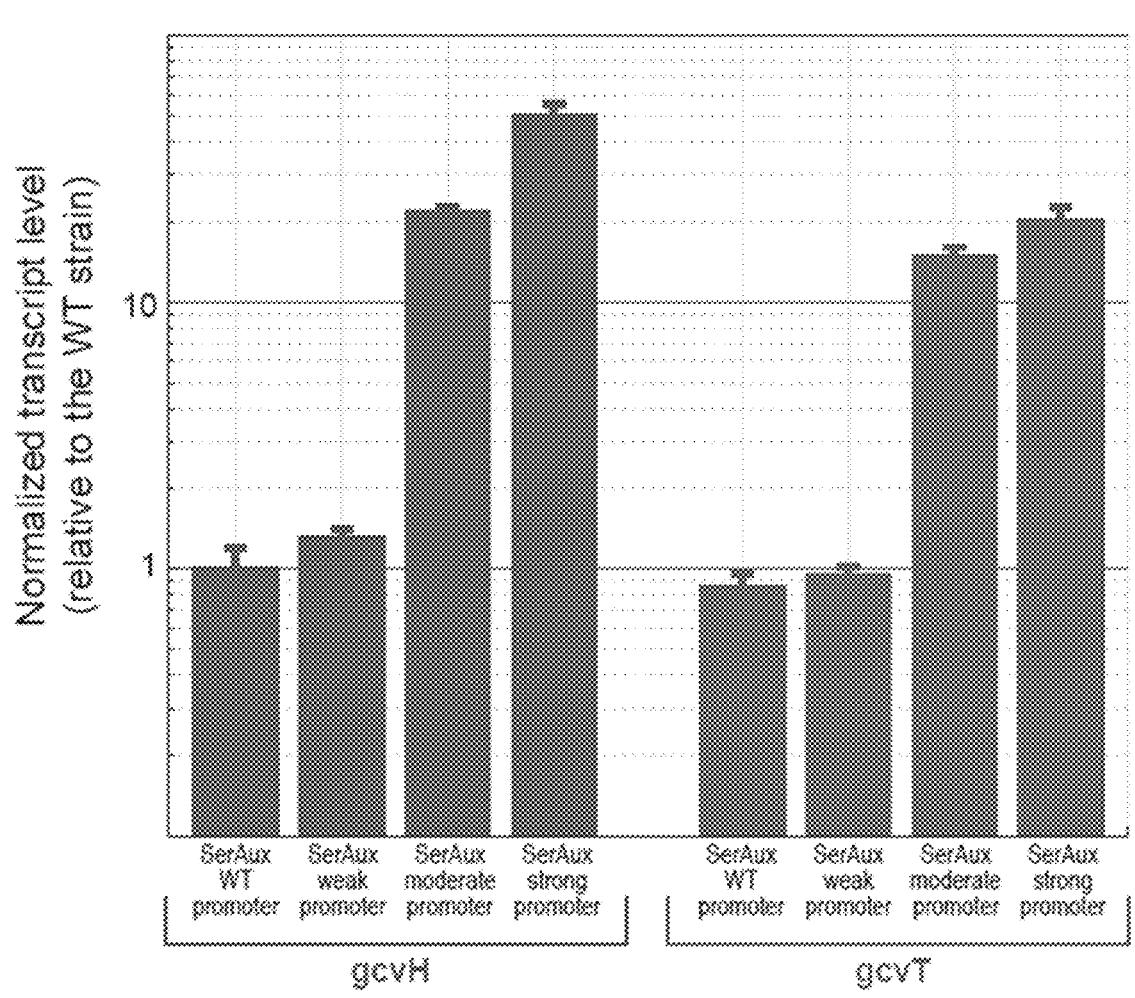

Overexpression is preferably determined in a quantitative PCR (qPRR) reaction in comparison to a constitutively expressed reference gene. Accurate interpretation of qPCR data requires normalization using constitutively expressed reference genes. Ribosomal RNA is often used as a reference gene for transcriptional studies in microorganisms, including E. coli. As an alternative a housekeeping gene can be used. Housekeeping genes are typically constitutively exprssed genes that are required for the maintenance of basic cellular function of a microorganism. Non-limiting but preferred examples of such housekeeping genes are the cysG, hcaT, idnT and rssA genes which all can be found in E. coli. In the appended examples the rssA gene is used (FIG. 7).

A gene is preferably determined to be overexpressed by qPCR if the normalized expression level of the gene as determined by qPCR in the genetically engineered microorganism of the invention is at least 2-fold, preferably at least 5-fold, more preferably at least 10-fold higher and most preferably at least 20-fold higher as compared to the normalized expression level as determined by qPCR in the corresponding wild-type microorganism. For example, the GcvT, GcvH and GcvP genes to be preferably used herein are from E. coli. In this case, the GcvT, GcvH or GcvP gene is overexpressed if the normalized expression level of the gene as determined by qPCR in the genetically engineered microorganism of the invention is at least 2-fold, preferably at least 5-fold, more preferably at least 10-fold higher and most preferably at least 20-fold higher as compared to the normalized expression level as determined by qPCR in wild-type E. coli (FIG. 7). Similarly, THF ligase, methenyl-THF cyclohydrolase and methylene-THF dehydrogenase genes to be preferably used herein are from Methylobacterium extorquens. In this case, the THF ligase, methenyl-THF cyclohydrolase or methylene-THF dehydrogenase gene is overexpressed if the normalized expression level of the gene as determined by qPCR in the genetically engineered microorganism of the invention is at least 2-fold, preferably at least 5-fold, more preferably at least 10-fold higher and most preferably at least 20-fold higher as compared to the normalized expression level as determined by qPCR in wild-type Methylobacterium extorquens.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show.

FIG. 1—The synthetic reductive glycine pathway is similar in structure to the reductive acetyl-CoA pathway. Yet, while the latter pathway is restricted to anaerobic conditions, the former can operate under aerobic conditions. Both pathways are highly ATP-efficient, as only 1-2 ATP molecules are consumed in the conversion of formate to pyruvate (e.g., instead of 7 by the Calvin Cycle). Molecular structure in brown corresponds to a sub-structure of tetrahydrofolate. Enzymes of the reductive glycine pathway, as implemented in this study, are indicated in purple (Lpd, unlike the other enzymes of the glycine cleavage system, was not overexpressed). 'Me' corresponds to *Methylobacterium extorquens* and 'Ec' corresponds to *Escherichia coli*. Division of the pathway into modules, as explained in the text, is shown in light brown to the right of the figure.

Figure 2:
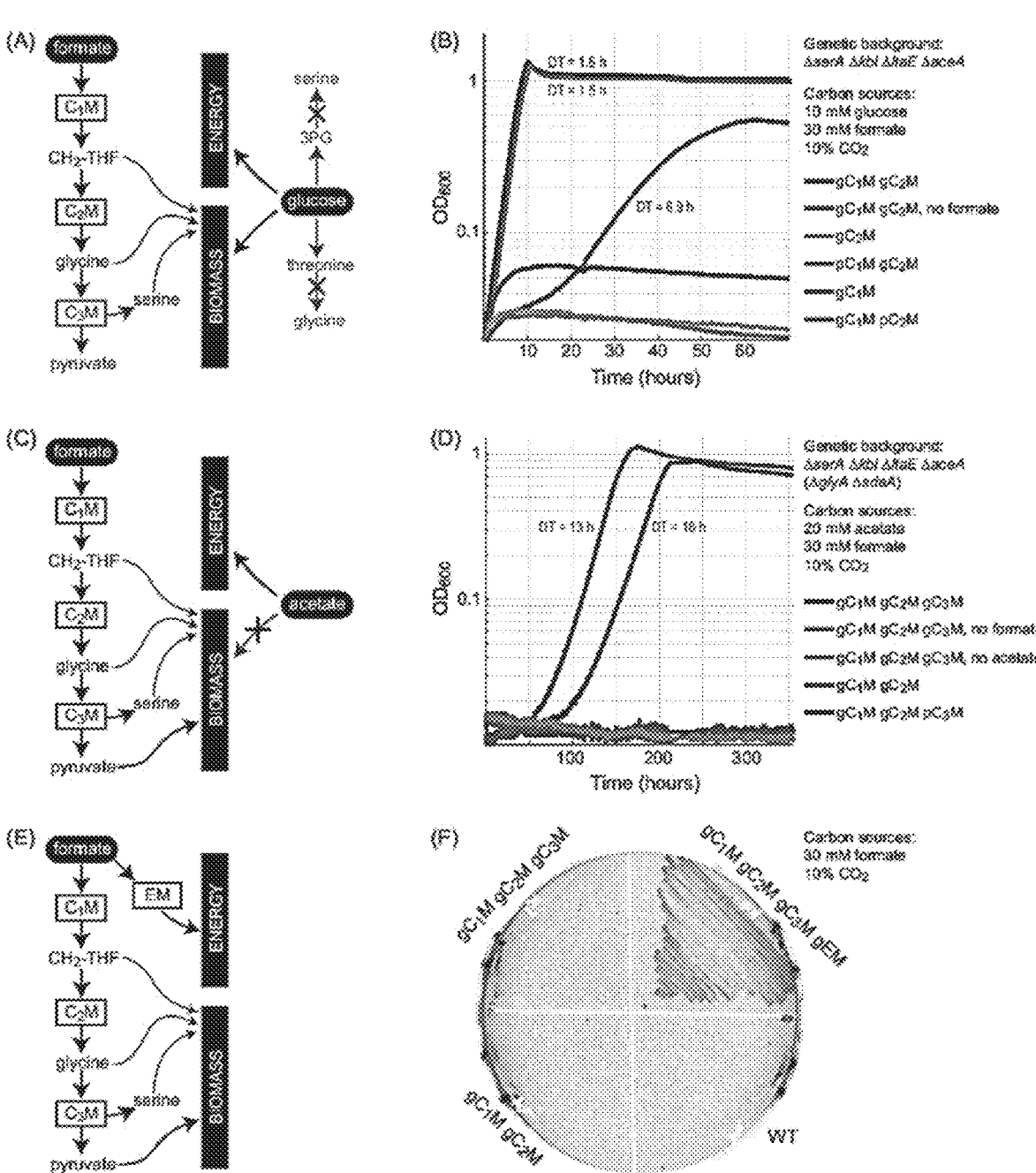

FIG. 2—Modular establishment of the reductive glycine pathway. (A) Selection scheme of $C_1M$ and $C_2M$ for the biosynthesis of $C_1$-moieties, glycine, and serine. (B) Overexpression of $C_1M$ and $C_2M$ enabled growth with formate (and $CO_2$) as sole source of $C_1$-moieties, glycine, and serine. (C) Selection scheme of $C_1M$, $C_2M$, and $C_3M$ to generate biomass building blocks, where acetate oxidation provides reducing power and energy. Deletion of aceA prevents acetate from being used as a carbon source. (D) Overexpression of $C_1M$, $C_2M$, and $C_3M$ enabled growth with formate as source of biomass and acetate as an energy source. Genomic integration of $C_3M$ was performed in strain in which the endogenous glyA and sdaA were deleted. (E) Selection scheme of $C_1M$, $C_2M$, $C_3M$, and EM to use formate as sole carbon and energy source. (F) Growth on formate is demonstrated only when all four modules are overexpressed. Genomic overexpression is indicated by 'g', while overexpression from a plasmid is indicated by 'p'. Experiments were conducted at 10% $CO_2$ within 96-well plates and were performed in triplicate, which displayed identical growth curves (±5%), and hence were averaged. Doubling times (DT) shown in the figure.

Figure 3:
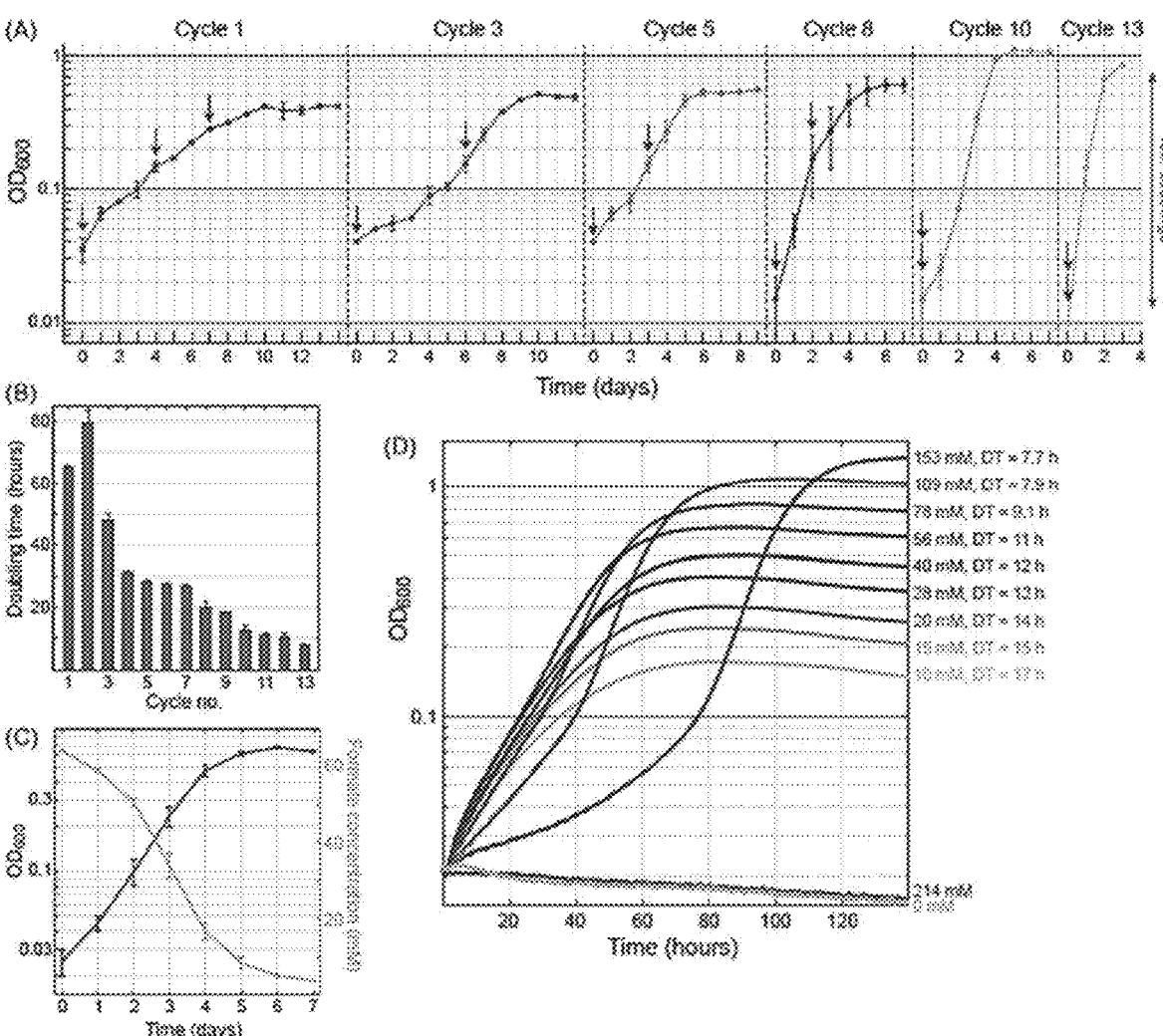

FIG. 3—Short term evolution improves growth on formate. (A) Test-tube cultivation on formate as sole carbon source. The vertical small red arrows correspond to the addition of formate, increasing the concentration in the medium by 30 mM. Upon reaching an $OD_{600}$ of 0.4, cells were reinoculated into a new test-tube with an initial $OD_{600}$ of 0.03-0.05. Error bars correspond to standard deviation of 2 experiments. 6 exemplifying cycles of cultivation are shown. (B) Doubling time decreased with cultivation cycle. Error bars correspond to standard deviation of 2 experiments. (C) Growth of the evolved strain (in test-tube) is directly coupled to a decrease in formate concentration. Error bars correspond to standard deviation of 2 experiments. (D) Cultivation of the evolved strain on formate as a sole carbon source within a 96-well plate. Experiments were conducted at 10% $CO_2$. Plate reader experiments were performed in triplicate, which displayed identical growth curves (±5%), and hence were averaged. Doubling times (DT) are shown in the figure. DT were considerably shorter in the plate reader than in test-tube as the measurements in were more accurate (taken every 10 minutes rather than once per day) and since the conditions are different (e.g., more stable cultivation environment in the plate reader).

Figure 4:
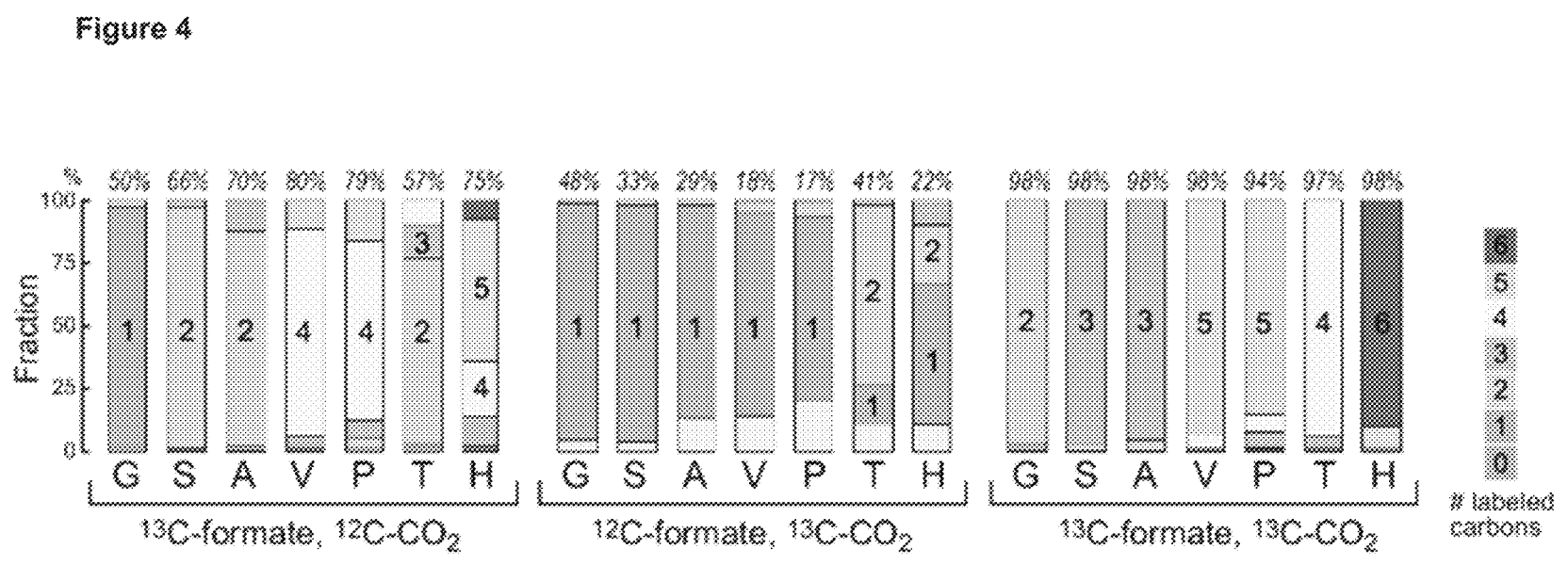

FIG. 4—Labeling pattern of proteinogenic amino acids confirms the activity of the reductive glycine pathway. As elaborated in FIG. 13, the labeling pattern is consistent with the assimilation of formate and $CO_2$ via the synthetic pathway, and indicates low cyclic flux via the TCA cycle. Numbers written in italics above the bars correspond to the overall fraction of labeled carbons.

Figure 5:
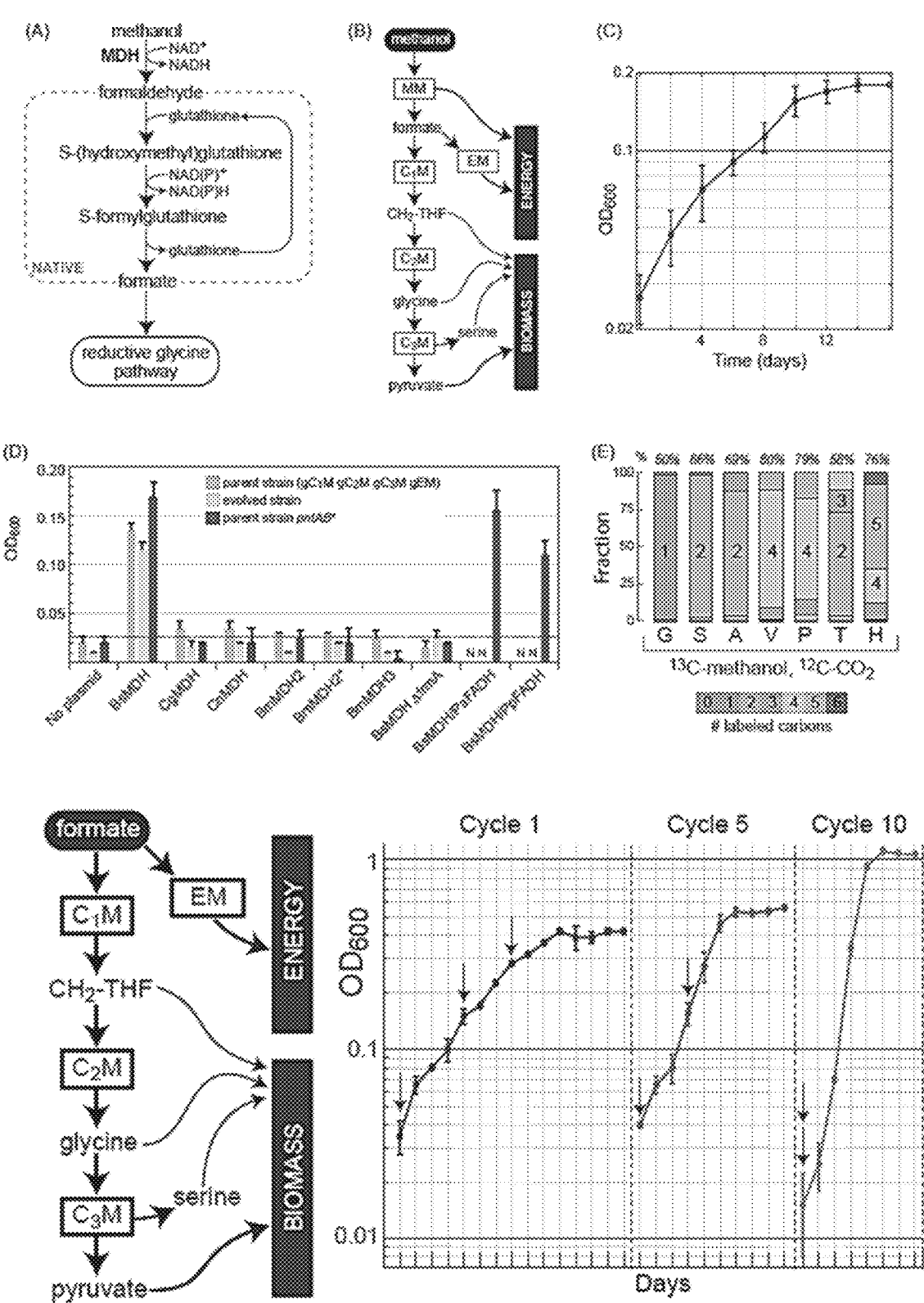

FIG. 5—Engineered growth on methanol. (A) Methanol can be assimilated via the activity of methanol dehydrogenase (MDH), where formaldehyde is oxidized to formate via the native activity of the glutathione system. (B) The Methanol Module (MM) converts methanol to formate and provides the cell with reducing power and energy. (C) Overexpression of MDH from *Bacillus stearothermophilus* (BsMDH) within the $gC_1M$ $gC_2M$ $gC_3M$ gEM strain, carrying a mutation in the promoter of the pntAB operon (FIG. 12), enabled growth on methanol within a 96-well plate. Experiments were conducted at 10% $CO_2$. Plate reader experiments were performed in triplicate, which displayed identical growth curves (±5%), and hence were averaged. (D) Comparison of growth on methanol (shown are final cell densities) with different expressed enzymes and at different genetic backgrounds. NAD-dependent MDH from several organisms was tested: *Bacillus stearothermophilus* (BsMDH), *Corynebacterium glutamicum* (CgMDH), and *Cupriavidus necator* N-1 (CnMDH), as well as two MDHs from *B. methanolicus* (BmMDH2 and BmMDH3) and an improved variant (BmMDH2*, carrying Q5L A363L modifications). Formaldehyde dehydrogenases from *Pseudomonas putida* (PpFADH; SEQ ID NOs: 49 and 50) and *Pseudomonas aeruginosa* (PaFADH; SEQ ID NOs: 51 and 52) was further tested. (E) Labeling pattern of proteinogenic amino acids upon feeding with $^{13}C$-methanol/$^{12}$-$CO_2$ is identical that with $^{13}C$-formate/$^{12}$-$CO_2$ (FIG. 4), confirming the activity of the reductive glycine pathway. Numbers written in italics above the bars correspond to the overall fraction of labeled carbons.

FIG. 6—Schematic overview of overexpression strategy. Gene overexpression from plasmid is shown in the left column while genomic overexpression is shown in the right column.

Promoter and ribosome binding sites are as described in a previous manuscript*. Genomic 'safe spots' were described previously**. (* S. Wenk, O. Yishai, S. N. Lindner, A. Bar-Even, An engineering approach for rewiring microbial metabolism. Methods Enzymol 608, 329-367 (2018); ** M. C. Bassalo et al., Rapid and efficient one-step metabolic pathway integration in *E. coli*, *ACS synthetic biology* 5, 561-568 (2016))

FIG. 7—Replacement of the native promoter of the GCV operon with a strong constitutive promoter increases gene expression 20-50 fold in a serine auxotroph (SerAux) strain (ΔserA Δkbl ΔltaE ΔaceA). Transcript levels were normalized to the expression of the rrsA gene and are shown relative to the expression of a WT (non-serine auxotroph) strain. As a comparison, the transcript levels induced by a weak constitutive promoter and moderate constitutive promoter are shown*. Experiments were performed in triplicate. (* S. Wenk, O. Yishai, S. N.

Lindner, A. Bar-Even, An engineering approach for rewiring microbial metabolism. Methods Enzymol 608, 329-367 (2018))

Figure 8:
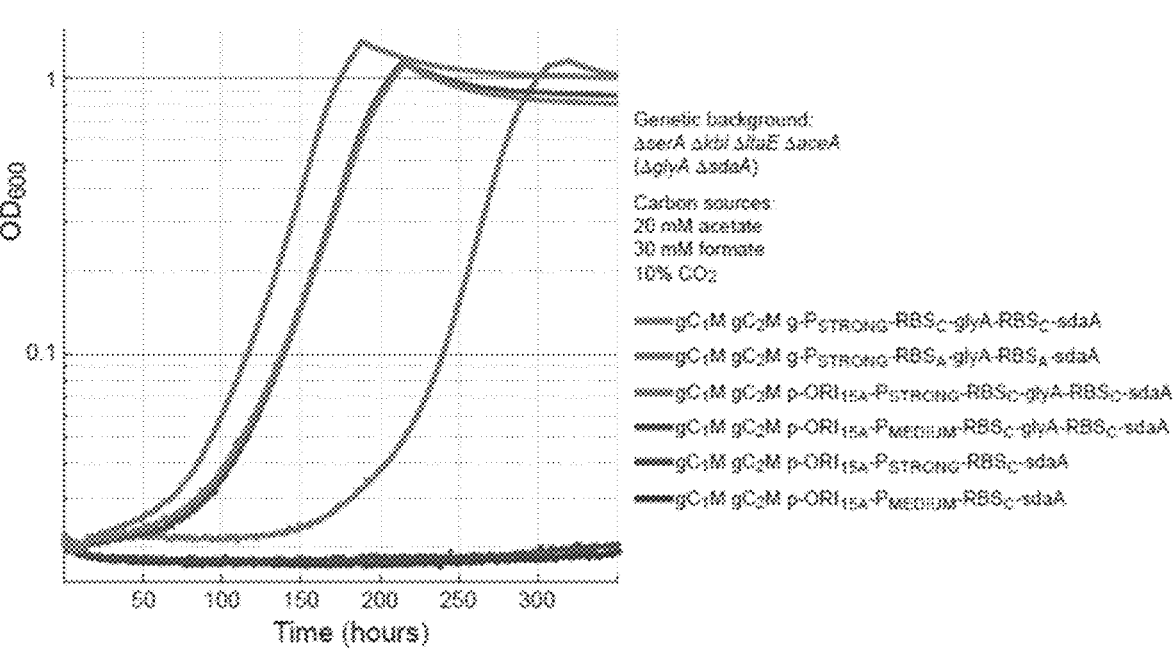

FIG. 8—Different expression approaches of the genes of C3M -glyA and sdaA—affect growth via the reductive glycine pathway, with acetate serving as an energy source. Expression on a plasmid resulted in an identical growth regardless of the promoter strength (green and blue lines). Overexpression of sdaA alone failed to achieve growth (pink and purple lines). Genomic expression (after deletion of endogenous glyA and sdaA) resulted in better growth when gene expression was controlled by a medium strength ribosome binding site ('C', pale blue line) than by a strong ribosome binding site ('A', brown line). 'g' corresponds to genomic expression and 'p' to expression on a plasmid. Origin and replication, promoters, and ribosome binding sites are described in a previous study*. (* S. Wenk, O. Yishai, S. N. Lindner, A. Bar-Even, An engineering approach for rewiring microbial metabolism. Methods Enzymol 608, 329-367 (2018))

Figure 9:
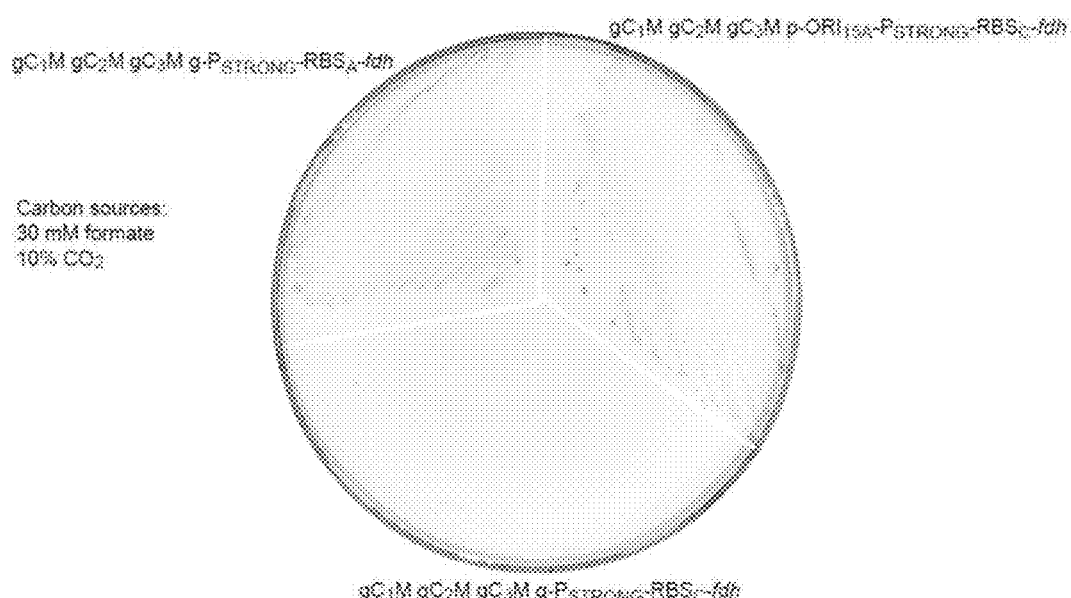

FIG. 9—Different expression approaches of the genes of EM—formate dehydrogenase—affect growth via the reductive glycine pathway. Expression on a plasmid supported growth. Genomic overexpression supported growth only when the ribosome binding site was of the highest strength ('A'). 'g' corresponds to genomic expression and 'p' to expression on a plasmid. Origin and replication, promoters, and ribosome binding sites are described in a previous study.* (* S. Wenk, O. Yishai, S. N. Lindner, A. Bar-Even, An engineering approach for rewiring microbial metabolism. Methods Enzymol 608, 329-367 (2018))

Figure 10:
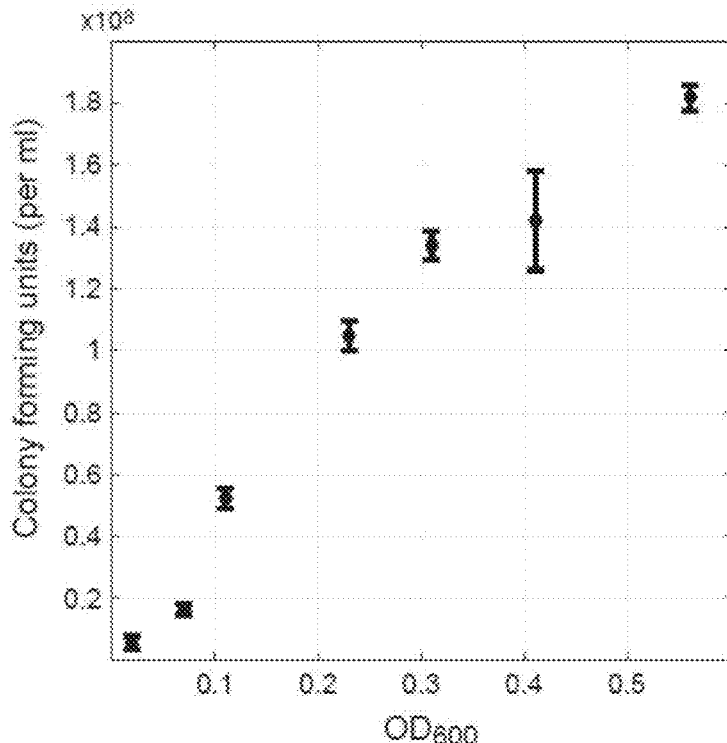

FIG. 10—Number of colony forming units increases monotonically with OD600 for cells growing on formate as sole carbon source.

Figure 11:
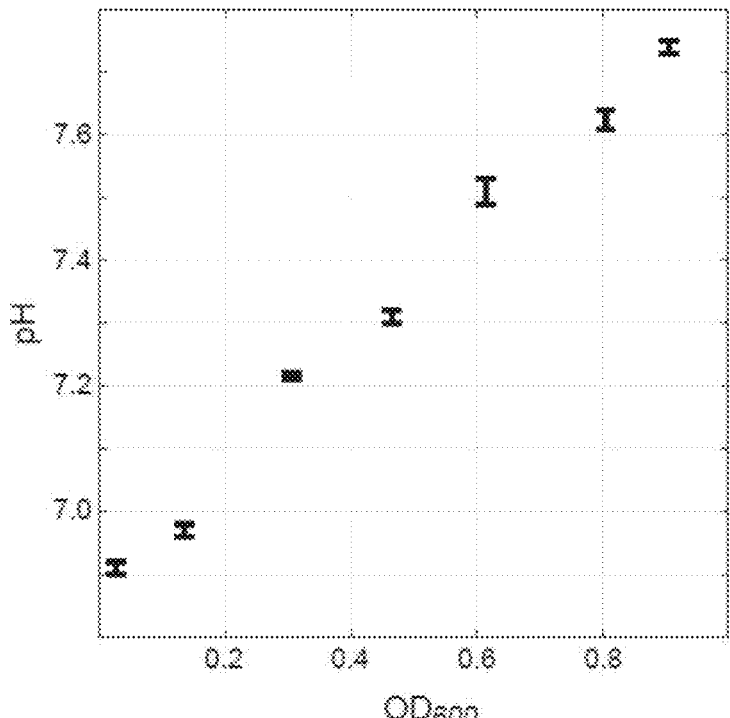

FIG. 11—Cell growth on formate directly correlates with increased medium pH due to the accumulation of $OH^-$.

Figure 12:
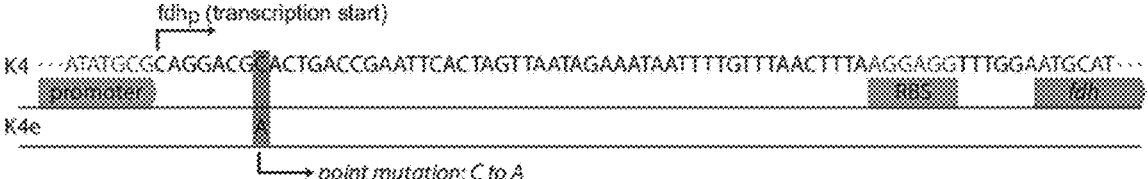
Figure 12:
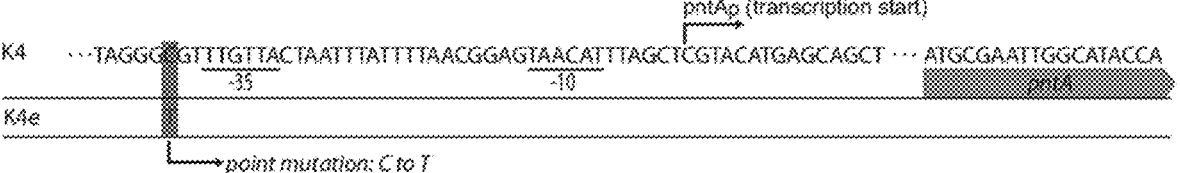

FIG. 12—Two mutations emerged within the formatotrophic strain after a short period of evolution. (A) A point mutation in the 5'-UTR of the FDH gene. (B) A point mutation in the promoter of the pntAB gene. Strain K4 corresponds to a strain in which the four modules of the reductive glycine pathway were introduced into its genome, that is, gC1M gC2M gC3M gEM, while strain K4e the same strain after short term evolution.

Figure 13:
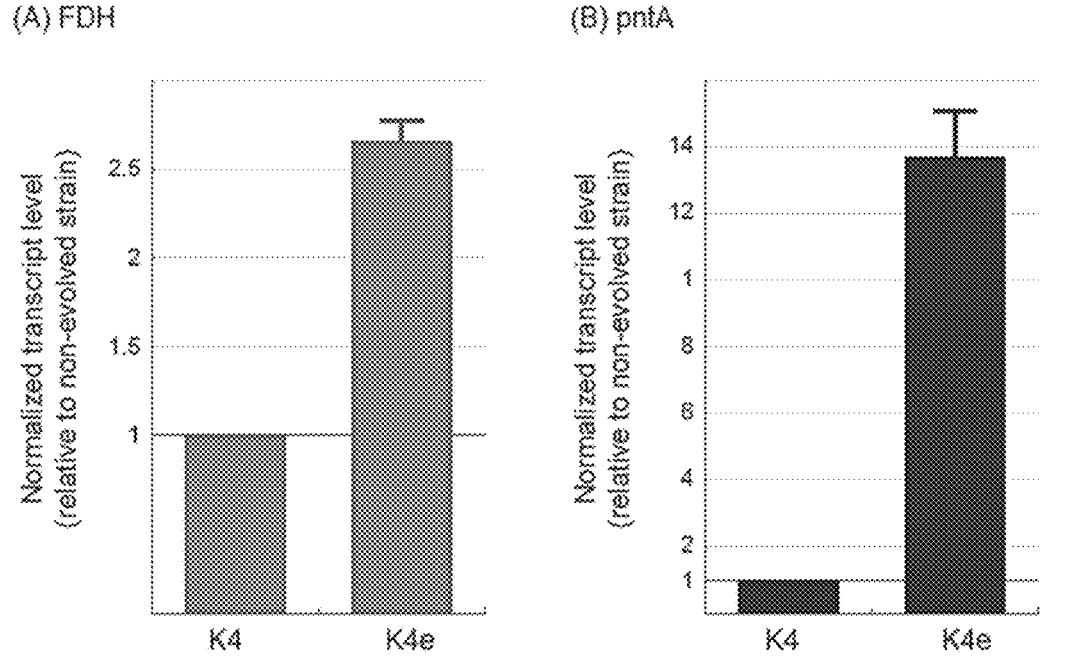

FIG. 13—Change in transcript level in the evolved strain. (A) Levels of FDH transcript increased 2.7-fold in the evolved strain. (B) Levels of pntAB transcript increased by ~14-fold in the evolved strain. In both cases transcript levels were normalized to the rrsA gene and are shown relative to the expression within a nonevolved strain. Experiments were performed in triplicate. Strain K4 corresponds to a strain in which the four modules of the reductive glycine pathway were introduced into its genome, that is, gC1M gC2M gC3M gEM, while strain K4e the same strain after short term evolution.

Figure 14:
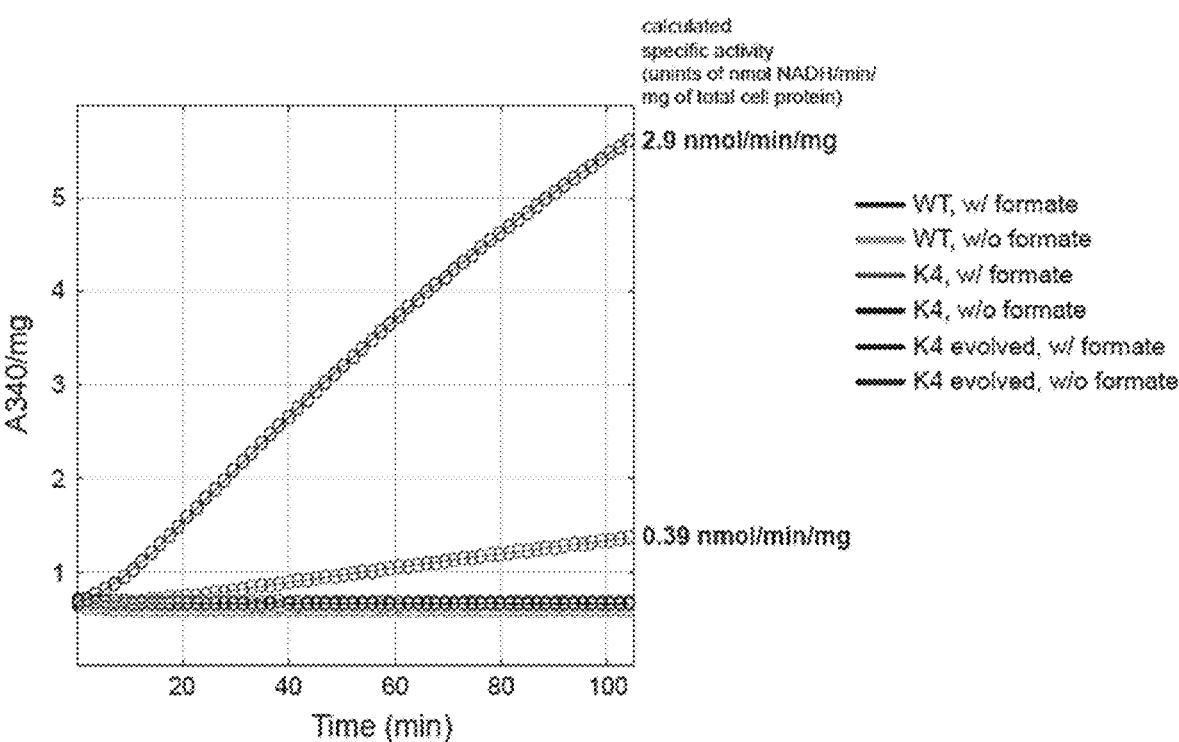

FIG. 14—Evolved strain displays 7.4-fold higher activity of FDH in cell extract. FDH activity was measured in 96-well plate by the addition of formate and NAD+ and was followed by increase in absorbance at 340 nm by the accumulation of NADH. The results were normalized to mg of total cell protein. Strain K4 corresponds to a strain in which the four modules of the reductive glycine pathway were introduced into its genome, that is, gC1M gC2M gC3M gEM, while strain K4e the same strain after short term evolution.

Figure 15:
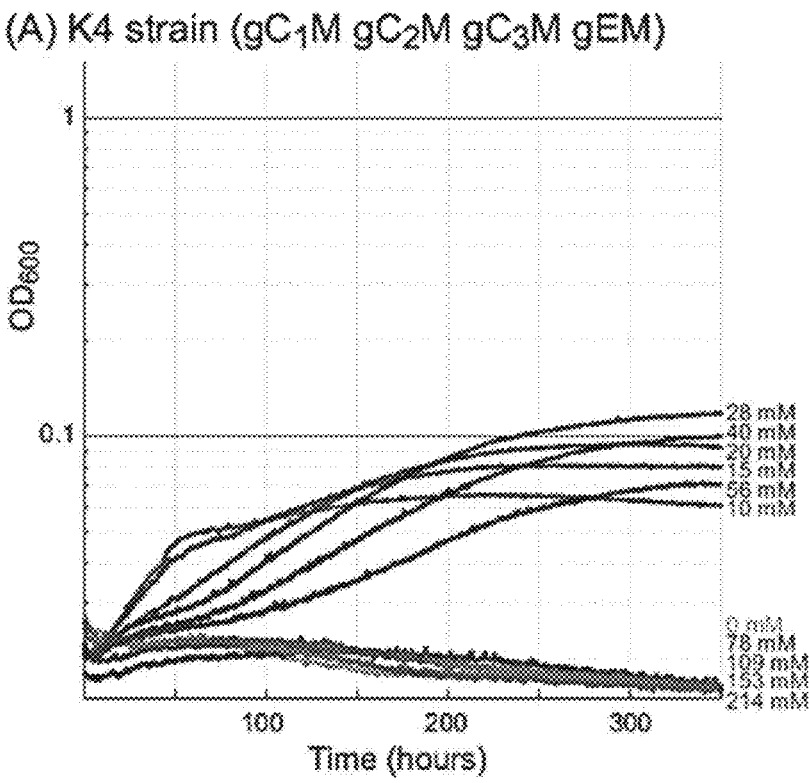
Figure 15:
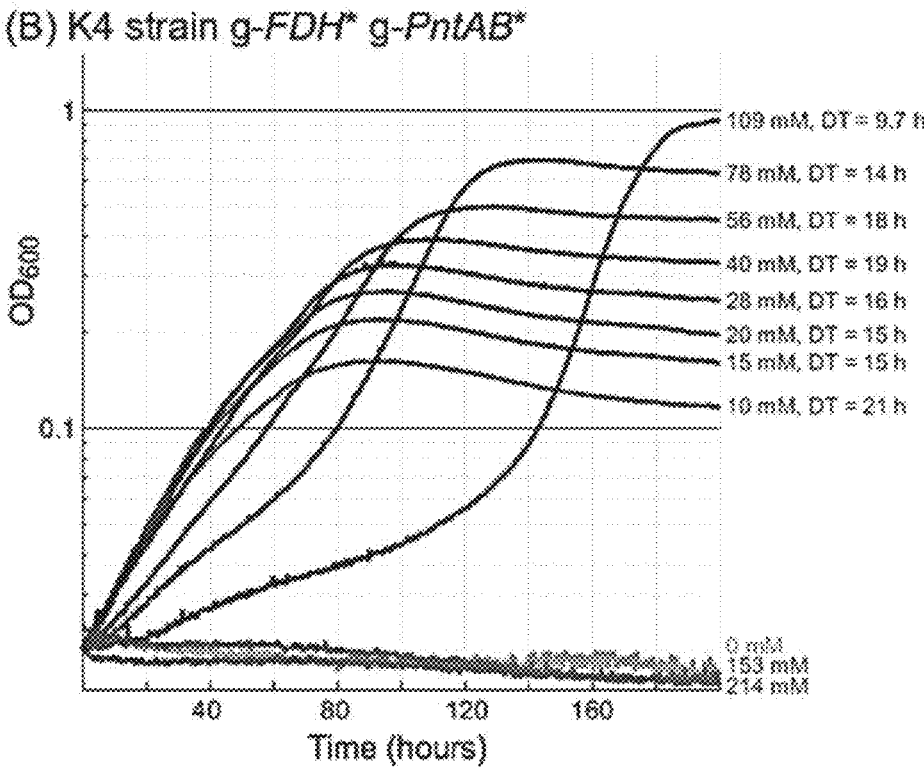

FIG. 15—Introduction of the two mutations found in genome sequencing of the evolved strain (5'UTR of fdh and promoter region of pntAB) improved growth on formate dramatically and resulted in a growth pattern very similar to that of the evolve strain (see FIG. 3C). Cultivation of the evolved strain on formate as a sole carbon source within a 96-well plate. Experiments were conducted at 10% CO2. Plate reader experiments were performed in triplicate, which displayed identical growth curves (±5%), and hence were averaged. Strain K4 corresponds to a strain in which the four modules of the reductive glycine pathway were introduced into its genome, that is, gC1M gC2M gC3M gEM.

Figure 16:
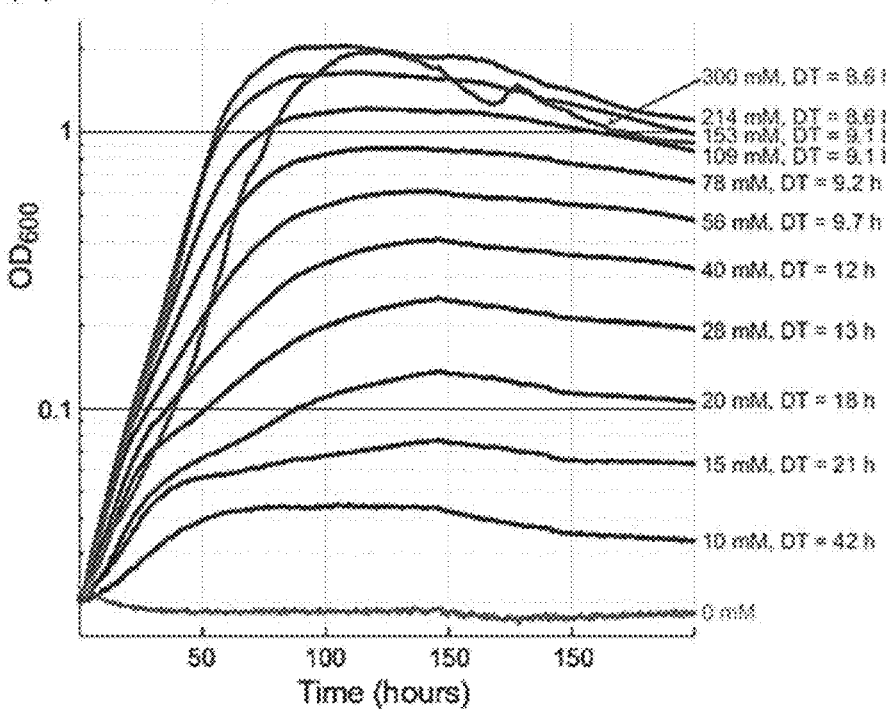
Figure 16:
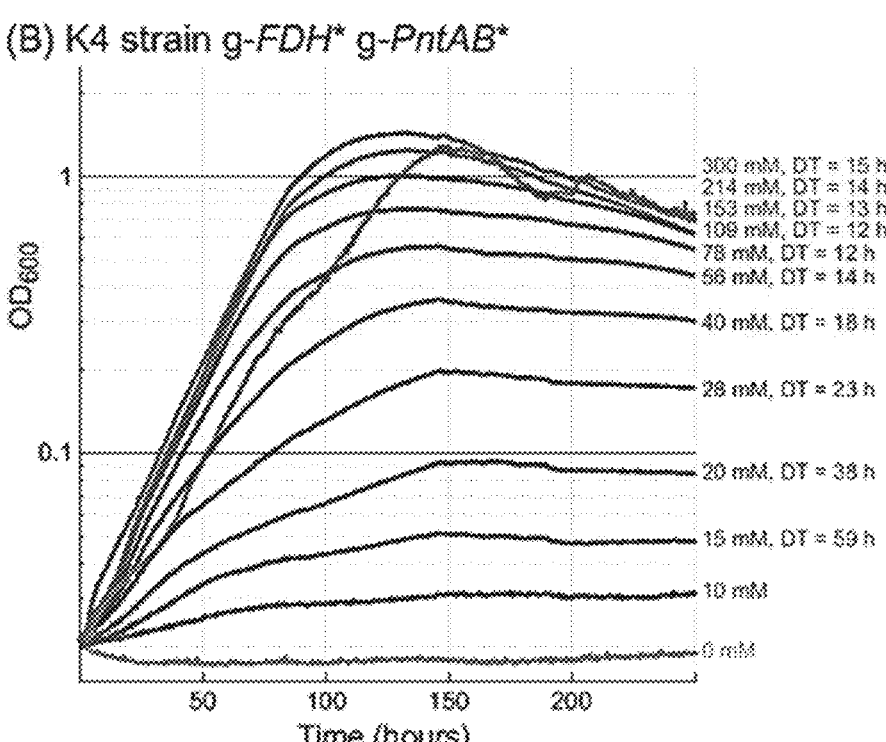

FIG. 16—Addition of 100 mM sodium bicarbonate enables growth on higher concentrations for formate, as demonstrated with the evolved K4 strain and a K4 strain to the genome of which the two mutations found in the evolved strain were introduced. Cultivation of the evolved strain on formate as a sole carbon source within a 96-well plate. Experiments were conducted at 10% CO2. Plate reader experiments were performed in triplicate, which displayed identical growth curves (±5%), and hence were averaged. Strain K4 corresponds to a strain in which the four modules of the reductive glycine pathway were introduced into its genome, that is, gC1M gC2M gC3M gEM.

Figure 17:
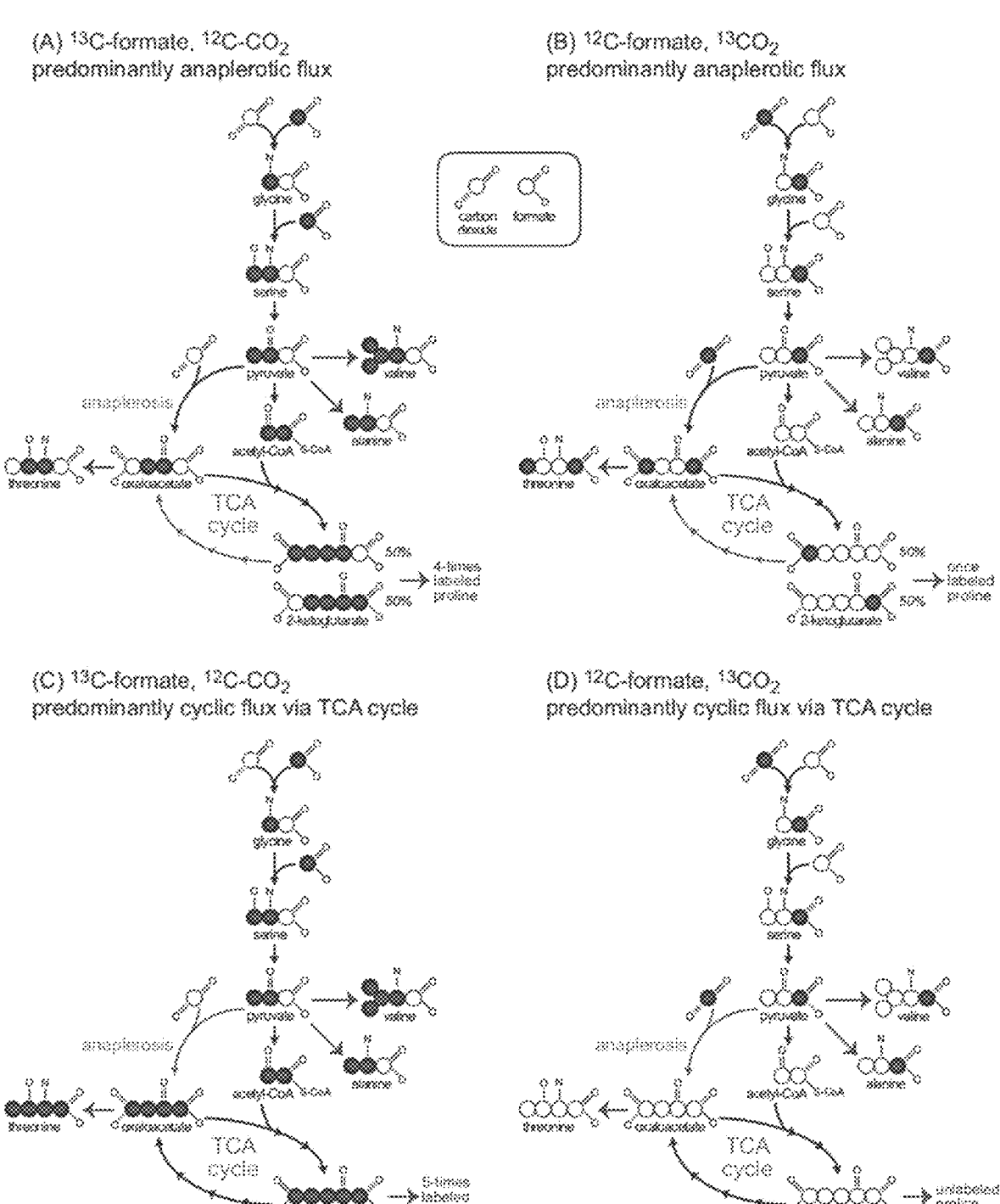

FIG. 17—Expected labeling of proteinogenic amino acids upon feeding with 13C-formate/12C-CO2or 12C-formate/13C-CO2 and according to different metabolic scenarios.

Figure 18:
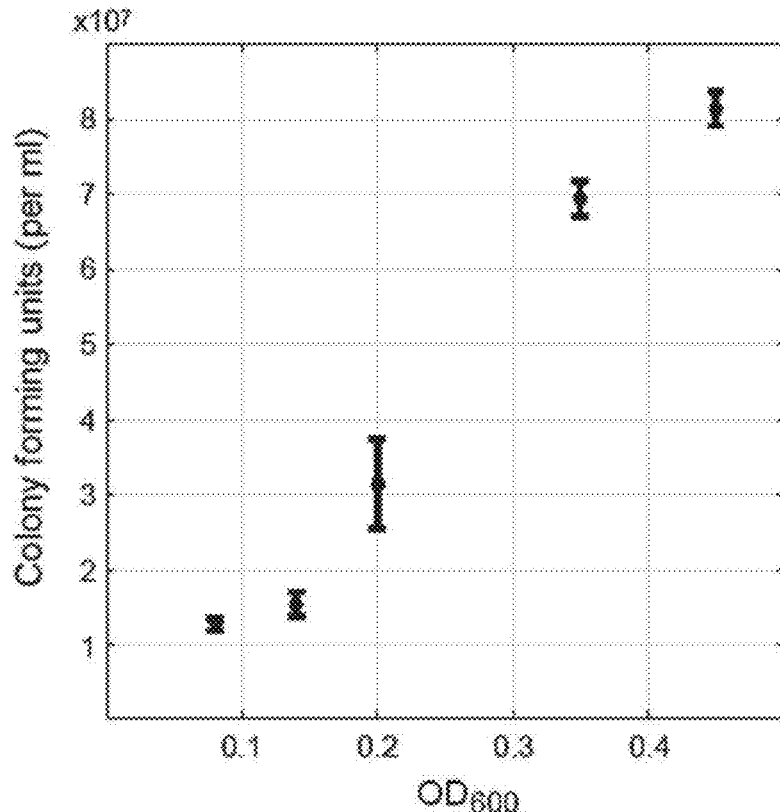

FIG. 18—Number of colony forming units increases monotonically with OD600 for cells growing on methanol as sole carbon source.

Figure 19:
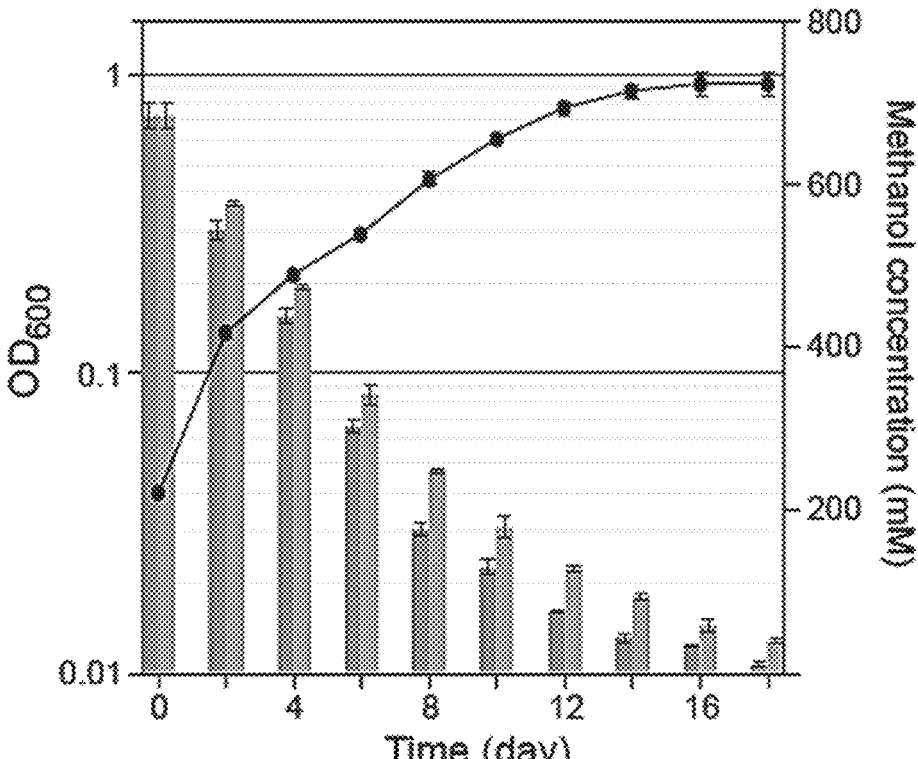

FIG. 19—Addition of 100 mM sodium bicarbonate increases final OD600 on methanol, reaching 0.9 instead of 0.2 (FIG. 5C). Consumption of methanol is depicted by the bars: the grey bars correspond to methanol concentration in a test tube without cells (concentration decrease due to evaporation), while the blue bars represent the concentration of methanol in a test tube in which cells are growing on methanol.

The examples illustrate the invention.

EXAMPLE 1—RESULTS

The Reductive Glycine Pathway

*Escherichia coli*, as most other key biotechnological microorganisms, cannot naturally grow on $C_1$ feedstocks. In this study, it was aimed to design and engineer a simple, linear synthetic pathway which could support *E. coli* growth on formate or methanol as sole carbon source. The inspiration came from the anaerobic reductive acetyl-CoA pathway (rAcCoAP)[23] which assimilates $C_1$ compounds very efficiently. The reductive glycine pathway (rGlyP), as shown in FIG. 1, was designed to be the aerobic twin of the rAcCoAP[24]. Both are linear routes with limited overlap with central metabolism, minimizing the need for regulatory optimization. Both pathways start with the ligation of formate and tetrahydrofolate (THF), proceed via reduction into a $C_1$-THF intermediate, which is then condensed, within an enzyme complex, with $CO_2$ to generate a $C_2$ compound (acetyl-CoA or glycine). The $C_2$ compound is finally condensed with another $C_1$ moiety and metabolized to generate pyruvate as biomass precursor. Importantly, both the rAc-CoAP and the rGlyP are characterized by a 'flat' thermodynamic profile[24,25], that is, both are mostly reversible such that the direction of the metabolic flux they carry is determined mainly by the concentrations of their substrates and products. This thermodynamic profile, while constraining the driving force of the pathway reactions[26], indicates very high energetic efficiency, where no energetic input, e.g., in the form of ATP hydrolysis, is wasted. Indeed, both pathways are associated with a very low ATP cost: only 1-2 ATP molecules are invested in the metabolism of formate to pyruvate[24]. Yet, unlike the rAcCoAP, the key enzymatic components of which are highly oxygen sensitive, the rGlyP can operate under full aerobic conditions. Hence, the rGlyP represents the most efficient theoretical route—in terms of energy utilization, resources consumption, and biomass yield—to assimilate formate in the presence of oxygen[24].

A recent study suggests that the complete rGlyP might be naturally operating in a phosphite-oxidizing microbe[27]. Moreover, the key enzymatic conversion of the rGlyP, catalyzed by the glycine cleavage system (GCS), was shown to be fully reversible in many organisms[28-30]. Previous studies demonstrated that the GCS can support glycine and serine biosynthesis from formate in an engineered *E. coli* strain at elevated $CO_2$ concentration[31-33]. However, growth of the microorganism on formate (and $CO_2$) as a sole carbon source has not yet been demonstrated and remains an open challenge.

Modular-Engineering Approach Establishes Grow on Formate

To facilitate the establishment of formatotrophic growth, the rGlyP was divided into four metabolic modules (FIG. 6): (i) a $C_1$ Module ($C_iM$), consisting of formate THF ligase, methenyl-THF cyclohydrolase, and methylene-THF dehydrogenase, all from *Methylobacterium extorquens*[34], together converting formate into methylene-THF; (ii) a $C_2$ Module ($C_2M$), consisting of the endogenous enzymes of the GCS (GcvT, GcvH, and GcvP) which condenses methylene-THF with $CO_2$ and ammonia to give glycine; (iii) a $C_3$ Module ($C_3M$), consisting of serine hydroxymethyltransferase (SHMT) and serine deaminase, together condensing glycine with another methylene-THF to generate serine and finally pyruvate; and (iv) an Energy Module (EM), which consists of formate dehydrogenase (FDH) from *Pseudomonas* sp. (strain 101)[35], generating reducing power and energy from this $C_1$ feedstock.

The strategy was to establish the activities of the different modules in consecutive steps, integrating subsequent modules and selecting for their combined activity. It was started with an *E. coli* strain that is auxotrophic for serine, glycine, and $C_1$ moieties—$\Delta serA \Delta kbl \Delta ltaE \Delta aceA$—where the first deletion abolishes native serine biosynthesis, the second and third abolish threonine cleavage to glycine, and the final deletion prevents the formation of glyoxylate that could potentially be aminated to glycine[32]. The combined activity of the $C_1M$ and the $C_2M$, together with the native activity of SHMT, should enable the cell to metabolize formate into $C_1$-THF, glycine, and serine, relieving these auxotrophies (FIG. 2A).

Into the serine auxotroph strain, the enzymes of the $C_1M$ and the $C_2M$ were introduced, either on plasmid or in the genome (FIG. 6). For genome integration of $C_1M$, all relevant enzymes were combined into one operon, under the regulation of a strong constitutive promoter[36], which was inserted into a genomic 'safe spot', SS9[37]. In the case of the $C_2M$, the native promoter of the GCS was replaced with a strong constitutive one (FIG. 6), increasing transcript levels 20-50 fold (FIG. 7). As expected, growth with formate was observed upon overexpression of both modules (FIG. 2B) and was dependent upon high $CO_2$ concentration (10% in the headspace) which thermodynamically and kinetically supports the reductive activity of the GCS. While genomic integration of the enzymes of the $C_1M$ (gC,M) did not improve growth compared to plasmid expression (pC$_1$M), replacing plasmid borne expression of the enzymes of the $C_2M$ (pC$_2$M) with genomic overexpression (gC$_2$M) supported a higher growth rate (FIG. 2B).

Next, it was aimed to establish formate as the primary carbon source, which requires high expression of the enzymes of the $C_3M$ to convert glycine into the central metabolism intermediate pyruvate (FIG. 2C). To enable formate assimilation to biomass, an energy source is required, which at this stage was chosen to be acetate. The TCA cycle can fully oxidize acetate to generate reducing power and energy, while the deletion of isocitrate lyase ($\Delta aceA$) abolishes the activity of the glyoxylate shunt, thus preventing the cell from using this molecule as a carbon source. Growth should thus be dependent on formate assimilation via the rGlyP for biomass generation and acetate oxidation for the production of reducing power and energy (FIG. 2C).

The enzymes of the $C_3M$ were either overexpressed on a plasmid (pC$_3$M) or in the genome (gC$_3$M) (FIG. 6); in the latter case, the native glyA and sdaA were deleted and a synthetic operon harboring both genes under the regulation of a strong constitutive promoter was introduced into another genomic 'safe spot', SS7[37]. Overexpression of the enzymes of the $C_3M$, within a strain that genomically expresses the enzymes of the $C_1M$ and the $C_2M$, resulted on growth on formate and acetate (at 10% $CO_2$) (FIG. 2D). Genomic expression of $C_3M$ supported more robust growth compared to the $C_3M$ expressed from plasmid. To confirm that the expression level of $C_3M$ does not constrain the growth rate, a strain was tested in which the expression of glyA and sdaA is controlled by a stronger ribosome binding site (RBS-A instead of RBS-C[36]). It was found that this strain grows rather poorly (FIG. 8), indicating that higher expression of these genes is deleterious.

Finally, it was aimed to introduce the EM such that formate can serve as sole carbon and energy source (FIG. 2E). Overexpression of FDH on a plasmid (FIG. 6), in the strain carrying the genes of the $C_1M$, $C_2M$ and $C_3M$ in the genome, enables growth on formate (FIG. 9). However, when FDH was introduced into yet another genomic 'safe spot', SS10[37], it failed to establish growth (FIG. 9), suggesting that the expression level of FDH was too low. Therefore, a strain was tested in which the genomic expression of FDH was controlled by a stronger ribosome binding site (RBS-A instead of RBS-C[36], FIG. 6). This strain, carrying no plasmid, was able to grow on formate as a sole carbon and energy source (FIG. 2F and FIG. 9). Growth on formate was also observed in a test-tube and confirmed by recording monotonically increasing colony-forming units with increased OD (FIG. 10). This is the first case in which growth on formate was made possible in a microorganism that cannot assimilate $C_1$ compounds natively.

Short-Term Evolution Improves Growth on Formate

To improve growth on formate it was decided to conduct a short term evolution experiment in fed batch mode. The engineered strain was cultivated in test tubes, where formate was added every 3-6 days, increasing the concentration in the medium by 30 mM (red arrows in FIG. 3A). Once cell turbidity reached an $OD_{600}$ of 0.4, the cells were diluted to $OD_{600}$ of 0.03-0.05 and started a new cycle of cultivation (FIG. 3A shows six typical cycles).

Within 13 cultivation cycles (≤40 generations), growth rate on formate was substantially improved (FIG. 3A), with the doubling time dropping from 65-80 h in the first two cycles to less than 10 h in the last cycle (FIG. 3B). Growth yield on formate also improved, from ≈1.5 gCDW/mol-formate in the first cycle to 2.3±0.2 gCDW/mol-formate in the last. This yield is similar to that of microorganisms growing autotrophically on formate via the Calvin cycle (3.2±1.1 gCDW/mol-formate[38]). The growth of the evolved bacterium on formate was directly coupled to a decrease in the concentration of the feedstock in the medium (FIG. 3C). Furthermore, as formatotrophy consumes protons (net oxidation and net assimilation both consume formic acid rather than formate), a direct correlation was observed between cell density and the pH of the medium (FIG. 11).

To better characterize growth on formate, growth experiments were conducted in 96-well plates, automatically measuring $OD_{600}$ every ~10 minutes. It was found that maximal cell density increased monotonically with increasing formate concentration from 10 mM to 150 mM (FIG. 3D). Similarly, the doubling time decreased monotonically with increasing formate concentration: from 17 hours with 10 mM formate to less than 8 hours at formate concentrations higher than 100 mM (FIG. 3D). The cellular toxicity of formate, which is attributed to inhibition of cytochrome c oxidase[39] and dissipation of the proton motive force[40], probably explains the increased lag time at formate concentrations of 109 mM and 153 mM, and the failure to grow at higher concentrations.

Adaptive laboratory evolution usually requires hundreds of generation to improve the fitness of *E. coli* in a substantial way[41-43]. The strain required less than 40 generations, presumably as the growth of the parent strain was so poor that a small number of mutations were sufficient to drastically improve fitness. To check whether this is indeed the case, multiple colonies of the evolved strain were isolated and their genomes were sequenced. Two mutations were found which occurred in all sequenced colonies (FIG. 12). The first was a single base-pair substitution in the 5'-UTR of the newly introduced FDH gene, which increased the level of transcript 2.5-fold (FIG. 13) and resulted in a 7.4-fold increase in formate oxidation activity in cell extract assays (FIG. 14). The second mutation was a single base-pair substitution in the promoter region of pntAB, which encodes for the membrane-bound transhydrogenase. This mutation increased transcript level by more than 13-fold (FIG. 13). The beneficial effect of these two mutations is to be expected, as the first increases energy supply to the cell from formate and the second increases the availability of NAPDH, a key cofactor for the activity of the rGlyP (consumed by methylene-THF dehydrogenase), the supply of which could limit pathway activity.

To confirm that the two mutations suffice to support the improved growth on formate, Multiplex Automated Genomic Engineering (MAGE[44]) was used to introduce these mutations into a non-evolved strain. It was found that while the parent strain could hardly grow in 96-well plates, the strain in which the two mutations were present displayed a growth profile almost identical to that of the evolved strain (FIG. 15). It was therefore concluded that overexpression of FDH and PntAB were sufficient to enable the observed improved growth on formate. By further optimizing cultivation conditions, it was found that addition of 100 mM sodium bicarbonate to the medium enabled the evolved strain, as well as the reconstructed strain, to grow at higher formate concentrations, tolerating even 300 mM (FIG. 16).

Carbon Labeling Confirms Pathway Activity and Shed Light on Cellular Fluxes

To confirm that growth on formate indeed proceeds via the rGlyP, carbon labeling experiments were performed. The cultures were fed with $^{13}C$-formate/$^{12}CO_2$, $^{12}C$-formate/$^{13}CO_2$, and $^{13}C$-formate/$^{13}CO_2$, and measured the labeling pattern of proteinogenic amino-acids using liquid chromatography-mass spectrometry. The focus was on 7 amino-acids—glycine, serine, alanine, valine, proline, threonine, and histidine—which either directly relate to the activity of the rGlyP or originate from different parts of central metabolism, thus providing an indication of key metabolic fluxes.

As shown in FIG. 4, the amino acid labeling confirms the activity of the rGlyP. Specifically, feeding $^{13}C$-formate/$^{12}CO_2$ resulted in single labeled glycine and double labeled serine and pyruvate (as indicated by the labeling of alanine). As valine—derived from two pyruvate molecules, one of which loses its carboxylic acid carbon—is mostly quadruple labeled, it was deduce that pyruvate is labeled in its two non-carboxylic carbons, as predicted for growth via the rGlyP (FIG. 17). Conversely, feeding $^{12}C$-formate/$^{13}CO_2$ resulted, as expected, in single labeled glycine, serine and pyruvate. As valine is also single labeled, it was deduced that pyruvate is labeled in its carboxylic carbon, again confirming the activity of the rGlyP (FIG. 17). Upon feeding $^{13}C$-formate/$^{13}CO_2$, all amino-acids were nearly-completely labeled, where the overall fraction of labeled carbon (marked above the bars in FIG. 4 in italics) is 97-98%, as expected by feeding with 99% $^{13}C$-labeled formate and 99% $^{13}C$-labeled $CO_2$.

The labeling of threonine (derived from oxaloacetate) and proline (derived from 2-ketoglutarate) sheds light on the flux via the anaplerotic reactions and the TCA cycle. Specifically, if cyclic flux via the TCA cycle would predominate over anaplerotic flux, threonine and proline would be expected to be almost fully labeled upon feeding with $^{13}C$-formate and almost fully unlabeled when feeding with $^{13}CO_2$ (FIG. 17). Conversely, if anaplerotic flux and non-cyclic flux would predominate over the cyclic flux, then threonine would be expected to be mostly double labeled on either $^{13}C$-formate or $^{13}CO_2$ and proline would be expected to be mostly quadruple labeled on $^{13}C$-formate and single labeled on $^{13}CO_2$ (FIG. 17). The results shown in FIG. 4 are thus consistent with high anaplerotic flux and low cyclic flux. This indicates that the cell obtains sufficient reducing power and energy from formate oxidation via FDH, and hence does not need to wastefully oxidize the assimilated carbons within pyruvate and acetate (i.e., investing cellular resources for $C_1$ assimilation, only to completely oxidize the assimilated product).

Engineered Growth of *E.coli* on Methanol

Next, it was aimed to use the rGlyP for methanol assimilation. A single enzyme, methanol dehydrogenase (MDH), can convert methanol to formaldehyde, which can be oxidized to formate by the endogenous glutathione system[45] (FIG. 5A). The expression of MDH can thus be regarded as the introduction of another module—Methanol Module (MM)—that serves to metabolize methanol to formate, while providing the cells with reducing power (FIG. 5B). NAD-dependent MDH from several organisms was tested: *Bacillus stearothermophilus* (BsMDH) [19], *Corynebacterium glutamicum* (CgMDH) [46], and *Cupriavidus necator* N-1 (CnMDH)[47], as well as two MDHs from *Bacillus methanolicus* (BmMDH2 and BmMDH3)[10,48] and an improved variant (BmMDH2*, carrying Q5L A363L modifications)[48] These MDH variants were expressed on plasmids in three genetic backgrounds: the parent strain (gC$_1$M gC$_2$M gC$_3$M gEM), the evolved strain, and the parent strain to which the mutation within the promoter of the pntAB (FIG. 12) was introduced via MAGE. Overexpression of BsMDH supported growth on 600 mM methanol, which was most efficient in the latter strain (FIG. 5C) and somewhat poorer in the other strains (FIG. 5D). Growth was confirmed by observing monotonically increasing colony-forming units with increased OD (FIG. 18). The other MDH variants failed to support growth (FIG. 5D, final OD$_{600}$ not higher than inoculation, as indicated by the brown dashed line).

To confirm that growth on methanol indeed depends on formaldehyde oxidation via the glutathione system, the endogenous genes encoding for S-(hydroxymethyl)glutathione dehydrogenase (ΔfrmA) were deleted in the above strains. The deletion was found to completely abolish growth on methanol (FIG. 5D), confirming the essentiality of the glutathione system to the observed growth. Moreover, overexpression of NAD-dependent formaldehyde dehydrogenase from *Pseudomonas putida* (PpFADH; SEQ ID NOs: 49 and 50), as demonstrated in a previous study [12], or from *Pseudomonas aeruginosa* (PaFADH[49]; SEQ ID NOs: 51 and 52) did not improve growth on methanol (FIG. 5D), indicating that the endogenous glutathione system is sufficiently fast and that the rate limiting step lies in methanol oxidation.

To confirm that growth on methanol indeed proceed via the rGlyP, a carbon labeling experiment was performed. The cultures were fed with $^{13}$C-methanol/$^{12}$CO$_2$ and the labeling pattern of the proteinogenic amino-acids described above was measured. The measured labeling pattern (FIG. 5E) was essentially identical to that observed with $^{13}$C-formate/$^{12}$CO$_2$ (FIG. 4), confirming that growth on methanol takes place via the synthetic route.

Notably, the growth rate on methanol was considerably lower than that on formate—doubling time of 54±5.5 h. This can be attributed to the slow rate of methanol oxidation. The observed biomass yield was 4.2±0.17 gCDW / mole methanol, considerably lower than that of microorganisms naturally growing on methanol (7.2±1.2 gCDW/mol-methanol via the Calvin cycle, 12±1.6 gCDW/mol-methanol via the serine cycle, and 15.6±2.7 gCDW/mol-methanol via the RuMP cycle[38]). It is speculated that the low yield is also related to the slow rate of methanol oxidation: a low growth rate increases the proportional consumption of energy for cell maintenance, thus lowering biomass yield. Addition of 100 mM sodium bicarbonate significantly increased the final OD$_{600}$, but the growth parameters did not improve: doubling time of 55±1 h and biomass yield of 4.2±0.1 gCDW/mol-methanol (FIG. 19, also showing methanol consumption during growth).

Conclusions

This study provides the first demonstration of synthetic formatotrophy and methylotrophy. It is shown that rational design alone can suffice to achieve such a goal, but that short term evolution can provide useful fine tuning to improve growth characteristics. Further improvement of growth on formate and methanol can be achieved via long term evolution or via the introduction of metabolic routes that bypass limiting reactions. For example, replacing NAD-dependent MDH with methanol oxidase might reduce biomass yield (as this enzyme dissipates reducing power) but could support a much higher growth rate, as it replaces a thermodynamically- and kinetically-limited reaction with a favorable and fast one. The C$_1$ assimilating strains can be further engineered for the production of value-added chemicals. Especially interesting are chemicals that can be derived directly from the rGlyP intermediates or product, and can thus be produced with high yield and productivity. For example, lactate and isobutanol, both of which are derived from pyruvate, should be produced with high yield. Similarly, cysteine, which is derived from serine, a key pathway intermediate, might be an ideal product. Coupling the abiotic synthesis of formate and methanol with their microbial conversion to chemicals of interest will enable an integrated process for the valorization of CO$_2$ into renewable commodities.

EXAMPLE 2—MATERIAL AND METHODS

Chemicals and Reagents

Primers were synthesized by Integrated DNA Technologies (IDT, Leuven, Belgium). PCR reactions were carried out either using Phusion High-Fidelity DNA Polymerase or Dream Taq. Restrictions and ligations were performed using FastDigest enzymes and T4 DNA ligase, respectively, all purchased from Thermo Fisher Scientific (Dreieich, Germany). Glycine, sodium formate, sodium formate-$^{13}$C, methanol-$^{13}$C were ordered from Sigma-Aldrich (Steinheim, Germany). $^{13}$CO$_2$ was ordered from Cambridge Isotope Laboratories, Inc. (Andover, Mass., USA).

Bacterial Strains

Wild type *Escherichia coli* strain MG1655 (F$^-$λ$^-$ilvG$^-$ rfb-50 rph-1) was used as the host for all genetic modifications. *E. coli* strain DH5α (F$^-$, λ$^-$,φ80/lacZΔM15, Δ(lacZYA-argF)U169, deoR, recA1, endA1, hsdR17(rK$^-$mK$^+$), phoA, supE44, thi-1, gyrA96, relA1) and *E. coli* strain ST18 (pro thi hsdR$^+$ Tp$^r$ Sm$^{r-}$; chromosome::RP4-2 Tc::Mu-Kan::Tn7λpir ΔhemA)[50] were used for cloning and conjugation procedures, respectively.

Genome Engineering

Gene knockouts were introduced in MG1655 by P1 phage transduction[51]. Single gene knockout mutants from the National BioResource Project (NIG, Japan)[52] were used as donors of specific mutations. For the recycling of selection marker (as the multiple gene deletions and integrations were required) all the antibiotic cassettes integrated into genome were flanked by FRT (Flippase Recongnition Target) sites. Cells were transformed with a flippase recombinase helper plasmid (FLPe, replicating at 30° C., Gene Bridges), which carries a gene encoding FLP which recombines at the FRT sites and removes the antibiotic cassette. Elevated temperature (37° C.) was subsequently used to cure the cell from the FLPe plasmid.

Exchange of *E. coli* native promoter with a synthetic one was performed by using PCR-mediated λ-Red recombination method. The synthetic promoter fused with FRT-flanked kanamycin resistance gene was cloned into the pZ vector and the DNA fragment was obtained by PCR amplification with primers containing 50 base pair homology for recombination. Recombinant *E. coli* MG1655 harboring λ-Red recombinase (pRed/ET, Gene Bridges) was cultivated at 30° C., and the expression of λ-Red recombinase was induced by the addition of 10 mM L-arabinose. Electro-competent cells were prepared by washing three times with ddH$_2$O. The PCR product was introduced into *E. coli* expressing the λ-Red recombinase via electroporation. Mutants with exchanged promoter occurred via homologous recombination, selected on the LB agar plate containing 50 μg ml$^{-1}$ kanamycin, and subsequently screened by colony PCR.

To enable genomic overexpression from a synthetic operon, conjugation based genetic recombination methods was adapted as previously described[36]. The synthetic operons were digested with Bcul and Notl, and ligated by T4 ligase into previously digested with the same enzyme pDM4 (with oriR6K) genome integration vector. This vector has two 600 bp homology region compatible with target spot, chloramphenicol resistance gene (camR), a levansucrase gene (sacB), and the conjugation gene traJl for the transfer of the plasmid. The resulting ligation products were used to transform chemically competent *E. coli* ST18 strains. Positive clones growing on chloramphenicol medium supplemented with 5-aminolevulinic acid (50 mg mi$^{-1}$) were identified by colony PCR, and the confirmed recombinant ST18 strain was used as donor strain for the conjugation. Chloramphenicol resisting recipient *E. coli* strains were screened as positive strains for the first round of recombination. Subsequently, sucrose counter selection and kanamycin resistance tests were carried out to isolate recombinant *E. coli* strains with the correct synthetic operon integration into chromosome. All constructs were verified via PCR and sequencing.

Introducing point mutations on genome—to establish the mutation shown in FIG. 12—was achieved by using multiplex automated genome engineering (MAGE)[44,53]. A single colony of desired strain(s) transformed with pORTMAGE[53]

(Addgene catalog no. 72680) was incubated in LB medium supplemented with 100 mg I$^{-1}$ of ampicillin at 30° C. in a shacking incubator. To start the MAGE cycle, overnight cultures were diluted by 100 times in the same medium and cultivated to an optical density of 0.4-0.5 at 600 nm. 1 ml of each culture was transferred to sterile microcentrifuge tubes, and then transferred to 42° C. thermomixer (Thermomixer C, Eppendorf) to express λ-Red genes by heat shock for 15 min at 1000 rpm. After induction, cells were quickly chilled on ice for at least 15 min, and then made electrocompetent by washing three times with ice-cold ddH$_2$O. 40 ul of electrocompetent cell was mixed with 2 ul of 50 uM of oligomer stock solution and the final volume of the suspension was adjusted to 50 ul. The oligomers used for MAGE were: 5"-T*T*T TTG GCG CTA GAT CAC AGG CAT AAT TTT CAG TAC GTT ATA GGG tGT TTG TTA CTA ATT TAT TTT AAC GGA GTA ACA TTT AGC TCG T*A*C -3" (pntAB_MAGE; SEQ ID NO: 53), 5'-T*A*A AGT TAA ACA AAA TTA TTT CTA TTA ACT AGT GAA TTC GGT CAt TGC GTC CTG CGC ATA TTA TAT GTG AAT CAC AGT GAT ATG TCA A*G*T-3' (fdh_MAGE; SEQ ID NO: 54) where the asterisk (*) indicates phosphorothiolated bond. Electroporation was done on Gene Pulser XCell (Bio-Rad) set to 1.8 kV, 25 μF capacitance, and 200 Ω resistance for 1 mm gap cuvette. Immediately after electroporation, 1 ml of LB was added to cuvette and the electroporation mixes in LB was transferred to sterile culture tubes and cultured with shaking at 30° C., 240 rpm for 1 hour to allow for recovery. After recovery, 2 ml of LB medium supplemented with ampicillin was added and then further incubated in the same condition. When the culture reached an OD$_{600}$ of 0.4-0.5, cells were either subjected to additional MAGE cycle or analyzed for genotype via PCR and sequencing. 8 consecutive MAGE cycles were performed before analyzing the genotype to identify strains carrying the required mutations.

All strains used are shown in Table 1.

TABLE 1

| Strains and plasmids used in this study | | |
|---|---|---|
| Strain/Plasmid | Description/Genotype | Source |
| Strains | | |
| MG1655 | F$^-$ λ$^-$ ilvG$^-$ rfb-50 rph- | 1 |
| DH5α | F$^-$ λ$^-$ Φ80lacZΔM15 Δ(lacZYA-argF)U169 deoR recA1 endA1 hsdR17(rK$^-$ mK$^+$) phoA supE44 thi-1 gyrA96 relA1 | 2 |
| ST18 | pro thi hsdR$^+$ Tp$^r$ Sm$^r$; chromosome::RP4-2 Tc::Mu-Kan::Tn7/λpir ΔhemA | 3 |
| SerAux | MG1655, ΔserA ΔltaE Δkbl ΔaceA | 4 |
| gC$_1$M | SerAux, ss9-P$_{STRONG}$-RBS$_C$-ftfL-RBS$_C$-fch-RBS$_C$-mtdA | This study |
| gC$_2$M | SerAux, P$_{STRONG}$-RBS$_C$-gcvT-RBS$_{NATIVE}$-gcvH-RBS$_{NATIVE}$-gcvP | This study |
| gCM gC$_2$M | gC$_1$M, P$_{STRONG}$-RBS$_C$-gcvT-RBS$_{NATIVE}$-gcvH-RBS$_{NATIVE}$-gcvP | This study |
| gC$_1$M gC$_2$M gC$_3$M | gC$_1$M gC$_2$M, ss7-P$_{STRONG}$-RBS$_C$-glyA-RBS$_C$-sdaA ΔsdaA ΔglyA | This study |
| gC$_1$M gC$_2$M gC$_3$M' | gC$_1$M gC$_2$M, ss7-P$_{STRONG}$-RBS$_A$-glyA-RBS$_A$-sdaA ΔsdaA ΔglyA | This study |
| gC$_1$M gC$_2$M gC$_3$M gEM (K4) | gC$_1$M gC$_2$M gC$_3$M, ss10-P$_{STRONG}$-RBS$_A$-fdh | This study |
| gC$_1$M gC$_2$M gC$_3$M gEM' | gC$_1$M gC$_2$M gC$_3$M, ss10-P$_{STRONG}$-RBS$_C$-fdh | This study |
| K4 g-PntAB* | K4 strain with a point mutation in promoter region of pntAB | This study |
| K4 g-FDH* g-PntAB* | K4 strain with a point mutation in both promoter region of pntAB and 5'UTR region of ss10-P$_{STRONG}$-RBS$_A$-fdh | This study |
| K4e | Evolved K4 strain after short term evolution | This study |

TABLE 1-continued

| Strains and plasmids used in this study | | |
|---|---|---|
| Strain/Plasmid | Description/Genotype | Source |
| Plasmids | | |
| pDM4 | Conjugation plasmid with oriR6K origin, sacB, traJI and chloramphenicol/kanamycin resistance | 5 |
| pZASS | Overexpression plasmid with p15A origin, streptomycin resistance, constitutive strong strength promoter ($P_{STRONG}$) | 5 |
| pZASM | Overexpression plasmid with p15A origin, streptomycin resistance, constitutive medium strength promoter ($P_{MEDIUM}$) | 5 |
| pZATM | Overexpression plasmid with p15A origin, tetracycline resistance, constitutive medium strength promoter ($P_{MEDIUM}$) | 5 |
| pZSSM | Overexpression plasmid with pSC101 origin, streptomycin resistance, constitutive medium strength promoter ($P_{MEDIUM}$) | 5 |
| pDM4:SS9-C$_1$M | pDM4 backbone with 600 bp up/down homology to safe spot 9 [6] for the genome integration of $P_{STRONG}$-RBS$_C$-ftfL-RBS$_C$-fch-RBS$_C$-mtdA | This study |
| pDM4:SS7-C$_3$M | pDM4 backbone with 600 bp up/down homology to safe spot 7 [6] for the genome integration of $P_{STRONG}$-RBS$_C$-glyA-RBS$_C$-sdaA | This study |
| pDM4:SS10-EM | pDM4 backbone with 600 bp up/down homology to safe spot 10 [6] for the genome integration of $P_{STRONG}$-RBS$_A$-fdh | This study |
| pC$_1$M | pZSSM backbone for overexpression of RBS$_C$-ftfL-RBS$_C$-fch-RBSc-mtdA from *Methylobacterium extorquens* | 4 |
| pC$_2$M | pZATM backbone for overexpression of RBS$_C$-gcvT-RBS$_C$-gcvH-RBS$_C$-gcvP from *E. coli* | 4 |
| pC$_3$M | pZASS backbone for overexpression of RBS$_C$-glyA-RBS$_C$-sdaA from *E. coli* | This study |
| ASS-glyA-sdaA | pZASS backbone for overexpression of RBS$_C$-glyA-RBS$_C$-sdaA from *E. coli* | This study |
| ASM-glyA-sdaA | pZASS backbone for overexpression of RBS$_C$-glyA-RBS$_C$-sdaA from *E. coli* | This study |
| ASS-sdaA | pZASS backbone for overexpression of RBS$_C$-sdaA from *E. coli* | This study |
| ASM-sdaA | pZASM backbone for overexpression of RBS$_C$-sdaA from *E. coli* | This study |
| ASS-fdh | pZASS backbone for overexpression of RBS$_C$-fdh from *Pseudomonas putida* | This study |
| ASS-bsMDH | pZASS backbone for overexpression of methanol dehydrogenase from *Bacillus stearothermophilus* (UnitProt, P42327) | This study |
| ASS-cgMDH | pZASS backbone for overexpression of methanol dehydrogenase from *Corynebacterium glutamicum* (UnitProt, A4QHJ5) | This study |
| ASS-cnMDH | pZASS backbone for overexpression of methanol dehydrogenase from *Cupriavidus necator* (UnitProt, F8GNE5) | This study |
| ASS-bmMDH3 | pZASS backbone for overexpression of methanol dehydrogenase from *Bacillus methanolicus* (Unitprot, I3E2P9) | This study |
| ASS-bmMDH2 | pZASS backbone for overexpression of methanol dehydrogenase from *Bacillus methanolicus* (Unitprot, I3E949) | This study |
| ASS-bmMDH2* | pZASS backbone for overexpression of engineered methanol dehydrogenase (Q5L A363L) from *Bacillus methanolicus* (Unitprot, I3E949) | This study |
| ASS-bsMDH/paFADH | pZASS backbone for overexpression of RBSc-bsMDH-RBSc-paFADH, a formaldehyde dehydrogenase from *Pseudomonas aeruginosa* | This study |
| ASS-bsMDH/ppFADH | pZASS backbone for overexpression of RBSc-bsMDH-RBSc-ppFADH, a formaldehyde dehydrogenase from *Pseudomonas putida* | This study |

REFERENCES IN TABLE Table 1

1 Blattner, F. R. et al. The complete genome sequence of *Escherichia coli* K-12. *Science* 277, 1453-1462 (1997).

2 Meselson, M. & Yuan, R. DNA restriction enzyme from *E. coli. Nature* 217, 1110-1114 (1968).

3 Thoma, S. & Schobert, M. An improved *Escherichia coli* donor strain for diparental mating. *FEMS Microbiol Lett* 294, 127-132, doi:10.1111/.1574-6968.2009.01556.x (2009).

4 Yishai, O., Bouzon, M., Doring, V. & Bar-Even, A. In Vivo Assimilation of One-Carbon via a Synthetic Reductive Glycine Pathway in *Escherichia coli. ACS synthetic biology*, doi:10.1021/acssynbio.8b00131 (2018).

5 Wenk, S., Yishai, O., Lindner, S. N. & Bar-Even, A. An Engineering Approach for Rewiring Microbial Metabolism. *Methods Enzymol* 608, 329-367, doi:10.1016/bs.mie.2018.04.026 (2018).

5 Bassalo, M. C. et al. Rapid and Efficient One-Step Metabolic Pathway Integration in *E. coli*. *ACS synthetic biology* 5, 561-568, doi:10.1021/acssynbio.5b00187 (2016).

Synthetic-Operon Construction

Protein sequences of formate-tetrahydrofolate ligase (ftfL, UniProt: Q83WS0), 5,10-methenyl-tetrahydrofolate cyclohydrolase (fchA, UniProt: Q49135), and 5,10-methylene-tetrahydrofolate dehydrogenase (mtdA, UniProt: P55818) were taken from *Methylobacterium extorquens* AM1. Formate dehydrogenase (fdh, UniProt: P33160) was taken from *Pseudomonas* sp. Formaldehyde dehydrogenase were obtained from *Pseudomonas aeruginosa* (fdhA, Unit-Prot: Q9HTE3) and *Pseudomonas putida* (fdhA, UnitProt: P46154). Methanol dehydrogenases were prepared from *Bacillus stearothermophilus* (adh, UniProt: P42327), *Corynebacterium glutamicum* (cgR_2695, UniProt: A4QHJ5), *Cupriavidus necator* (mdh2, UniProt: F8GNE5), and *Bacillus methanolicus* (UnitProt: I3E2P9 and I3E949, as well as en engineered MDH, as reported in[48]). These genes were codon optimized for *E. coli* K-12 and synthesized (Baseclear, Netherlands). All gene sequences are listed in sequence protocol of the application.

Genes native to *E. coli*—that is, serine hydroxymethyl-transferase (glyA) and serine deaminase (sdaA)—were prepared via PCR-amplification from *E. coli* MG1655 genome. Genes were integrated into a high copy number cloning vector pNiv to construct synthetic operons using the method described previously[36,54] Plasmid-based gene overexpression was achieved by cloning the desired synthetic operon into the pZ vector (15A origin of replication, streptomycin marker[36]) digested with EcoRI and PstI utilizing T4 DNA ligase. All molecular biology techniques were performed with standard methods[55] or following manufacturer protocol.

Promoters and ribosome binding sites were used as described previously[36,54,56]. Briefly, either a medium strength constitutive promoter ('PGl-10'[56]) or a strong constitutive promoter ('PGl-20'[56]) was used, as indicated in the text and in FIG. 6. Either medium strength ribosome binding site (RBS$_c$[54]) or a strong ribosome binding site (RBS$_A$[54]) was further used, as indicated in the text and in FIG. 6.

All plasmid used are shown in the above Table 1.

Growth Medium and Conditions

Luria Bertani medium (1% NaCl, 0.5% yeast extract, and 1% tryptone) was used for strain propagation. Further cultivation was done in M9 minimal media (50 mM Na$_2$HPO$_4$, 20 mM KH$_2$PO$_4$, 1 mM NaCl, 20 mM NH$_4$Cl, 2 mM MgSO$_4$, and 100 µM CaCl$_2$), with trace elements (134 µM EDTA, 13 µM FeCl$_3$.6H$_2$O, 6.2 µM ZnCl$_2$, 0.76 µM CuCl$_2$.2H$_2$O, 0.42 µM CoCl$_2$.2H$_2$O, 1.62 µM H$_3$BO$_3$, 0.081 µM MnCl$_2$.4H$_2$O). For the cell growth test, overnight cultures in LB medium were used to inoculate a pre-culture at an optical density (600 nm, OD$_{600}$) of 0.02 in 4 ml fresh M9 medium containing 10 mM glucose, 1 mM glycine and 30 mM formate in 10 ml glass test tube. Cell were then cultivated at 37° C. and shaking of 240 rpm. Cell cultures were harvested by centrifugation (18,407×g, 3 min, 4° C.) and washed twice with fresh M9 medium and used to inoculate the main culture, conducted aerobically either in 10 ml glass tube or Nunc 96-well microplates (Thermo Fisher Scientific) with appropriate carbon sources according to strain and specific experiment: 10 mM glucose, 20 mM acetate, 30 mM formate, 600 mM methanol, and/or 10%

CO$_2$ (90% air). In the microplates cultivation, each well containing 150 pl culture covered with 50 µl mineral oil (Sigma-Aldrich) to avoid evaporation (note that small gaseous molecules such as O$_2$ and CO$_2$ can freely diffuse via this oil coverage). Growth experiments were conducted (either 100% air or 90% ai/10% CO$_2$) in a BioTek Epoch 2 plate reader (BioTek Instrument, USA) at 37° C. Growth (OD$_{600}$) was measured after a kinetic cycle of 12 shaking steps, which alternated between linear and orbital (1 mm amplitude), and were each 60 s long. OD values measured in the plate reader were calibrated to represent OD values in standard cuvettes according to ODcuvette=ODplate/0.23. Glass tube culture was carried out in 4 ml of working volume, at 37° C. and shaking of 240 rpm. Volume loss due to evaporation was compensated by adding the appropriate amount of sterile double distilled water (ddH$_2$O) to culture tube every two days. All growth experiments were performed in triplicate, and the growth curves shown represent the average of these triplicates.

$^{13}$C Labeling of Proteinogenic Amino Acids

For stationary isotope tracing of proteinogenic amino acids, cells were cultured in 4 ml of M9 media supplemented with either labeled or unlabeled carbon sources, that is, $^{13}$C-formate, $^{13}$C-methanol and/or $^{13}$CO$_2$, under conditions as described above. A 6 L vacuum desiccator (Lab Companion, South Korea) was used for cultures grown in $^{13}$CO$_2$, where the original gas was expelled by using vacuum pump followed by refilling with 90% air and 10% $^{13}$CO$_2$. The cell was harvested by centrifugation for 3 min at 18,407×g when the stationary growth phase was reached. Biomass was hydrolyzed by incubation with 1 ml of 6 N hydrochloric acid for a duration of 24 h in 95° C. Samples were dried via heating at 95° C. and re-dissolved in 1 ml of ddH$_2$O. Hydrolyzed amino acids were separated using ultra performance liquid chromatography (Acquity, Waters, Milford, MA, USA) using a C18-reversed-phase column (Waters) as previously described[57]. Mass spectra were acquired using an Exactive mass spectrometer (Thermo Fisher). Data analysis was performed using Xcalibur (Thermo Fisher). Prior to analysis, amino-acid standards (Sigma-Aldrich) were analyzed under the same conditions in order to determine typical retention times.

Dry Weight Analysis

To determine dry cell weight of *E. coli* grown formate or methanol, pre-cultures prepared as described above were inoculated to at a final OD$_{600}$ of 0.01 into fresh M9 medium containing either formate (30 mM) or methanol (600 mM) in 125 ml pyrex Erlenmeyer flask and grown at 37° C. with agitation at 240 rpm. Up to 50 ml of cell culture, growing in shake-flasks, were harvested by centrifugation (3,220×g, 20 min). To remove residual medium compounds cells were washed be three cycles of centrifugation (7,000×g, 5 min) and resuspension in 2 ml ddH$_2$O. Cell-solutions were transferred to pre-weighted and pre-dried aluminum dish, dried at 90° C. for 16 h, and weight of the dried cells in the dish was determined and subtracted by the weight of the empty dish.

CDW of *E. coli* strains was measured during exponential growth phase (OD$_{600}$ of 0.3-0.4) in the presence of 10% CO$_2$ on 30 mM formate (at OD$_{600}$ of 0.2, 0.37, and 0.41) and on 600 mM methanol (at OD$_{600}$ of 0.21, 0.22, and 0.24). As a control, CDW of *E. coli* strain growing either on formate or methanol was determined during exponential growth phase in the presence of 10% CO$_2$ and 30 mM formate and either 10 mM glucose (at $OD_{600}$ of 1.26), 20 mM pyruvate (at $OD_{600}$ of 0.78), or 20 mM succinate (at OD600 of 0.37). To determine CDW of *E. coli* WT, cells were grown in the presence of 10% $CO_2$ on 10 mM glucose and CDW was determined during exponential growth phase (at $OD_{600}$ of 0.78).

Enzymes and Chemical Assays

Absorbance changes for all assays were monitored in a BioTek Epoch 2 plate reader. Working at the measurement linear range was confirmed in all assays. Results represent averages of at least three cell preparations. To determine the activity of formate dehydrogenase, 1.5 ml of $OD_{600}$ 1.0 cell culture grown in M9 minimal medium and supplemented with glucose and formate from glass test tubes were washed twice with 9 gl$^{-1}$ sodium chloride. Cells were lysed by adding CelLytic Reagent (Sigma) and allowed to sit for 20 min at the room temperature. After cell disruption, cellular debris was removed by centrifugation (18,407×g, 4° C., 10 min) and the supernatant used for crude assays without further purification. Formate dehydrogenase assay performed in the presence of 10 mM 2-mercaptoethanol, 100 mM sodium formate, 200 mM sodium phosphate buffer pH 7.0, and 2 mM $NAD^+$ in a total volume of 200 µl at 37° C.[58]. The increase in NADH concentration resulting from formate oxidation was monitored at 340 nm. Protein concentration was measured using the Bradford Reagent (Sigma) with bovine serum albumin as a standard. Formate and methanol in the culture were quantified by a colorimetric assay using formate assay kit (Sigma-Aldrich) and methanol assay kit (BioVision) respectively. All samples were diluted to ensure the reading are within the standard curve range according to the manufacturer's instructions.

Quantitative Polymerase Chain Reaction

Total RNA was extracted from 1 ml of overnight culture at an $OD_{600}$ 0.5 using the RNeasy Mini Kit (Qiagen, Hilden, Germany), and following the protocol of the supplier. All RNA samples were treated with DNase I (Sigma-Aldrich, St. Louis, MO, US) to remove any residual DNA. First-strand cDNA was synthesized using a qScript cDNA Synthesis kit following the manufacturer instructions (Quanta Biosciences, Gaithersburg, MD, US), and 1 µg of total RNA was used as a template in 20 µl reaction volume. Quantitative reverse-transcription-polymerase chain reactions (qRT-PCR) were made using a Maxima™ SYBR Green qPCR Master Mix (ThermoFisher Scientific, Darmstadt, Germany) supplemented with 5 µM primers and 5 µl cDNA template, which was diluted up to 200 µl after synthesis. The primers used for QPCR were: GCC AAT CTG CAA CAG TGC TC-3' (pntA_forward, SEQ ID NO: 55), 5'-TTT TTG GCT GGA TGG CM GC-3' (pntA_reverse, SEQ ID NO: 56), 5"-CGT GAC GM TAC CTG ATC GTT -3' (fdh forward, SEQ ID NO: 57), 5"- GGT AGC GTT ACC TTT AGA GTA AGA GTG -3' (fdh reverse, SEQ ID NO: 58). PCR was performed in 96-well optical reaction plates (ThermoFisher Scientific, Darmstadt, Germany) as follows: 10 min at 50° C., 5 min at 95° C., and 40 cycles of 10 s at 95 and 30 s at 60° C., and finally 1 min at 95° C. The specificity of the reactions, and the amplicon identities were verified by melting curve analysis. Reaction mixtures without cDNA were used as a negative control. Data were evaluated using the CT method[59] and with correction for the PCR efficiency, which was determined based on the slope of standard curves. Normalization of gene expression levels were carried on by using the rrsA gene[60], and eventually the fold-differences in the transcript levels and mean standard error were calculated as described elsewhere[59].

Quantification of *E. coli* Colony Forming Units

Viable cell counts were determined by sampling *E. coli* cell cultures periodically. 10 µl of cell culture was diluted in 990 µl sterile M9 medium, and the diluted cell suspension was further diluted either by 100 times or 1000 times to obtain isolated colonies on agar plates. 100 µl of repeatedly diluted cell suspension was plated on LB agar plate and incubated at 37° C. for 24 h. All cell counts experiments were conducted at least five times per each OD value to obtain reliable cell counting numbers.

REFERENCES

1 Blankenship, R. E. et al. Comparing photosynthetic and photovoltaic efficiencies and recognizing the potential for improvement. *Science* 332, 805-809, doi:10.1126/science.1200165 (2011).
2 Scheffe, J. R. & Steinfeld, A. Oxygen exchange materials for solar thermochemical splitting of H2O and CO2: a review. *Materials Today* 17, 341-348 (2014).
3 Snoeckx, R. & Bogaerts, A. Plasma technology—a novel solution for CO2 conversion? *Chem Soc Rev* 46, 5805-5863, doi:10.1039/c6cs00066e (2017).
4 Zhang, Q., Kang, J. & Wang, Y. Development of novel catalysts for Fischer—Tropsch synthesis: tuning the product selectivity. *ChemCatChem* 2, 1030-1058 (2010).
5 Jouny, M., Luc, W. & Jiao, F. General techno-economic analysis of CO2 electrolysis systems. *Ind Eng Chem Res* 57, 2165-2177 (2018).
6 Yishai, O., Lindner, S. N., Gonzalez de la Cruz, J., Tenenboim, H. & Bar-Even, A. The formate bio-economy. *Curr Opin Chem Bio!* 35, 1-9, doi:10.1016/j.cbpa.2016.07.005 (2016).
7 Szima, S. & Cormos, C. C. Improving methanol synthesis from carbon-free H2 and captured CO2: A techno-economic and environmental evaluation. *J CO2 Util* 24, 555-563 (2018).
8 Bertsch, J. & Muller, V. Bioenergetic constraints for conversion of syngas to biofuels in acetogenic bacteria. *Biotechnology for biofuels* 8, 210, doi:10.1186/s13068-015-0393-x (2015).
9 Bennett, R. K., Steinberg, L. M., Chen, W. & Papoutsakis, E. T. Engineering the bioconversion of methane and methanol to fuels and chemicals in native and synthetic methylotrophs. *Curr Opin Biotechnol* 50, 81-93, doi:10.1016/j.copbio.2017.11.010 (2017).
10 Muller, J. E. et al. Engineering *Escherichia coli* for methanol conversion. *Metab Eng* 28, 190-201, doi:10.1016/j.ymben.2014.12.008 (2015).
11 Dai, Z. et al. Metabolic construction strategies for direct methanol utilization in *Saccharomyces cerevisiae*. *Bioresour Technol* 245, 1407-1412, doi:10.1016/j.biortech.2017.05.100 (2017).
12 Yu, H. & Liao, J. C. A modified serine cycle in *Escherichia coli* coverts methanol and CO2 to two-carbon compounds. *Nature communications* 9, 3992, doi:10.1038/s41467-018-06496-4 (2018).
13 Meyer, F. et al. Methanol-essential growth of *Escherichia coli*. *Nature communications* 9, 1508, doi:10.1038/s41467-018-03937-y (2018).
14 Woolston, B. M., King, J. R., Reiter, M., Van Hove, B. & Stephanopoulos, G. Improving formaldehyde consumption drives methanol assimilation in engineered *E. coli*. *Nature communications* 9, 2387, doi:10.1038/s41467-018-04795-4 (2018).

15 Bennett, R. K., Gonzalez, J. E., Whitaker, W. B., Antoniewicz, M. R. & Papoutsakis, E. T. Expression of heterologous non-oxidative pentose phosphate pathway from *Bacillus methanolicus* and phosphoglucose isomerase deletion improves methanol assimilation and metabolite production by a synthetic *Escherichia coli* methylotroph. *Metab Eng, doi:*10.1016/j.ymben.2017.11.016 (2017).

16 Gonzalez, J., Bennett, R. K., Papoutsakis, E. T. & Antoniewicz, M. R. Methanol assimilation in *Escherichia coli* is improved by co-utilization of threonine and deletion of leucine-responsive regulatory protein. *Metab Eng*, doi: 10.1016/j.ymben.2017.11.015 (2017).

17 Rohlhill, J., Sandoval, N. R. & Papoutsakis, E. T. Sort-Seq Approach to Engineering a Formaldehyde-Inducible Promoter for Dynamically Regulated *Escherichia coli* Growth on Methanol. *ACS synthetic biology* 6, 1584-1595, doi:10.102$^1$/$_a$cssynbio.7b00114 (2017).

18 Woolston, B. M., Roth, T., Kohale, I., Liu, D. R. & Stephanopoulos, G. Development of a formaldehyde biosensor with application to synthetic methylotrophy. *Biotechnol Bioeng* 115, 206-215, doi:10.1002/bit.26455 (2018).

19 Whitaker, W. B. et al. Engineering the biological conversion of methanol to specialty chemicals in *Escherichia coli*. *Metab Eng* 39, 49-59, doi:10.1016/j.ymben.2016.10.015 (2017).

20 Lu, X. et al. Constructing a synthetic pathway for acetyl-coenzyme A from one-carbon through enzyme design. *Nature communications* 10, 1378, doi: 10.1038/s41467-019-09095-z (2019).

21 Wang, X. et al. Biological conversion of methanol by evolved *Escherichia coli* carrying a linear methanol assimilation pathway. *Bioresour Bioprocess* 4, 41 (2017).

22 Anthony, C. *The Biochemistry of Methylotrophs*. (Academic Press, 1982).

23 Drake, H. L., Kirsten, K. & Matthies, C. in *The Prokaryotes* 354-420 (Springer New York, 2006).

24 Bar-Even, A., Noor, E., Flamholz, A. & Milo, R. Design and analysis of metabolic pathways supporting formatotrophic growth for electricity-dependent cultivation of microbes. *Biochim Biophys Acta* 1827, 1039-1047 (2013).

25 Bar-Even, A. Does acetogenesis really require especially low reduction potential? *Biochim Biophys Acta* 1827, 395-400, doi:10.1016/j.bbabio.2012.10.007 (2013).

26 Noor, E. et al. Pathway thermodynamics highlights kinetic obstacles in central metabolism. *PLoS Comput Biol* 10, e1003483, doi:10.1371/journal.pcbi.1003483 (2014).

27 Figueroa, I. A. etal. Metagenomics-guided analysis of microbial chemolithoautotrophic phosphite oxidation yields evidence of a seventh natural CO2 fixation pathway. *Proc Natl Acad Sci U S A* 115, E92-E101, doi:10.1073/pnas.1715549114 (2018).

28 Kawasaki, H., Sato, T. & Kikuchi, G. A new reaction for glycine biosynthesis. *Biochem Biophys Res Commun* 23, 227-233 (1966).

29 Motokawa, Y. & Kikuchi, G. Glycine metabolism by rat liver mitochondria. Reconstruction of the reversible glycine cleavage system with partially purified protein components. *Arch Biochem Biophys* 164, 624-633 (1974).

30 Pasternack, L. B., Laude, D. A., Jr. & Appling, D. R. 13C NMR detection of folate-mediated serine and glycine synthesis in vivo in *Saccharomyces cerevisiae*. *Biochemistry* 31, 8713-8719 (1992).

31 Tashiro, Y., Hirano, S., Matson, M. M., Atsumi, S. & Kondo, A. Electrical-biological hybrid system for CO2 reduction. *Metab Eng* 47, 211-218, doi:10.1016/j.ymben.2018.03.015 (2018).

32 Yishai, O., Bouzon, M., Doring, V. & Bar-Even, A. In Vivo Assimilation of One-Carbon via a Synthetic Reductive Glycine Pathway in *Escherichia coli*. *ACS synthetic biology, doi:*10.1021/acssynbio.8b00131 (2018).

33 Bang, J. & Lee, S. Y. Assimilation of formic acid and CO2 by engineered *Escherichia coli* equipped with reconstructed one-carbon assimilation pathways. *Proc Natl Acad Sci USA* 115, E9271-E9279, doi:10.1073/pnas.1810386115 (2018).

34 Crowther, G. J., Kosaly, G. & Lidstrom, M. E. Formate as the main branch point for methylotrophic metabolism in *Methylobacterium extorquens* AM1. *J Bacteriol* 190, 5057-5062 (2008).

35 Tishkov, V. I. & Popov, V. O. Catalytic mechanism and application of formate dehydrogenase. *Biochemistry (Mosc)* 69, 1252-1267, doi:BCM69111537 [pii] (2004).

36 Wenk, S., Yishai, O, Lindner, S. N. & Bar-Even, A. An Engineering Approach for Rewiring Microbial Metabolism. *Methods Enzymol* 608, 329-367, doi:10.1016/bs.mie.2018.04.026 (2018).

37 Bassalo, M. C. et al. Rapid and Efficient One-Step Metabolic Pathway Integration in *E. coli*. *ACS synthetic biology* 5, 561-568, doi:10.1021/acssynbio.5b00187 (2016).

38 Claassens, N. J., Cotton, C. A., Kopljar, D. & Bar-Even, A. Making quantitative sense of electromicrobial production. *Nature Catalysis* 2, 437 (2019).

39 Nicholls, P. Formate as an inhibitor of cytochrome c oxidase. *Biochem Biophys Res Commun* 67, 610-616 (1975).

40 Warnecke, T. & Gill, R. T. Organic acid toxicity, tolerance, and production in *Escherichia coli* biorefining applications. *Microb Cell Fact* 4, 25, doi:10.1186/1475-2859-4-25 (2005).

41 Rudolph, B., Gebendorfer, K. M., Buchner, J. & Winter, J. Evolution of *Escherichia coli* for growth at high temperatures. *J Biol Chem* 285, 19029-19034, doi:10.1074/jbc.M110.103374 (2010).

42 Dragosits, M. & Mattanovich, D. Adaptive laboratory evolution—principles and applications for biotechnology. *Microb Cell Fact* 12, 64, doi:10.1186/1475-2859-12-64 (2013).

43 Wytock, T. P. et al. Experimental evolution of diverse *Escherichia coli* metabolic mutants identifies genetic loci for convergent adaptation of growth rate. *PLoS Genet* 14, e1007284, doi:10.1371/journal.pgen.1007284 (2018).

44 Wang, H. H. et al. Programming cells by multiplex genome engineering and accelerated evolution. *Nature* 460, 894-898, doi:nature08187 [pii] 10.1038/nature08187 (2009).

45 Gutheil, W. G., Kasimoglu, E. & Nicholson, P. C. Induction of glutathione-dependent formaldehyde dehydrogenase activity in *Escherichia coli* and Hemophilus influenza. *Biochem Biophys Res Commun* 238, 693-696 (1997).

46 Kotrbova-Kozak, A., Kotrba, P., lnui, M., Sajdok, J. & Yukawa, H. Transcriptionally regulated adhA gene encodes alcohol dehydrogenase required for ethanol and n-propanol utilization in *Corynebacterium glutamicum* R. *Appl Microbiol Biotechnol* 76, 1347-1356, doi:10.1007/s00253-007-1094-6 (2007).

47 Wu, T. Y. et al. Characterization and evolution of an activator-independent methanol dehydrogenase from *Cupriavidus necator* N-1. *Appl Microbiol Biotechnol* 100, 4969-4983, doi:10.1007/s00253-016-7320-3 (2016).

48 Roth, T. B., Woolston, B. M., Stephanopoulos, G. & Liu, D. R. Phage-Assisted Evolution of *Bacillus methanolicus* Methanol Dehydrogenase 2. *ACS synthetic biology* 8, 796-806, doi:10.102$^1$/$_a$cssynbio.8b00481 (2019).

49 Zhang, W. et al. Expression, purification, and characterization of formaldehyde dehydrogenase from *Pseudomonas aeruginosa*. *Protein Expr Purif* 92, 208-213, doi: 10.1016/j.pep.2013.09.017 (2013).

50 Thoma, S. & Schobert, M. An improved *Escherichia coli* donor strain for diparental mating. *FEMS Microbiol Lett* 294, 127-132, doi:10.1111/j.1574-6968.2009.01556.x (2009).

51 Thomason, L. C., Costantino, N. & Court, D. L. *E. coli* genome manipulation by P1 transduction.*Curr Protoc Mol Biol Chapter* 1, Unit 1 17, doi:10.1002/0471142727.mb0117s79 (2007).

52 Baba, T. et al. Construction of *Escherichia coli* K-12 in-frame, single-gene knockout mutants: the Keio collection. *Mol Syst Biol* 2, 2006-2008, doi:10.1038/msb4100050 (2006).

53 Nyerges, A. et al. A highly precise and portable genome engineering method allows comparison of mutational effects across bacterial species. *Proc Natl Acad Sci U S A* 113, 2502-2507, doi:10.1073/pnas.1520040113 (2016).

54 Zelcbuch, L. et al. Spanning high-dimensional expression space using ribosome-binding site combinatorics. *Nucleic Acids Res* 41, e98, doi:gkt151 [pii] 10.1093/nar/gkt151 (2013).

55 Sambrook, J. & Russell, D. W. *Molecular cloning: a laboratory manual*. 3rd edn, (Cold Spring Harbor Laboratory Press, 2001).

56 Braatsch, S., Helmark, S., Kranz, H., Koebmann, B. & Jensen, P. R. Escherichia coli strains with promoter libraries constructed by Red/ET recombination pave the way for transcriptional fine-tuning. *Biotechniques* 45, 335-337, doi: 000112907 [pii] 10.2144/000112907 (2008).

57 Giavalisco, P. et al. Elemental formula annotation of polar and lipophilic metabolites using 13C, 15N and 34S isotope labelling, in combination with high-resolution mass spectrometry. *Plant J* 68, 364-376 (2011).

58 Liu, A., Feng, R. & Liang, B. Microbial surface displaying formate dehydrogenase and its application in optical detection of formate. *Enzyme Microb Technol* 91, 59-65, doi:10.1016/j.enzmictec.2016.06.002 (2016).

59 Livak, K. J. & Schmittgen, T. D. Analysis of relative gene expression data using real-time quantitative PCR and the 2-ΔΔCT method. *methods* 25, 402-408 (2001).

60 Zhou, K. et al. Novel reference genes for quantifying transcriptional responses of *Escherichia coli* to protein over-expression by quantitative PCR. *BMC Mol Biol* 12, 18, doi:10.1186/1471-2199-12-18 (2011).

The invention claimed is:

1. A genetically engineered microorganism expressing
    (i) a formate tetrahydrofolate (THF) ligase, a methenyl-THF cyclohydrolase, and a methylene-THF dehydrogenase,
    (ii) enzymes of a glycine cleavage system (GCS)
    (iii) a serine deaminase and a serine hydroxymethyltransferase (SHMT),
    (iv) an enzyme increasing the availability of NADPH, wherein the enzyme increasing the availability of NADPH is selected from membrane transhydrogenase (PntAB), glucose 6-phosphate dehydrogenase (Zwf), 6-phosphogluconate dehydrogenase (Gnd), malic B enzyme (MaeB), and isocitrate dehydrogenase (Icd), and
    (v) a formate dehydrogenase (FDH),
    wherein the genetically engineered microorganism has been genetically engineered to express at least one of the enzymes of (i) to (v), wherein said enzyme is not expressed by a corresponding microorganism that has been used to prepare the genetically engineered microorganism, and
    wherein the enzymes of (i) to (v) are genomically expressed under the control of a strong constitutive promoter that leads to robust overexpression of genes encoding the enzymes of (i) to (v) and/or a modified ribosome binding site (RBS) that increases the translation initiation rate thereby increasing protein abundance as compared to the translation initial rate for a corresponding wild-type RBS.

2. The genetically engineered microorganism of claim 1, wherein the enzyme increasing the availability of NADPH is PntAB.

3. The genetically engineered microorganism of claim 2, wherein the microorganism overexpresses PntAB, wherein the overexpression of PntAB is achieved by introducing a mutation into a promoter region of the gene encoding pntAB, optionally wherein the mutation of pntAB is a single-base pair substitution in the promoter region of pntAB.

4. The genetically engineered microorganism of claim 1 wherein the microorganism overexpresses FDH, wherein the overexpression of FDH is at least partly achieved by introducing a mutation into a 5' untranslated region of the gene encoding FDH, optionally wherein the mutation of fdh is a single-base pair substitution in the 5' untranslated region of fdh.

5. The genetically engineered microorganism of claim 1, wherein the microorganism is a bacterium, optionally a proteobacterium, wherein if the microorganism is a proteobacterium it is optionally an enterobacterium and wherein if the microorganism is an enterobacterium it is optionally *E. coli.*

6. The genetically engineered microorganism of claim 1, wherein the microorganism is capable of converting methanol to formate.

7. A method for growing the microorganism of claim 6, comprising contacting the microorganism under growth conditions comprising methanol as the sole carbon source.

8. The genetically engineered microorganism of claim 1, wherein the microorganism is capable of converting methane to formate.

9. A method for growing the microorganism of claim 8, comprising culturing the microorganism under growth conditions comprising methane as the sole carbon source.

10. The genetically engineered microorganism of claim 1, wherein the microorganism is capable of converting $CO_2$ to formate.

11. A method for growing the microorganism of claim 10, comprising culturing the microorganism under growth conditions with $CO_2$ as the sole carbon source.

12. A method for growing the microorganism of claim 1, comprising culturing the microorganism under growth conditions comprising formate as the sole carbon source.

* * * * *

SEQUENCE LISTING

<160> NUMBER OF SEQ ID NOS: 62

<210> SEQ ID NO 1
<211> LENGTH: 557
<212> TYPE: PRT
<213> ORGANISM: Methylobacterium extorquens
<220> FEATURE:
<223> OTHER INFORMATION: Formate-tetrahydrofolate ligase (EC:6.3.4.3)

<400> SEQUENCE: 1

Met Pro Ser Asp Ile Glu Ile Ala Arg Ala Ala Thr Leu Lys Pro Ile
1               5                   10                  15

Ala Gln Val Ala Glu Lys Leu Gly Ile Pro Asp Glu Ala Leu His Asn
            20                  25                  30

Tyr Gly Lys His Ile Ala Lys Ile Asp His Asp Phe Ile Ala Ser Leu
        35                  40                  45

Glu Gly Lys Pro Glu Gly Lys Leu Val Leu Val Thr Ala Ile Ser Pro
    50                  55                  60

Thr Pro Ala Gly Glu Gly Lys Thr Thr Thr Thr Val Gly Leu Gly Asp
65                  70                  75                  80

Ala Leu Asn Arg Ile Gly Lys Arg Ala Val Met Cys Leu Arg Glu Pro
                85                  90                  95

Ser Leu Gly Pro Cys Phe Gly Met Lys Gly Gly Ala Ala Gly Gly Gly
            100                 105                 110

Lys Ala Gln Val Val Pro Met Glu Gln Ile Asn Leu His Phe Thr Gly
        115                 120                 125

Asp Phe His Ala Ile Thr Ser Ala His Ser Leu Ala Ala Ala Leu Ile
        130                 135                 140

Asp Asn His Ile Tyr Trp Ala Asn Glu Leu Asn Ile Asp Val Arg Arg
145                 150                 155                 160

Ile His Trp Arg Arg Val Val Asp Met Asn Asp Arg Ala Leu Arg Ala
                165                 170                 175

Ile Asn Gln Ser Leu Gly Gly Val Ala Asn Gly Phe Pro Arg Glu Asp

-continued

```
                180               185               190

Gly Phe Asp Ile Thr Val Ala Ser Glu Val Met Ala Val Phe Cys Leu
            195               200               205

Ala Lys Asn Leu Ala Asp Leu Glu Glu Arg Leu Gly Arg Ile Val Ile
            210               215               220

Ala Glu Thr Arg Asp Arg Lys Pro Val Thr Leu Ala Asp Val Lys Ala
225               230               235               240

Thr Gly Ala Met Thr Val Leu Leu Lys Asp Ala Leu Gln Pro Asn Leu
                245               250               255

Val Gln Thr Leu Glu Gly Asn Pro Ala Leu Ile His Gly Gly Pro Phe
                260               265               270

Ala Asn Ile Ala His Gly Cys Asn Ser Val Ile Ala Thr Arg Thr Gly
                275               280               285

Leu Arg Leu Ala Asp Tyr Thr Val Thr Glu Ala Gly Phe Gly Ala Asp
            290               295               300

Leu Gly Ala Glu Lys Phe Ile Asp Ile Lys Cys Arg Gln Thr Gly Leu
305               310               315               320

Lys Pro Ser Ala Val Val Ile Val Ala Thr Ile Arg Ala Leu Lys Met
                325               330               335

His Gly Gly Val Asn Lys Lys Asp Leu Gln Ala Glu Asn Leu Asp Ala
                340               345               350

Leu Glu Lys Gly Phe Ala Asn Leu Glu Arg His Val Asn Asn Val Arg
            355               360               365

Ser Phe Gly Leu Pro Val Val Val Gly Val Asn His Phe Phe Gln Asp
            370               375               380

Thr Asp Ala Glu His Ala Arg Leu Lys Glu Leu Cys Arg Asp Arg Leu
385               390               395               400

Gln Val Glu Ala Ile Thr Cys Lys His Trp Ala Glu Gly Gly Ala Gly
                405               410               415

Ala Glu Ala Leu Ala Gln Ala Val Val Lys Leu Ala Glu Gly Glu Gln
                420               425               430

Lys Pro Leu Thr Phe Ala Tyr Glu Thr Glu Thr Lys Ile Thr Asp Lys
            435               440               445

Ile Lys Ala Ile Ala Thr Lys Leu Tyr Gly Ala Ala Asp Ile Gln Ile
            450               455               460

Glu Ser Lys Ala Ala Thr Lys Leu Ala Gly Phe Glu Lys Asp Gly Tyr
465               470               475               480

Gly Gly Leu Pro Val Cys Met Ala Lys Thr Gln Tyr Ser Phe Ser Thr
                485               490               495

Asp Pro Thr Leu Met Gly Ala Pro Ser Gly His Leu Val Ser Val Arg
                500               505               510

Asp Val Arg Leu Ser Ala Gly Ala Gly Phe Val Val Val Ile Cys Gly
            515               520               525

Glu Ile Met Thr Met Pro Gly Leu Pro Lys Val Pro Ala Ala Asp Thr
            530               535               540

Ile Arg Leu Asp Ala Asn Gly Gln Ile Asp Gly Leu Phe
545               550               555
```

```
<210> SEQ ID NO 2
<211> LENGTH: 1674
<212> TYPE: DNA
<213> ORGANISM: Methylobacterium extorquens
<220> FEATURE:
<223> OTHER INFORMATION: Formate-tetrahydrofolate ligase (EC:6.3.4.3)
```

```
<400> SEQUENCE: 2
atgccgtctg acatcgagat cgctcgtgct gctaccctga agccgatcgc tcaggttgct     60
gagaagctgg gtatcccgga cgaagctctg cacaactacg gtaaacacat cgctaaaatc    120
gaccacgact tcatcgcttc tctggaaggt aaaccggaag gtaaactggt tctggttacc    180
gctatctctc cgaccccggc tggtgaaggt aaaaccacca ccaccgttgg tctgggtgac    240
gctctgaacc gtatcggtaa acgtgctgtt atgtgcctgc gtgaaccgtc tctgggtccg    300
tgctttggta tgaagggtgg tgctgctggt ggtggtaaag ctcaggttgt tccgatggaa    360
cagatcaacc tgcacttcac cggtgacttc cacgctatca cctctgctca ctctctggct    420
gctgctctga tcgacaacca catctactgg gctaacgaac tgaacatcga cgtgcgtcgt    480
atccactggc gtcgtgttgt tgacatgaac gaccgtgctc tgcgtgctat caaccagtct    540
ctgggtggtg ttgctaacgg tttcccgcgt gaagacggtt ttgacatcac cgttgcttct    600
gaggttatgg ctgtgttctg cctggccaaa aacctggctg acctggaaga acgtctgggt    660
cgtatcgtta tcgctgagac ccgtgaccgt aaaccggtta ccctggctga cgttaaagct    720
accggtgcta tgaccgttct gctgaaggac gctctgcaac cgaacctggt tcagaccctg    780
gaaggtaacc cggctctgat ccacggtggt ccgtttgcta acatcgctca cggttgcaac    840
tctgttatcg ctacccgtac cggtctgcgt ctggctgact acaccgttac cgaagctggt    900
tttggtgcta acctgggtgc tgagaagttc atcgacatca aatgccgtca aactggtctg    960
aagccgtctg ctgttgttat cgttgctacc atccgtgctc tgaagatgca cggtggtgtt   1020
aacaaaaaag acctgcaagc tgagaacctg gacgctctgg agaagggttt tgctaacctg   1080
gaacgtcacg ttaacaacgt gcgttctttt ggtctgccgg ttgttgttgg tgttaaccac   1140
ttcttccagg acaccgacgc tgaacacgct cgtctgaagg aactgtgccg tgaccgtctg   1200
caagttgaag ctatcacctg caaacactgg gctgaaggtg gtgctggtgc tgaagctctg   1260
gctcaggctg ttgttaaact ggctgaaggt aacagaagc cgctgacctt gcttacgag     1320 accgagacca aaatcaccga caaaatcaaa gctatcgcta ccaaactgta cggtgctgct   1380
gacatccaga tcgaatctaa agctgctacc aaactggctg ttttgagaa ggacggttac    1440 ggtggcctgc cggtctgcat ggcaaaaacc cagtactctt tctctaccga cccgaccctg   1500
atgggtgctc cgtctggcca cctggtgagc gtgcgtgacg tgcgtctgtc tgctggtgct   1560
ggttttgttg ttgttatctg cggtgagatc atgaccatgc cgggtctgcc gaaggttccg   1620
gctgctgaca ccatccgtct ggacgctaac ggtcagatcg acggtctgtt ctaa         1674
```

```
<210> SEQ ID NO 3
<211> LENGTH: 208
<212> TYPE: PRT
<213> ORGANISM: Methylobacterium extorquens
<220> FEATURE:
<223> OTHER INFORMATION: Methenyltetrahydrofolate cyclohydrolase
      (EC:3.5.4.9)

<400> SEQUENCE: 3

Met Ala Gly Asn Glu Thr Ile Glu Thr Phe Leu Asp Gly Leu Ala Ser
1               5                   10                  15

Ser Ala Pro Thr Pro Gly Gly Gly Ala Ala Ala Ile Ser Gly Ala
            20                  25                  30

Met Gly Ala Ala Leu Val Ser Met Val Cys Asn Leu Thr Ile Gly Lys
        35                  40                  45

Lys Lys Tyr Val Glu Val Glu Ala Asp Leu Lys Gln Val Leu Glu Lys
```

```
          50                  55                  60

Ser Glu Gly Leu Arg Arg Thr Leu Thr Gly Met Ile Ala Asp Asp Val
65                  70                  75                  80

Glu Ala Phe Asp Ala Val Met Gly Ala Tyr Gly Leu Pro Lys Asn Thr
                85                  90                  95

Asp Glu Glu Lys Ala Ala Arg Ala Ala Lys Ile Gln Glu Ala Leu Lys
                100                 105                 110

Thr Ala Thr Asp Val Pro Leu Ala Cys Cys Arg Val Cys Arg Glu Val
            115                 120                 125

Ile Asp Leu Ala Glu Ile Val Ala Glu Lys Gly Asn Leu Asn Val Ile
        130                 135                 140

Ser Asp Ala Gly Val Ala Val Leu Ser Ala Tyr Ala Gly Leu Arg Ser
145                 150                 155                 160

Ala Ala Leu Asn Val Tyr Val Asn Ala Lys Gly Leu Asp Asp Arg Ala
                165                 170                 175

Phe Ala Glu Glu Arg Leu Lys Glu Leu Glu Gly Leu Leu Ala Glu Ala
                180                 185                 190

Gly Ala Leu Asn Glu Arg Ile Tyr Glu Thr Val Lys Ser Lys Val Asn
            195                 200                 205
```

```
<210> SEQ ID NO 4
<211> LENGTH: 627
<212> TYPE: DNA
<213> ORGANISM: Methylobacterium extorquens
<220> FEATURE:
<223> OTHER INFORMATION: Methenyltetrahydrofolate cyclohydrolase
      (EC:3.5.4.9)

<400> SEQUENCE: 4
atggctggta acgaaaccat cgaaaccttc ctggacggtc tggcttcttc tgctccgacc        60
ccgggtggtg gtggtgctgc tgctatctct ggtgctatgg gtgctgctct ggtttctatg       120
gtttgcaacc tgaccatcgg taaaaaaaaa tacgttgaag ttgaagctga cctgaaacag       180
gttctggaaa aatctgaagg tctgcgtcgt accctgaccg gtatgatcgc tgacgacgtt       240
gaagctttcg acgctgttat gggtgcttac ggtctgccga aaaacaccga cgaagaaaaa       300
gctgctcgtg ctgctaaaat ccaggaagct ctgaaaaccg ctaccgacgt tccgctggct       360
tgctgccgtg tttgccgtga agttatcgac ctggctgaaa tcgttgctga aaaaggtaac       420
ctgaacgtta tctctgacgc tggtgttgct gttctgtctg cttacgctgg tctgcgttct       480
gctgctctga acgtttacgt taacgctaaa ggtctggacg accgtgcttt cgctgaagaa       540
cgtctgaaag aactggaagg tctgctggct gaagctggtg ctctgaacga acgtatctac       600
gaaaccgtta atctaaagt taactaa                                            627
```

```
<210> SEQ ID NO 5
<211> LENGTH: 288
<212> TYPE: PRT
<213> ORGANISM: Methylobacterium extorquens
<220> FEATURE:
<223> OTHER INFORMATION: Methylenetetrahydrofolate dehydrogenase
      (EC:1.5.1.5)

<400> SEQUENCE: 5

Met Ser Lys Lys Leu Leu Phe Gln Phe Asp Thr Asp Ala Thr Pro Ser
1                   5                   10                  15

Val Phe Asp Val Val Val Gly Tyr Asp Gly Gly Ala Asp His Ile Thr
                20                  25                  30
```

```
Gly Tyr Gly Asn Val Thr Pro Asp Asn Val Gly Ala Tyr Val Asp Gly
        35                  40                  45

Thr Ile Tyr Thr Arg Gly Gly Lys Glu Lys Gln Ser Thr Ala Ile Phe
        50                  55                  60

Val Gly Gly Gly Asp Met Ala Ala Gly Glu Arg Val Phe Glu Ala Val
65                  70                  75                  80

Lys Lys Arg Phe Phe Gly Pro Phe Arg Val Ser Cys Met Leu Asp Ser
                85                  90                  95

Asn Gly Ser Asn Thr Thr Ala Ala Ala Gly Val Ala Leu Val Val Lys
                100                 105                 110

Ala Ala Gly Gly Ser Val Lys Gly Lys Lys Ala Val Val Leu Ala Gly
        115                 120                 125

Thr Gly Pro Val Gly Met Arg Ser Ala Ala Leu Leu Ala Gly Glu Gly
        130                 135                 140

Ala Glu Val Val Leu Cys Gly Arg Lys Leu Asp Lys Ala Gln Ala Ala
145                 150                 155                 160

Ala Asp Ser Val Asn Lys Arg Phe Lys Val Asn Val Thr Ala Ala Glu
                165                 170                 175

Thr Ala Asp Asp Ala Ser Arg Ala Glu Ala Val Lys Gly Ala His Phe
                180                 185                 190

Val Phe Thr Ala Gly Ala Ile Gly Leu Glu Leu Leu Pro Gln Ala Ala
        195                 200                 205

Trp Gln Asn Glu Ser Ser Ile Glu Ile Val Ala Asp Tyr Asn Ala Gln
        210                 215                 220

Pro Pro Leu Gly Ile Gly Gly Ile Asp Ala Thr Asp Lys Gly Lys Glu
225                 230                 235                 240

Tyr Gly Gly Lys Arg Ala Phe Gly Ala Leu Gly Ile Gly Gly Leu Lys
                245                 250                 255

Leu Lys Leu His Arg Ala Cys Ile Ala Lys Leu Phe Glu Ser Ser Glu
                260                 265                 270

Gly Val Phe Asp Ala Glu Glu Ile Tyr Lys Leu Ala Lys Glu Met Ala
        275                 280                 285
```

<210> SEQ ID NO 6
<211> LENGTH: 867
<212> TYPE: DNA
<213> ORGANISM: Methylobacterium extorquens
<220> FEATURE:
<223> OTHER INFORMATION: Methylenetetrahydrofolate dehydrogenase
      (EC:1.5.1.5)

<400> SEQUENCE: 6

```
atgtctaaaa aactgctgtt ccagttcgac accgacgcta ccccgtctgt tttcgacgtt      60
gttgttggtt acgacggtgg tgctgaccac atcaccggtt acggtaacgt taccccggac     120
aacgttggtg cttacgttga cggtaccatc tacacccgtg gtggtaaaga aaaacagtct     180
accgctatct tcgttggtgg tggtgacatg gctgctggtg aacgtgtttt cgaagctgtt     240
aaaaaacgtt tcttcggtcc gttccgtgtt tcttgcatgc tggactctaa cggttctaac     300
accaccgctg ctgctggtgt tgctctggtt gttaaagctg ctggtggttc tgttaaaggt     360
aaaaaagctg ttgttctggc tggtaccggt ccggttggta tgcgttctgc tgctctgctg     420
gctggtgaag tgctgaagt tgttctgtgc ggtcgtaaac tggacaaagc tcaggctgct     480
gctgactctt taacaaacg tttcaaagtt aacgttaccg ctgctgaaac cgctgacgac     540
gcttctcgtg ctgaagctgt taaaggtgct cacttcgttt tcaccgctgg tgctatcggt     600
```

```
ctggaactgc tgccgcaggc tgcttggcag aacgaatctt ctatcgaaat cgttgctgac     660
tacaacgctc agccgccgct gggtatcggt ggtatcgacg ctaccgacaa aggtaaagaa     720
tacggtggta acgtgctttt cggtgctctg ggtatcggtg tctgaaact gaaactgcac     780 cgtgcttgca tcgctaaact gttcgaatct tctgaaggtg ttttcgacgc tgaagaaatc     840
tacaaactgg ctaaagaaat ggcttaa                                         867
```

```
<210> SEQ ID NO 7
<211> LENGTH: 364
<212> TYPE: PRT
<213> ORGANISM: Escherichia coli
<220> FEATURE:
<223> OTHER INFORMATION: Aminomethyltransferase (EC:2.2.2.10)

<400> SEQUENCE: 7

Met Ala Gln Gln Thr Pro Leu Tyr Glu Gln His Thr Leu Cys Gly Ala
1               5                   10                  15

Arg Met Val Asp Phe His Gly Trp Met Met Pro Leu His Tyr Gly Ser
                20                  25                  30

Gln Ile Asp Glu His His Ala Val Arg Thr Asp Ala Gly Met Phe Asp
            35                  40                  45

Val Ser His Met Thr Ile Val Asp Leu Arg Gly Ser Arg Thr Arg Glu
        50                  55                  60

Phe Leu Arg Tyr Leu Leu Ala Asn Asp Val Ala Lys Leu Thr Lys Ser
65                  70                  75                  80

Gly Lys Ala Leu Tyr Ser Gly Met Leu Asn Ala Ser Gly Gly Val Ile
                85                  90                  95

Asp Asp Leu Ile Val Tyr Tyr Phe Thr Glu Asp Phe Phe Arg Leu Val
            100                 105                 110

Val Asn Ser Ala Thr Arg Glu Lys Asp Leu Ser Trp Ile Thr Gln His
        115                 120                 125

Ala Glu Pro Phe Gly Ile Glu Ile Thr Val Arg Asp Asp Leu Ser Met
        130                 135                 140

Ile Ala Val Gln Gly Pro Asn Ala Gln Ala Lys Ala Ala Thr Leu Phe
145                 150                 155                 160

Asn Asp Ala Gln Arg Gln Ala Val Glu Gly Met Lys Pro Phe Phe Gly
                165                 170                 175

Val Gln Ala Gly Asp Leu Phe Ile Ala Thr Thr Gly Tyr Thr Gly Glu
            180                 185                 190

Ala Gly Tyr Glu Ile Ala Leu Pro Asn Glu Lys Ala Ala Asp Phe Trp
            195                 200                 205

Arg Ala Leu Val Glu Ala Gly Val Lys Pro Cys Gly Leu Gly Ala Arg
        210                 215                 220

Asp Thr Leu Arg Leu Glu Ala Gly Met Asn Leu Tyr Gly Gln Glu Met
225                 230                 235                 240

Asp Glu Thr Ile Ser Pro Leu Ala Ala Asn Met Gly Trp Thr Ile Ala
                245                 250                 255

Trp Glu Pro Ala Asp Arg Asp Phe Ile Gly Arg Glu Ala Leu Glu Val
            260                 265                 270

Gln Arg Glu His Gly Thr Glu Lys Leu Val Gly Leu Val Met Thr Glu
        275                 280                 285

Lys Gly Val Leu Arg Asn Glu Leu Pro Val Arg Phe Thr Asp Ala Gln
    290                 295                 300

Gly Asn Gln His Glu Gly Ile Ile Thr Ser Gly Thr Phe Ser Pro Thr
305                 310                 315                 320
```

-continued

Leu Gly Tyr Ser Ile Ala Leu Ala Arg Val Pro Glu Gly Ile Gly Glu
            325                 330                 335

Thr Ala Ile Val Gln Ile Arg Asn Arg Glu Met Pro Val Lys Val Thr
            340                 345                 350

Lys Pro Val Phe Val Arg Asn Gly Lys Ala Val Ala
            355                 360

<210> SEQ ID NO 8
<211> LENGTH: 1095
<212> TYPE: DNA
<213> ORGANISM: Escherichia coli
<220> FEATURE:
<223> OTHER INFORMATION: Aminomethyltransferase (EC:2.2.2.10)

<400> SEQUENCE: 8
atggcacaac agactccttt gtacgaacaa cacacgcttt gcggcgctcg catggtggat        60
ttccacggct ggatgatgcc gctgcattac ggttcgcaaa tcgacgaaca tcatgcggta       120
cgtaccgatg ccggaatgtt tgatgtgtca catatgacca tcgtcgatct tcgcggcagc       180
cgcacccggg agtttctgcg ttatctgctg gcgaacgatg tggcgaagct caccaaaagc       240
ggcaaagccc tttactcggg gatgttgaat gcctctggcg gtgtgataga tgacctcatc       300
gtctactact ttactgaaga tttcttccgc ctcgttgtta actccgccac ccgcgaaaaa       360
gacctctcct ggattaccca cacgctgaa cctttcggca tcgaaattac cgttcgtgat        420
gacctttcca tgattgccgt gcaagggccg aatgcgcagg caaaagctgc cacactgttt       480
aatgacgccc agcgtcaggc ggtggaaggg atgaaaccgt tctttggcgt gcaggcgggc       540
gatctgttta ttgccaccac tggttatacc ggtgaagcgg gctatgaaat tgcgctgccc       600
aatgaaaaag cggccgattt ctggcgtgcg ctggtggaag cggtgttaa gccatgtggc        660 ttgggcgcgc gtgacacgct gcgtctggaa gcgggcatga atctttatgg tcaggagatg       720
gacgaaacca tctctccttt agccgccaac atgggctgga ccatcgcctg gaaccggca        780 gatcgtgact ttatcggtcg tgaagccctg gaagtgcagc gtgagcatgg tacagaaaaa       840
ctggttggtc tggtgatgac cgaaaaaggc gtgctgcgta tgaactgcc ggtacgcttt        900 accgatgcgc agggcaacca gcatgaaggc attatcacca gcggtacttt ctccccgacg       960
ctgggttaca gcattgcgct ggcgcgcgtg ccggaaggta ttggcgaaac ggcgattgtg      1020
caaattcgca accgtgaaat gccggttaaa gtgacaaaac tgttttttgt gcgtaacggc      1080
aaagccgtcg cgtga                                                       1095

<210> SEQ ID NO 9
<211> LENGTH: 129
<212> TYPE: PRT
<213> ORGANISM: Escherichia coli
<220> FEATURE:
<223> OTHER INFORMATION: Glycine cleavage system H protein

<400> SEQUENCE: 9

Met Ser Asn Val Pro Ala Glu Leu Lys Tyr Ser Lys Glu His Glu Trp
1               5                  10                  15

Leu Arg Lys Glu Ala Asp Gly Thr Tyr Thr Val Gly Ile Thr Glu His
            20                  25                  30

Ala Gln Glu Leu Leu Gly Asp Met Val Phe Val Asp Leu Pro Glu Val
        35                  40                  45

Gly Ala Thr Val Ser Ala Gly Asp Asp Cys Ala Val Ala Glu Ser Val
    50                  55                  60

-continued

```
Lys Ala Ala Ser Asp Ile Tyr Ala Pro Val Ser Gly Glu Ile Val Ala
65                  70                  75                  80

Val Asn Asp Ala Leu Ser Asp Ser Pro Glu Leu Val Asn Ser Glu Pro
                85                  90                  95

Tyr Ala Gly Gly Trp Ile Phe Lys Ile Lys Ala Ser Asp Glu Ser Glu
            100                 105                 110

Leu Glu Ser Leu Leu Asp Ala Thr Ala Tyr Glu Ala Leu Leu Glu Asp
        115                 120                 125

Glu

<210> SEQ ID NO 10
<211> LENGTH: 390
<212> TYPE: DNA
<213> ORGANISM: Escherichia coli
<220> FEATURE:
<223> OTHER INFORMATION: Glycine cleavage system H protein

<400> SEQUENCE: 10
atgagcaacg taccagcaga actgaaatac agcaaagaac acgaatggct gcgtaaagaa        60
gccgacggca cttacaccgt tggtattacc gaacatgctc aggagctgtt aggcgatatg       120
gtgtttgttg acctgccgga agtgggcgca acggttagcg cgggcgatga ctgcgcggtt       180
gccgaatcgg taaaagcggc gtcagacatt tatgcgccag taagcggtga atcgtggcg        240 gtaaacgacg cactgagcga ttccccggaa ctggtgaaca gcgaaccgta tgcaggcggc       300
tggatcttta aaatcaaagc cagcgatgaa agcgaactgg aatcactgct ggatgcgacc       360
gcatacgaag cattgttaga agacgagtaa                                        390

<210> SEQ ID NO 11
<211> LENGTH: 957
<212> TYPE: PRT
<213> ORGANISM: Escherichia coli
<220> FEATURE:
<223> OTHER INFORMATION: Glycine dehydrogenase (decarboxylating)
      (EC:1.4.4.2)

<400> SEQUENCE: 11

Met Thr Gln Thr Leu Ser Gln Leu Glu Asn Ser Gly Ala Phe Ile Glu
1               5                   10                  15

Arg His Ile Gly Pro Asp Ala Ala Gln Gln Gln Glu Met Leu Asn Ala
            20                  25                  30

Val Gly Ala Gln Ser Leu Asn Ala Leu Thr Gly Gln Ile Val Pro Lys
        35                  40                  45

Asp Ile Gln Leu Ala Thr Pro Pro Gln Val Gly Ala Pro Ala Thr Glu
    50                  55                  60

Tyr Ala Ala Leu Ala Glu Leu Lys Ala Ile Ala Ser Arg Asn Lys Arg
65                  70                  75                  80

Phe Thr Ser Tyr Ile Gly Met Gly Tyr Thr Ala Val Gln Leu Pro Pro
                85                  90                  95

Val Ile Leu Arg Asn Met Leu Glu Asn Pro Gly Trp Tyr Thr Ala Tyr
            100                 105                 110

Thr Pro Tyr Gln Pro Glu Val Ser Gln Gly Arg Leu Glu Ala Leu Leu
        115                 120                 125

Asn Phe Gln Gln Val Thr Leu Asp Leu Thr Gly Leu Asp Met Ala Ser
    130                 135                 140

Ala Ser Leu Leu Asp Glu Ala Thr Ala Ala Ala Glu Ala Met Ala Met
145                 150                 155                 160
```

-continued

```
Ala Lys Arg Val Ser Lys Leu Lys Asn Ala Asn Arg Phe Phe Val Ala
            165             170             175

Ser Asp Val His Pro Gln Thr Leu Asp Val Val Arg Thr Arg Ala Glu
            180             185             190

Thr Phe Gly Phe Glu Val Ile Val Asp Asp Ala Gln Lys Val Leu Asp
            195             200             205

His Gln Asp Val Phe Gly Val Leu Leu Gln Gln Val Gly Thr Thr Gly
    210             215             220

Glu Ile His Asp Tyr Thr Ala Leu Ile Ser Glu Leu Lys Ser Arg Lys
225             230             235             240

Ile Val Val Ser Val Ala Ala Asp Ile Met Ala Leu Val Leu Leu Thr
            245             250             255

Ala Pro Gly Lys Gln Gly Ala Asp Ile Val Phe Gly Ser Ala Gln Arg
            260             265             270

Phe Gly Val Pro Met Gly Tyr Gly Gly Pro His Ala Ala Phe Phe Ala
            275             280             285

Ala Lys Asp Glu Tyr Lys Arg Ser Met Pro Gly Arg Ile Ile Gly Val
    290             295             300

Ser Lys Asp Ala Ala Gly Asn Thr Ala Leu Arg Met Ala Met Gln Thr
305             310             315             320

Arg Glu Gln His Ile Arg Arg Glu Lys Ala Asn Ser Asn Ile Cys Thr
            325             330             335

Ser Gln Val Leu Leu Ala Asn Ile Ala Ser Leu Tyr Ala Val Tyr His
            340             345             350

Gly Pro Val Gly Leu Lys Arg Ile Ala Asn Arg Ile His Arg Leu Thr
            355             360             365

Asp Ile Leu Ala Ala Gly Leu Gln Gln Lys Gly Leu Lys Leu Arg His
    370             375             380

Ala His Tyr Phe Asp Thr Leu Cys Val Glu Val Ala Asp Lys Ala Gly
385             390             395             400

Val Leu Thr Arg Ala Glu Ala Ala Glu Ile Asn Leu Arg Ser Asp Ile
            405             410             415

Leu Asn Ala Val Gly Ile Thr Leu Asp Glu Thr Thr Thr Arg Glu Asn
            420             425             430

Val Met Gln Leu Phe Asn Val Leu Leu Gly Asp Asn His Gly Leu Asp
            435             440             445

Ile Asp Thr Leu Asp Lys Asp Val Ala His Asp Ser Arg Ser Ile Gln
    450             455             460

Pro Ala Met Leu Arg Asp Asp Glu Ile Leu Thr His Pro Val Phe Asn
465             470             475             480

Arg Tyr His Ser Glu Thr Glu Met Met Arg Tyr Met His Ser Leu Glu
            485             490             495

Arg Lys Asp Leu Ala Leu Asn Gln Ala Met Ile Pro Leu Gly Ser Cys
            500             505             510

Thr Met Lys Leu Asn Ala Ala Ala Glu Met Ile Pro Ile Thr Trp Pro
            515             520             525

Glu Phe Ala Glu Leu His Pro Phe Cys Pro Glu Gln Ala Glu Gly
            530             535             540

Tyr Gln Gln Met Ile Ala Gln Leu Ala Asp Trp Leu Val Lys Leu Thr
545             550             555             560

Gly Tyr Asp Ala Val Cys Met Gln Pro Asn Ser Gly Ala Gln Gly Glu
            565             570             575
```

```
Tyr Ala Gly Leu Leu Ala Ile Arg His Tyr His Glu Ser Arg Asn Glu
                580                 585                 590

Gly His Arg Asp Ile Cys Leu Ile Pro Ala Ser Ala His Gly Thr Asn
        595                 600                 605

Pro Ala Ser Ala His Met Ala Gly Met Gln Val Val Val Val Ala Cys
        610                 615                 620

Asp Lys Asn Gly Asn Ile Asp Leu Thr Asp Leu Arg Ala Lys Ala Glu
625                 630                 635                 640

Gln Ala Gly Asp Asn Leu Ser Cys Ile Met Val Thr Tyr Pro Ser Thr
                645                 650                 655

His Gly Val Tyr Glu Glu Thr Ile Arg Glu Val Cys Glu Val Val His
                660                 665                 670

Gln Phe Gly Gly Gln Val Tyr Leu Asp Gly Ala Asn Met Asn Ala Gln
        675                 680                 685

Val Gly Ile Thr Ser Pro Gly Phe Ile Gly Ala Asp Val Ser His Leu
        690                 695                 700

Asn Leu His Lys Thr Phe Cys Ile Pro His Gly Gly Gly Gly Pro Gly
705                 710                 715                 720

Met Gly Pro Ile Gly Val Lys Ala His Leu Ala Pro Phe Val Pro Gly
                725                 730                 735

His Ser Val Val Gln Ile Glu Gly Met Leu Thr Arg Gln Gly Ala Val
                740                 745                 750

Ser Ala Ala Pro Phe Gly Ser Ala Ser Ile Leu Pro Ile Ser Trp Met
        755                 760                 765

Tyr Ile Arg Met Met Gly Ala Glu Gly Leu Lys Lys Ala Ser Gln Val
        770                 775                 780

Ala Ile Leu Asn Ala Asn Tyr Ile Ala Ser Arg Leu Gln Asp Ala Phe
785                 790                 795                 800

Pro Val Leu Tyr Thr Gly Arg Asp Gly Arg Val Ala His Glu Cys Ile
                805                 810                 815

Leu Asp Ile Arg Pro Leu Lys Glu Glu Thr Gly Ile Ser Glu Leu Asp
                820                 825                 830

Ile Ala Lys Arg Leu Ile Asp Tyr Gly Phe His Ala Pro Thr Met Ser
        835                 840                 845

Phe Pro Val Ala Gly Thr Leu Met Val Glu Pro Thr Glu Ser Glu Ser
        850                 855                 860

Lys Val Glu Leu Asp Arg Phe Ile Asp Ala Met Leu Ala Ile Arg Ala
865                 870                 875                 880

Glu Ile Asp Gln Val Lys Ala Gly Val Trp Pro Leu Glu Asp Asn Pro
                885                 890                 895

Leu Val Asn Ala Pro His Ile Gln Ser Glu Leu Val Ala Glu Trp Ala
                900                 905                 910

His Pro Tyr Ser Arg Glu Val Ala Val Phe Pro Ala Gly Val Ala Asp
        915                 920                 925

Lys Tyr Trp Pro Thr Val Lys Arg Leu Asp Asp Val Tyr Gly Asp Arg
        930                 935                 940

Asn Leu Phe Cys Ser Cys Val Pro Ile Ser Glu Tyr Gln
945                 950                 955
```

```
<210> SEQ ID NO 12
<211> LENGTH: 2874
<212> TYPE: DNA
<213> ORGANISM: Escherichia coli
<220> FEATURE:
<223> OTHER INFORMATION: Glycine dehydrogenase (decarboxylating)
```

-continued (EC:1.4.4.2)

<400> SEQUENCE: 12

```
atgacacaga cgttaagcca gcttgaaaac agcggcgctt ttattgaacg ccatatcgga        60
ccggacgccg cgcaacagca agaaatgctg aatgccgttg gtgcacaatc gttaaacgcg       120
ctgaccggcc agattgtgcc gaaagatatt caacttgcga caccaccgca ggttggcgca       180
ccggcgaccg aatacgccgc actggcagaa ctcaaggcta ttgccagtcg caataaacgc       240
ttcacgtctt acatcggcat gggttacacc gccgtgcagc taccgccggt tatcctgcgt       300
aacatgctgg aaaatccggg ctggtatacc gcgtacactc cgtatcaacc tgaagtctcc       360
cagggccgcc ttgaagcact gctcaacttc cagcaggtaa cgctggattt gactggactg       420
gatatggcct ctgcttctct tctggacgag gccaccgctg ccgccgaagc aatggccgatg      480 gcgaaacgcg tcagcaaact gaaaaatgcc aaccgcttct tcgtggcttc cgatgtgcat       540
ccgcaaacgc tggatgtggt ccgtactcgt gccgaaacct ttggttttga agtgattgtc       600
gatgacgcgc aaaaagtgct cgaccatcag gacgtcttcg gcgtgctgtt acagcaggta       660
ggcactaccg gtgaaattca cgactacact gcgcttatta gcgaactgaa atcacgcaaa       720
attgtggtca gcgttgccgc cgatattatg gcgctggtgc tgttaactgc gccgggtaaa       780
cagggcgcgg atattgtttt tggttcggcg caacgcttcg gcgtgccgat gggctacggt       840
ggcccacacg cggcattctt tgcggcgaaa gatgaataca aacgctcaat gccgggccgt       900
attatcggtg tatcgaaaga tgcagctggc aataccgcgc tgcgcatggc gatgcagact       960
cgcgagcaac atatccgccg tgagaaagcg aactccaaca tttgtacttc ccaggtactg      1020
ctggcaaaca tcgccagcct gtatgccgtt tatcacggcc cggttggcct gaaacgtatc      1080
gctaaccgca ttcaccgtct gaccgatatc ctggcggcgg gcctgcaaca aaaaggtctg      1140
aaactgcgcc atgcgcacta tttcgacacc ttgtgtgtgg aagtggccga caaagcgggc      1200
gtactgacgc gtgccgaagc ggctgaaatc aacctgcgta gcgatattct gaacgcggtt      1260
gggatcaccc ttgatgaaac aaccacgcgt gaaaacgtaa tgcagctttt caacgtgctg      1320
ctgggcgata accacggcct ggacatcgac acgctggaca aagacgtggc tcacgacagc      1380
cgctctatcc agcctgcgat gctgcgcgac gacgaaatcc tcacccatcc ggtgtttaat      1440
cgctaccaca gcgaaaccga aatgatgcgc tatatgcact cgctggagcg taaagatctg      1500
gcgctgaatc aggcgatgat cccgctgggt tcctgcacca tgaaactgaa cgccgccgcc      1560
gagatgatcc caatcacctg gccggaattt gccgaactgc acccgttctg cccgccggag      1620
caggccgaag gttatcagca gatgattgcg cagctggctg actggctggt gaaactgacc      1680
ggttacgacg ccgtttgtat gcagccgaac tctggcgcac agggcgaata cgcgggcctg      1740
ctggcgattc gtcattatca tgaaagccgc aacgaagggc atcgcgatat ctgcctgatc      1800
ccggcttctg cgcacggaac taaccccgct tctgcacata tggcaggaat gcaggtggtg      1860
gttgtggcgt gtgataaaaa cggcaacatc gatctgactg atctgcgcgc gaaagcggaa      1920
caggcgggcg ataacctctc ctgtatcatg gtgacttatc cttctaccca cggcgtgtat      1980
gaagaaacga tccgtgaagt gtgtgaagtc gtgcatcagt cggcggtca ggtttacctt       2040 gatggcgcga acatgaacgc ccaggttggc atcacctcgc cgggctttat tggtgcggac      2100
gtttcacacc ttaacctaca taaaacttc tgcattccgc acggcggtgg tggtccgggt       2160
atgggaccga tcggcgtgaa agcgcatttg gcaccgtttg taccgggtca tagcgtggtg      2220
caaatcgaag gcatgttaac ccgtcagggc gcggtttctg cggcaccgtt cggtagcgcc      2280
```

-continued

```
tctatcctgc caatcagctg gatgtacatc cgcatgatgg gcgcagaagg gctgaaaaaa   2340
gcaagccagg tggcaatcct caacgccaac tatattgcca gccgcctgca ggatgccttc   2400
ccggtgctgt ataccggtcg cgacggtcgc gtggcgcacg aatgtattct cgatattcgc   2460
ccgctgaaag aagaaaccgg catcagcgag ctggatattg ccaagcgcct gatcgactac   2520
ggtttccacg cgccgacgat gtcgttcccg gtggcgggta cgctgatggt tgaaccgact   2580
gaatctgaaa gcaaagtgga actggatcgc tttatcgacg cgatgctggc tatccgcgca   2640
gaaattgacc aggtgaaagc cggtgtctgg ccgctggaag ataacccgct ggtgaacgcg   2700
ccgcacattc agagcgaact ggtcgccgag tgggcgcatc cgtacagccg tgaagttgcg   2760
gtattcccgg caggtgtggc agacaaatac tggccgacag tgaaacgtct ggatgatgtt   2820
tacggcgacc gtaacctgtt ctgctcctgc gtaccgatta cgaataccagtaa         2874
```

<210> SEQ ID NO 13
<211> LENGTH: 454
<212> TYPE: PRT
<213> ORGANISM: Escherichia coli
<220> FEATURE:
<223> OTHER INFORMATION: L-serine dehydratase 1 (EC:4.3.1.17)

<400> SEQUENCE: 13

```
Met Ile Ser Leu Phe Asp Met Phe Lys Val Gly Ile Gly Pro Ser Ser
1               5                   10                  15

Ser His Thr Val Gly Pro Met Lys Ala Gly Lys Gln Phe Val Asp Asp
                20                  25                  30

Leu Val Glu Lys Gly Leu Leu Asp Ser Val Thr Arg Val Ala Val Asp
            35                  40                  45

Val Tyr Gly Ser Leu Ser Leu Thr Gly Lys Gly His His Thr Asp Ile
        50                  55                  60

Ala Ile Ile Met Gly Leu Ala Gly Asn Glu Pro Ala Thr Val Asp Ile
65                  70                  75                  80

Asp Ser Ile Pro Gly Phe Ile Arg Asp Val Glu Glu Arg Glu Arg Leu
                85                  90                  95

Leu Leu Ala Gln Gly Arg His Glu Val Asp Phe Pro Arg Asp Asn Gly
            100                 105                 110

Met Arg Phe His Asn Gly Asn Leu Pro Leu His Glu Asn Gly Met Gln
        115                 120                 125

Ile His Ala Tyr Asn Gly Asp Glu Val Val Tyr Ser Lys Thr Tyr Tyr
    130                 135                 140

Ser Ile Gly Gly Gly Phe Ile Val Asp Glu Glu His Phe Gly Gln Asp
145                 150                 155                 160

Ala Ala Asn Glu Val Ser Val Pro Tyr Pro Phe Lys Ser Ala Thr Glu
                165                 170                 175

Leu Leu Ala Tyr Cys Asn Glu Thr Gly Tyr Ser Leu Ser Gly Leu Ala
            180                 185                 190

Met Gln Asn Glu Leu Ala Leu His Ser Lys Lys Glu Ile Asp Glu Tyr
        195                 200                 205

Phe Ala His Val Trp Gln Thr Met Gln Ala Cys Ile Asp Arg Gly Met
    210                 215                 220

Asn Thr Glu Gly Val Leu Pro Gly Pro Leu Arg Val Pro Arg Arg Ala
225                 230                 235                 240

Ser Ala Leu Arg Arg Met Leu Val Ser Ser Asp Lys Leu Ser Asn Asp
                245                 250                 255
```

-continued

```
Pro Met Asn Val Ile Asp Trp Val Asn Met Phe Ala Leu Ala Val Asn
        260             265             270
```

```
Glu Glu Asn Ala Ala Gly Gly Arg Val Val Thr Ala Pro Thr Asn Gly
        275             280             285
```

```
Ala Cys Gly Ile Val Pro Ala Val Leu Ala Tyr Tyr Asp His Phe Ile
        290             295             300
```

```
Glu Ser Val Ser Pro Asp Ile Tyr Thr Arg Tyr Phe Met Ala Ala Gly
305             310             315             320
```

```
Ala Ile Gly Ala Leu Tyr Lys Met Asn Ala Ser Ile Ser Gly Ala Glu
                325             330             335
```

```
Val Gly Cys Gln Gly Glu Val Gly Val Ala Cys Ser Met Ala Ala Ala
        340             345             350
```

```
Gly Leu Ala Glu Leu Leu Gly Gly Ser Pro Glu Gln Val Cys Val Ala
        355             360             365
```

```
Ala Glu Ile Gly Met Glu His Asn Leu Gly Leu Thr Cys Asp Pro Val
        370             375             380
```

```
Ala Gly Gln Val Gln Val Pro Cys Ile Glu Arg Asn Ala Ile Ala Ser
385             390             395             400
```

```
Val Lys Ala Ile Asn Ala Ala Arg Met Ala Leu Arg Arg Thr Ser Ala
                405             410             415
```

```
Pro Arg Val Ser Leu Asp Lys Val Ile Glu Thr Met Tyr Glu Thr Gly
                420             425             430
```

```
Lys Asp Met Asn Ala Lys Tyr Arg Glu Thr Ser Arg Gly Gly Leu Ala
                435             440             445
```

```
Ile Lys Val Gln Cys Asp
        450
```

```
<210> SEQ ID NO 14
<211> LENGTH: 1365
<212> TYPE: DNA
<213> ORGANISM: Escherichia coli
<220> FEATURE:
<223> OTHER INFORMATION: L-serine dehydratase 1 (EC:4.3.1.17)

<400> SEQUENCE: 14
gtgattagtc tattcgacat gtttaaggtg gggattggtc cctcatcttc ccataccgta        60
gggcctatga aggcaggtaa acagttcgtc gatgatctgg tcgaaaaagg cttactggat       120
agcgttactc gcgttgccgt ggacgtttat ggttcactgt cgctgacggg taaaggccac       180
cacaccgata tcgccattat tatgggtctt gcaggtaacg aacctgccac cgtggatatc       240
gacagtattc ccggttttat tcgcgacgta gaagagcgcg aacgtctgct gctggcacag       300
ggacggcatg aagtggattt cccgcgcgac aacgggatgc gttttcataa cggcaacctg       360
ccgctgcatg aaaacggtat gcaaatccac gcctataacg cgatgaagt cgtctacagc        420 aaaacttatt attccatcgg cggcggtttt atcgtcgatg aagaacactt tggtcaggat       480
gctgccaacg aagtaagcgt gccgtatccg ttcaaatctg ccaccgaact gctcgcgtac       540
tgtaatgaaa ccggctattc gctgtctggt ctcgctatgc agaacgaact ggcgctgcac       600
agcaagaaag agatcgacga gtatttcgcg catgtctggc aaaccatgca ggcatgtatc       660
gatcgcggga tgaacaccga aggtgtactg ccaggcccgc tgcgcgtgcc acgtcgtgcg       720
tctgccctgc gccggatgct ggtttccagc gataaactgt ctaacgatcc gatgaatgtc       780
attgactggg taaacatgtt tgcgctggca gttaacgaag aaaacgccgc cggtggtcgt       840
gtggtaactg cgccaaccaa cggtgcctgc ggtatcgttc cggcagtgct ggcttactat       900
```

-continued

```
gaccacttta ttgaatcggt cagcccggac atctataccc gttactttat ggcagcgggc       960
gcgattggtg cattgtataa aatgaacgcc tctatttccg gtgcggaagt tggttgccag      1020
ggcgaagtgg gtgttgcctg ttcaatggct gctgcgggtc ttgcagaact gctgggcggt      1080
agcccggaac aggtttgcgt ggcggcgaa attggcatgg aacacaacct tggtttaacc      1140
tgcgacccgg ttgcagggca ggttcaggtg ccgtgcattg agcgtaatgc cattgcctct      1200
gtgaaggcga ttaacgccgc gcggatggct ctgcgccgca ccagtgcacc gcgcgtctcg      1260
ctggataagg tcatcgaaac gatgtacgaa accggtaagg acatgaacgc caaataccgc      1320
gaaacctcac gcggtggtct ggcaatcaaa gtccagtgtg actaa                      1365
```

<210> SEQ ID NO 15
<211> LENGTH: 417
<212> TYPE: PRT
<213> ORGANISM: Escherichia coli
<220> FEATURE:
<223> OTHER INFORMATION: serine hydroxymethyltransferase

<400> SEQUENCE: 15

```
Met Leu Lys Arg Glu Met Asn Ile Ala Asp Tyr Asp Ala Glu Leu Trp
1               5                   10                  15

Gln Ala Met Glu Gln Glu Lys Val Arg Gln Glu Glu His Ile Glu Leu
            20                  25                  30

Ile Ala Ser Glu Asn Tyr Thr Ser Pro Arg Val Met Gln Ala Gln Gly
        35                  40                  45

Ser Gln Leu Thr Asn Lys Tyr Ala Glu Gly Tyr Pro Gly Lys Arg Tyr
    50                  55                  60

Tyr Gly Gly Cys Glu Tyr Val Asp Ile Val Glu Gln Leu Ala Ile Asp
65                  70                  75                  80

Arg Ala Lys Glu Leu Phe Gly Ala Asp Tyr Ala Asn Val Gln Pro His
                85                  90                  95

Ser Gly Ser Gln Ala Asn Phe Ala Val Tyr Thr Ala Leu Leu Glu Pro
            100                 105                 110

Gly Asp Thr Val Leu Gly Met Asn Leu Ala His Gly Gly His Leu Thr
        115                 120                 125

His Gly Ser Pro Val Asn Phe Ser Gly Lys Leu Tyr Asn Ile Val Pro
    130                 135                 140

Tyr Gly Ile Asp Ala Thr Gly His Ile Asp Tyr Ala Asp Leu Glu Lys
145                 150                 155                 160

Gln Ala Lys Glu His Lys Pro Lys Met Ile Ile Gly Gly Phe Ser Ala
                165                 170                 175

Tyr Ser Gly Val Val Asp Trp Ala Lys Met Arg Glu Ile Ala Asp Ser
            180                 185                 190

Ile Gly Ala Tyr Leu Phe Val Asp Met Ala His Val Ala Gly Leu Val
        195                 200                 205

Ala Ala Gly Val Tyr Pro Asn Pro Val Pro His Ala His Val Val Thr
    210                 215                 220

Thr Thr Thr His Lys Thr Leu Ala Gly Pro Arg Gly Gly Leu Ile Leu
225                 230                 235                 240

Ala Lys Gly Gly Ser Glu Glu Leu Tyr Lys Lys Leu Asn Ser Ala Val
                245                 250                 255

Phe Pro Gly Gly Gln Gly Gly Pro Leu Met His Val Ile Ala Gly Lys
            260                 265                 270

Ala Val Ala Leu Lys Glu Ala Met Glu Pro Glu Phe Lys Thr Tyr Gln
        275                 280                 285
```

```
Gln Gln Val Ala Lys Asn Ala Lys Ala Met Val Glu Val Phe Leu Glu
    290                 295                 300

Arg Gly Tyr Lys Val Val Ser Gly Gly Thr Asp Asn His Leu Phe Leu
305                 310                 315                 320

Val Asp Leu Val Asp Lys Asn Leu Thr Gly Lys Glu Ala Asp Ala Ala
                325                 330                 335

Leu Gly Arg Ala Asn Ile Thr Val Asn Lys Asn Ser Val Pro Asn Asp
            340                 345                 350

Pro Lys Ser Pro Phe Val Thr Ser Gly Ile Arg Val Gly Thr Pro Ala
            355                 360                 365

Ile Thr Arg Arg Gly Phe Lys Glu Ala Glu Ala Lys Glu Leu Ala Gly
    370                 375                 380

Trp Met Cys Asp Val Leu Asp Ser Ile Asn Asp Glu Ala Val Ile Glu
385                 390                 395                 400

Arg Ile Lys Gly Lys Val Leu Asp Ile Cys Ala Arg Tyr Pro Val Tyr
            405                 410                 415

Ala
```

<210> SEQ ID NO 16
<211> LENGTH: 1254
<212> TYPE: DNA
<213> ORGANISM: Escherichia coli
<220> FEATURE:
<223> OTHER INFORMATION: serine hydroxymethyltransferase

<400> SEQUENCE: 16

```
atgttaaagc gtgaaatgaa cattgccgat tatgatgccg aactgtggca ggctatggag      60
caggaaaaag tacgtcagga agagcacatc gaactgatcg cctccgaaaa ctacaccagc     120
ccgcgcgtaa tgcaggcgca gggttctcag ctgaccaaca aatatgctga aggttatccg     180
ggcaaacgct actacggcgg ttgcgagtat gttgatatcg ttgaacaact ggcgatcgat     240
cgtgcgaaag aactgttcgg cgctgactac gctaacgtcc agccgcactc cggctcccag     300
gctaactttg cggtctacac cgcgctgctg aaccaggtg ataccgttct gggtatgaac     360
ctggcgcatg gcggtcacct gactcacggt tctccggtta acttctccgg taaactgtac     420
aacatcgttc cttacggtat cgatgctacc ggtcatatcg actacgccga tctggaaaaa     480
caagccaaag aacacaagcc gaaaatgatt atcggtggtt tctctgcata ttccggcgtg     540
gtggactggg cgaaaatgcg tgaaatcgct gacagcatcg gtgcttacct gttcgttgat     600
atggcgcacg ttgcgggcct ggttgctgct ggcgtctacc cgaacccggt tcctcatgct     660
cacgttgtta ctaccaccac tcacaaaacc ctggcgggtc cgcgcggcgg cctgatcctg     720
gcgaaaggtg gtagcgaaga gctgtacaaa aaactgaact ctgccgtttt ccctggtggt     780
cagggcggtc cgttgatgca cgtaatcgcc ggtaaagcgg ttgctctgaa agaagcgatg     840
gagcctgagt tcaaaactta ccagcagcag gtcgctaaaa acgctaaagc gatggtagaa     900
gtgttcctcg agcgcggcta caaagtggtt tccggcggca ctgataacca cctgttcctg     960
gttgatctgg ttgataaaaa cctgaccggt aaagaagcag acgccgctct gggccgtgct    1020
aacatcaccg tcaacaaaaa cagcgtaccg aacgatccga gagcccgtt gtgacctcc    1080 ggtattcgtg taggtactcc ggcgattacc cgtcgcggct ttaaagaagc cgaagcgaaa    1140
gaactggctg gctggatgtg tgacgtgctg acagcatca atgatgaagc cgttatcgag    1200
cgcatcaaag gtaaagttct cgacatctgc gcacgttacc cggtttacgc ataa    1254
```

-continued

<210> SEQ ID NO 17
<211> LENGTH: 401
<212> TYPE: PRT
<213> ORGANISM: Pseudomonas sp.
<220> FEATURE:
<223> OTHER INFORMATION: Formate dehydrogenase (EC:1.17.1.9)

<400> SEQUENCE: 17

Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Thr Leu Pro Thr Pro Lys Ala Ile Asp Phe Thr Pro Gly
        35                  40                  45

Gln Leu Leu Gly Ser Val Ser Gly Glu Leu Gly Leu Arg Lys Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
            115                 120                 125

Asp Leu Gln Ser Ala Ile Asp Arg Asn Val Thr Val Ala Glu Val Thr
        130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
            195                 200                 205

Arg Arg Leu Ala Pro Phe Asp Val His Leu His Tyr Thr Asp Arg His
        210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
            275                 280                 285

Cys Asp Arg Asp Ala Val Ala Arg Ala Leu Glu Ser Gly Arg Leu Ala
        290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
            355                 360                 365

-continued

```
Val Gln Gly Gly Ala Leu Ala Gly Thr Gly Ala His Ser Tyr Ser Lys
    370             375                 380

Gly Asn Ala Thr Gly Gly Ser Glu Glu Ala Ala Lys Phe Lys Lys Ala
385             390                 395                 400

Val
```

```
<210> SEQ ID NO 18
<211> LENGTH: 1206
<212> TYPE: DNA
<213> ORGANISM: Pseudomonas sp.
<220> FEATURE:
<223> OTHER INFORMATION: Formate dehydrogenase (EC:1.17.1.9)

<400> SEQUENCE: 18
atggctaaag ttctgtgcgt tctgtacgac gacccggttg acggttaccc gaaaacctac      60
gctcgtgacg acctgccgaa aatcgaccac tacccgggtg gtcagaccct gccgaccccg     120
aaagctatcg acttcacccc gggtcagctg ctgggttctg tttctggtga actgggtctg     180
cgtaaatacc tggaatctaa cggtcacacc ctggttgtta cctctgacaa agacggtccg     240
gactctgttt cgaacgtga actggttgac gctgacgttg ttatctctca gccgttctgg      300
ccggcttacc tgaccccgga acgtatcgct aaagctaaaa acctgaaact ggctctgacc     360
gctggtatcg gttctgacca cgttgacctg caatctgcta tcgaccgtaa cgttaccgtt     420
gctgaagtta cctactgcaa ctctatctct gttgctgaac acgttgttat gatgatcctg     480
tctctggttc gtaactacct gccgtctcac gaatgggctc gtaaaggtgg ttggaacata     540
gctgactgcg taagccacgc ttacgacctg gaagctatgc acgttggtac cgttgctgct     600
ggtcgtatcg gtctggctgt tctgcgtcgt ctggctccgt cgacgttca cctgcactac     660 accgaccgtc accgtctgcc ggaatctgtt gaaaaagaac tgaacctgac ctggcacgct     720
acccgtgaag acatgtaccc ggtttgcgac gttgttaccc tgaactgccc gctgcacccg     780
gaaaccgaac acatgatcaa cgacgaaacc ctgaaactgt tcaaacgtgg tgcttacatc     840
gttaacaccg ctcgtggtaa actgtgcgac cgtgacgctg ttgctcgtgc tctggaatct     900
ggtcgtctgg ctggttatgc gggtgacgtg tggttccccc agccggctcc gaaagaccac     960
ccgtggcgta ccatgccgta caacggtatg accccgcaca tctctggtac caccctgacc    1020
gctcaggctc gttacgctgc tggtacccgt gaaatcctgg aatgcttctt cgaaggtcgt    1080
ccgatccgtg acgaatacct gatcgttcag ggtggtgctc tggctggtac cggtgctcac    1140
tcttactcta aggtaacgc taccggtggt tctgaagaag ctgctaaatt caaaaaagct    1200
gtttaa                                                            1206
```

```
<210> SEQ ID NO 19
<211> LENGTH: 510
<212> TYPE: PRT
<213> ORGANISM: Escherichia coli
<220> FEATURE:
<223> OTHER INFORMATION: NAD(P) transhydrogenase subunit alpha
      (EC:7.1.1.1)

<400> SEQUENCE: 19

Met Arg Ile Gly Ile Pro Arg Glu Arg Leu Thr Asn Glu Thr Arg Val
1               5                   10                  15

Ala Ala Thr Pro Lys Thr Val Glu Gln Leu Leu Lys Leu Gly Phe Thr
            20                  25                  30

Val Ala Val Glu Ser Gly Ala Gly Gln Leu Ala Ser Phe Asp Asp Lys
        35                  40                  45
```

```
Ala Phe Val Gln Ala Gly Ala Glu Ile Val Glu Gly Asn Ser Val Trp
    50              55              60

Gln Ser Glu Ile Ile Leu Lys Val Asn Ala Pro Leu Asp Asp Glu Ile
65              70              75              80

Ala Leu Leu Asn Pro Gly Thr Thr Leu Val Ser Phe Ile Trp Pro Ala
            85              90              95

Gln Asn Pro Glu Leu Met Gln Lys Leu Ala Glu Arg Asn Val Thr Val
            100             105             110

Met Ala Met Asp Ser Val Pro Arg Ile Ser Arg Ala Gln Ser Leu Asp
        115             120             125

Ala Leu Ser Ser Met Ala Asn Ile Ala Gly Tyr Arg Ala Ile Val Glu
    130             135             140

Ala Ala His Glu Phe Gly Arg Phe Phe Thr Gly Gln Ile Thr Ala Ala
145             150             155             160

Gly Lys Val Pro Pro Ala Lys Val Met Val Ile Gly Ala Gly Val Ala
            165             170             175

Gly Leu Ala Ala Ile Gly Ala Ala Asn Ser Leu Gly Ala Ile Val Arg
        180             185             190

Ala Phe Asp Thr Arg Pro Glu Val Lys Glu Gln Val Gln Ser Met Gly
        195             200             205

Ala Glu Phe Leu Glu Leu Asp Phe Lys Glu Glu Ala Gly Ser Gly Asp
    210             215             220

Gly Tyr Ala Lys Val Met Ser Asp Ala Phe Ile Lys Ala Glu Met Glu
225             230             235             240

Leu Phe Ala Ala Gln Ala Lys Glu Val Asp Ile Ile Val Thr Thr Ala
            245             250             255

Leu Ile Pro Gly Lys Pro Ala Pro Lys Leu Ile Thr Arg Glu Met Val
            260             265             270

Asp Ser Met Lys Ala Gly Ser Val Ile Val Asp Leu Ala Ala Gln Asn
        275             280             285

Gly Gly Asn Cys Glu Tyr Thr Val Pro Gly Glu Ile Phe Thr Thr Glu
    290             295             300

Asn Gly Val Lys Val Ile Gly Tyr Thr Asp Leu Pro Gly Arg Leu Pro
305             310             315             320

Thr Gln Ser Ser Gln Leu Tyr Gly Thr Asn Leu Val Asn Leu Leu Lys
            325             330             335

Leu Leu Cys Lys Glu Lys Asp Gly Asn Ile Thr Val Asp Phe Asp Asp
        340             345             350

Val Val Ile Arg Gly Val Thr Val Ile Arg Ala Gly Glu Ile Thr Trp
        355             360             365

Pro Ala Pro Pro Ile Gln Val Ser Ala Gln Pro Gln Ala Ala Gln Lys
    370             375             380

Ala Ala Pro Glu Val Lys Thr Glu Glu Lys Cys Thr Cys Ser Pro Trp
385             390             395             400

Arg Lys Tyr Ala Leu Met Ala Leu Ala Ile Ile Leu Phe Gly Trp Met
            405             410             415

Ala Ser Val Ala Pro Lys Glu Phe Leu Gly His Phe Thr Val Phe Ala
        420             425             430

Leu Ala Cys Val Val Gly Tyr Tyr Val Val Trp Asn Val Ser His Ala
        435             440             445

Leu His Thr Pro Leu Met Ser Val Thr Asn Ala Ile Ser Gly Ile Ile
    450             455             460
```

-continued

```
Val Val Gly Ala Leu Leu Gln Ile Gly Gln Gly Gly Trp Val Ser Phe
465             470             475             480

Leu Ser Phe Ile Ala Val Leu Ile Ala Ser Ile Asn Ile Phe Gly Gly
                485             490             495

Phe Thr Val Thr Gln Arg Met Leu Lys Met Phe Arg Lys Asn
            500             505             510

<210> SEQ ID NO 20
<211> LENGTH: 1533
<212> TYPE: DNA
<213> ORGANISM: Escherichia coli
<220> FEATURE:
<223> OTHER INFORMATION: NAD(P) transhydrogenase subunit alpha
      (EC:7.1.1.1)

<400> SEQUENCE: 20
atgcgaattg gcataccaag agaacggtta accaatgaaa cccgtgttgc agcaacgcca      60
aaaacagtgg aacagctgct gaaactgggt tttaccgtcg cggtagagag cggcgcgggt     120
caactggcaa gttttgacga taaagcgttt gtgcaagcgg cgctgaaat  tgtagaaggg     180 aatagcgtct ggcagtcaga gatcattctg aaggtcaatg cgccgttaga tgatgaaatt     240
gcgttactga atcctgggac aacgctggtg agttttatct ggcctgcgca gaatccggaa     300
ttaatgcaaa aacttgcgga acgtaacgtg accgtgatgg cgatggactc tgtgccgcgt     360
atctcacgcg cacaatcgct ggacgcacta agctcgatgg cgaacatcgc cggttatcgc     420
gccattgttg aagcggcaca tgaatttggg cgcttcttta ccgggcaaat tactgcggcc     480
gggaaagtgc caccggcaaa agtgatggtg attggtgcgg gtgttgcagg tctggccgcc     540
attggcgcag caaacagtct cggcgcgatt gtgcgtgcat cgacacccg  cccggaagtg     600 aaagaacaag ttcaaagtat gggcgcggaa ttcctcgagc tggattttaa agaggaagct     660
ggcagcggcg atggctatgc caaagtgatg tcggacgcgt tcatcaaagc ggaaatggaa     720
ctctttgccg cccaggcaaa agaggtcgat atcattgtca ccaccgcgct tattccaggc     780
aaaccagcgc cgaagctaat tacccgtgaa atggttgact ccatgaaggc gggcagtgtg     840
attgtcgacc tggcagccca aaacggcggc aactgtgaat acaccgtgcc gggtgaaatc     900
ttcactacgg aaaatggtgt caaagtgatt ggttataccg atcttccggg ccgtctgccg     960
acgcaatcct cacagcttta cggcacaaac ctcgttaatc tgctgaaact gttgtgcaaa    1020
gagaaagacg gcaatatcac tgttgatttt gatgatgtgg tgattcgcgg cgtgaccgtg    1080
atccgtgcgg cgaaaattac ctggccggca ccgccgattc aggtatcagc tcagccgcag    1140
gcggcacaaa aagcggcacc ggaagtgaaa actgaggaaa aatgtacctg ctcaccgtgg    1200
cgtaaatacg cgttgatggc gctggcaatc attcttttg  ctggatggc  aagcgttgcg    1260 ccgaaagaat ccttgggca  cttcaccgtt ttcgcgctgg cctgcgttgt cggttattac    1320
gtggtgtgga atgtatcgca cgcgctgcat acaccgttga tgtcggtcac caacgcgatt    1380
tcagggatta ttgttgtcgg agcactgttg cagattggcc agggcggctg ggttagcttc    1440
cttagtttta tcgcggtgct tatagccagc attaatattt tcggtggctt caccgtgact    1500
cagcgcatgc tgaaaatgtt ccgcaaaaat taa                                 1533

<210> SEQ ID NO 21
<211> LENGTH: 462
<212> TYPE: PRT
<213> ORGANISM: Escherichia coli
<220> FEATURE:
<223> OTHER INFORMATION: NAD(P) transhydrogenase subunit beta
```

-continued (EC:7.1.1.1)

<400> SEQUENCE: 21

```
Met Ser Gly Gly Leu Val Thr Ala Ala Tyr Ile Val Ala Ala Ile Leu
1               5                   10                  15

Phe Ile Phe Ser Leu Ala Gly Leu Ser Lys His Glu Thr Ser Arg Gln
            20                  25                  30

Gly Asn Asn Phe Gly Ile Ala Gly Met Ala Ile Ala Leu Ile Ala Thr
        35                  40                  45

Ile Phe Gly Pro Asp Thr Gly Asn Val Gly Trp Ile Leu Leu Ala Met
    50                  55                  60

Val Ile Gly Gly Ala Ile Gly Ile Arg Leu Ala Lys Lys Val Glu Met
65                  70                  75                  80

Thr Glu Met Pro Glu Leu Val Ala Ile Leu His Ser Phe Val Gly Leu
                85                  90                  95

Ala Ala Val Leu Val Gly Phe Asn Ser Tyr Leu His His Asp Ala Gly
            100                 105                 110

Met Ala Pro Ile Leu Val Asn Ile His Leu Thr Glu Val Phe Leu Gly
            115                 120                 125

Ile Phe Ile Gly Ala Val Thr Phe Thr Gly Ser Val Val Ala Phe Gly
    130                 135                 140

Lys Leu Cys Gly Lys Ile Ser Ser Lys Pro Leu Met Leu Pro Asn Arg
145                 150                 155                 160

His Lys Met Asn Leu Ala Ala Leu Val Val Ser Phe Leu Leu Leu Ile
            165                 170                 175

Val Phe Val Arg Thr Asp Ser Val Gly Leu Gln Val Leu Ala Leu Leu
            180                 185                 190

Ile Met Thr Ala Ile Ala Leu Val Phe Gly Trp His Leu Val Ala Ser
            195                 200                 205

Ile Gly Gly Ala Asp Met Pro Val Val Val Ser Met Leu Asn Ser Tyr
    210                 215                 220

Ser Gly Trp Ala Ala Ala Ala Ala Gly Phe Met Leu Ser Asn Asp Leu
225                 230                 235                 240

Leu Ile Val Thr Gly Ala Leu Val Gly Ser Ser Gly Ala Ile Leu Ser
            245                 250                 255

Tyr Ile Met Cys Lys Ala Met Asn Arg Ser Phe Ile Ser Val Ile Ala
            260                 265                 270

Gly Gly Phe Gly Thr Asp Gly Ser Ser Thr Gly Asp Asp Gln Glu Val
            275                 280                 285

Gly Glu His Arg Glu Ile Thr Ala Glu Glu Thr Ala Glu Leu Leu Lys
        290                 295                 300

Asn Ser His Ser Val Ile Ile Thr Pro Gly Tyr Gly Met Ala Val Ala
305                 310                 315                 320

Gln Ala Gln Tyr Pro Val Ala Glu Ile Thr Glu Lys Leu Arg Ala Arg
            325                 330                 335

Gly Ile Asn Val Arg Phe Gly Ile His Pro Val Ala Gly Arg Leu Pro
        340                 345                 350

Gly His Met Asn Val Leu Leu Ala Glu Ala Lys Val Pro Tyr Asp Ile
        355                 360                 365

Val Leu Glu Met Asp Glu Ile Asn Asp Asp Phe Ala Asp Thr Asp Thr
    370                 375                 380

Val Leu Val Ile Gly Ala Asn Asp Thr Val Asn Pro Ala Ala Gln Asp
385                 390                 395                 400
```

-continued

```
Asp Pro Lys Ser Pro Ile Ala Gly Met Pro Val Leu Glu Val Trp Lys
            405                 410                 415

Ala Gln Asn Val Ile Val Phe Lys Arg Ser Met Asn Thr Gly Tyr Ala
            420                 425                 430

Gly Val Gln Asn Pro Leu Phe Phe Lys Glu Asn Thr His Met Leu Phe
        435                 440                 445

Gly Asp Ala Lys Ala Ser Val Asp Ala Ile Leu Lys Ala Leu
    450                 455                 460
```

```
<210> SEQ ID NO 22
<211> LENGTH: 1389
<212> TYPE: DNA
<213> ORGANISM: Escherichia coli
<220> FEATURE:
<223> OTHER INFORMATION: NAD(P) transhydrogenase subunit beta
      (EC:7.1.1.1)

<400> SEQUENCE: 22
atgtctggag gattagttac agctgcatac attgttgccg cgatcctgtt tatcttcagt      60
ctggccggtc tttcgaaaca tgaaacgtct cgccagggta acaacttcgg tatcgccggg     120
atggcgattg cgttaatcgc aaccattttt ggaccggata cgggtaatgt tggctggatc     180
ttgctggcga tggtcattgg tggggcaatt ggtatccgtc tggcgaagaa agttgaaatg     240
accgaaatgc cagaactggt ggcgatcctg catagcttcg tgggtctggc ggcagtgctg     300
gttggcttta acagctatct gcatcatgac gcgggaatgg caccgattct ggtcaatatt     360
cacctgacgg aagtgttcct cggtatcttc atcgggcgg taacgttcac gggttcggtg     420
gtggcgttcg gcaaactgtg tggcaagatt cgtctaaac cattgatgct gccaaaccgt     480
cacaaaatga acctggcggc tctggtcgtt tccttcctgc tgctgattgt atttgttcgc     540
acggacagcg tcggcctgca agtgctggca ttgctgataa tgaccgcaat tgcgctggta     600
ttcggctggc atttagtcgc ctccatcggt ggtgcagata tgccagtggt ggtgtcgatg     660
ctgaactcgt actccggctg ggcggctgcg gctgcgggct ttatgctcag caacgacctg     720
ctgattgtga ccggtgcgct ggtcggttct tcggggcta tcctttctta cattatgtgt     780
aaggcgatga accgttcctt tatcagcgtt attgcgggtg tttcggcac cgacggctct     840 tctactggcg atgatcagga agtgggtgag caccgcgaaa tcaccgcaga agagacagcg     900
gaactgctga aaaactccca ttcagtgatc attactccgg ggtacggcat ggcagtcgcg     960
caggcgcaat atcctgtcgc tgaaattact gagaaattgc gcgctcgtgg tattaatgtg    1020
cgtttcggta tccacccggt cgcggggcgt ttgcctggac atatgaacgt attgctggct    1080
gaagcaaaag taccgtatga catcgtgctg aaatggacg agatcaatga tgactttgct    1140
gataccgata ccgtactggt gattggtgct aacgatacgg ttaacccggc ggcgcaggat    1200
gatccgaaga gtccgattgc tggtatgcct gtgctggaag tgtggaaagc gcagaacgtg    1260
attgtcttta acgttcgat gaacactggc tatgctggtg tgcaaaaccc gctgttcttc    1320
aaggaaaaca cccacatgct gtttggtgac gccaaagcca gcgtggatgc aatcctgaaa    1380
gctctgtaa                                                            1389
```

```
<210> SEQ ID NO 23
<211> LENGTH: 468
<212> TYPE: PRT
<213> ORGANISM: Escherichia coli
<220> FEATURE:
<223> OTHER INFORMATION: 6-phosphogluconate dehydrogenase
      (Gnd, EC 1.1.1.44)
```

-continued

<400> SEQUENCE: 23

Met Ser Lys Gln Gln Ile Gly Val Val Gly Met Ala Val Met Gly Arg
1               5                   10                  15

Asn Leu Ala Leu Asn Ile Glu Ser Arg Gly Tyr Thr Val Ser Ile Phe
            20                  25                  30

Asn Arg Ser Arg Glu Lys Thr Glu Glu Val Ile Ala Glu Asn Pro Gly
        35                  40                  45

Lys Lys Leu Val Pro Tyr Tyr Thr Val Lys Glu Phe Val Glu Ser Leu
    50                  55                  60

Glu Thr Pro Arg Arg Ile Leu Leu Met Val Lys Ala Gly Ala Gly Thr
65                  70                  75                  80

Asp Ala Ala Ile Asp Ser Leu Lys Pro Tyr Leu Asp Lys Gly Asp Ile
                85                  90                  95

Ile Ile Asp Gly Gly Asn Thr Phe Phe Gln Asp Thr Ile Arg Arg Asn
                100                 105                 110

Arg Glu Leu Ser Ala Glu Gly Phe Asn Phe Ile Gly Thr Gly Val Ser
            115                 120                 125

Gly Gly Glu Glu Gly Ala Leu Lys Gly Pro Ser Ile Met Pro Gly Gly
    130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
                165                 170                 175

Gly Ala Gly His Tyr Val Lys Met Val His Asn Gly Ile Glu Tyr Gly
            180                 185                 190

Asp Met Gln Leu Ile Ala Glu Ala Tyr Ser Leu Leu Lys Gly Gly Leu
            195                 200                 205

Asn Leu Thr Asn Glu Glu Leu Ala Gln Thr Phe Thr Glu Trp Asn Asn
    210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
                245                 250                 255

Ala Ala Asn Lys Gly Thr Gly Lys Trp Thr Ser Gln Ser Ala Leu Asp
            260                 265                 270

Leu Gly Glu Pro Leu Ser Leu Ile Thr Glu Ser Val Phe Ala Arg Tyr
        275                 280                 285

Ile Ser Ser Leu Lys Asp Gln Arg Val Ala Ala Ser Lys Val Leu Ser
    290                 295                 300

Gly Pro Gln Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
            325                 330                 335

Phe Ser Gln Leu Arg Ala Ala Ser Glu Glu Tyr Asn Trp Asp Leu Asn
            340                 345                 350

Tyr Gly Glu Ile Ala Lys Ile Phe Arg Ala Gly Cys Ile Ile Arg Ala
            355                 360                 365

Gln Phe Leu Gln Lys Ile Thr Asp Ala Tyr Ala Glu Asn Pro Gln Ile
    370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile

-continued

```
                 405              410              415
Pro Val Pro Thr Phe Ser Ala Ala Val Ala Tyr Tyr Asp Ser Tyr Arg
            420              425              430

Ala Ala Val Leu Pro Ala Asn Leu Ile Gln Ala Gln Arg Asp Tyr Phe
        435              440              445

Gly Ala His Thr Tyr Lys Arg Ile Asp Lys Glu Gly Val Phe His Thr
    450              455              460

Glu Trp Leu Asp
465

<210> SEQ ID NO 24
<211> LENGTH: 1407
<212> TYPE: DNA
<213> ORGANISM: Escherichia coli
<220> FEATURE:
<223> OTHER INFORMATION: 6-phosphogluconate dehydrogenase
      (Gnd, EC 1.1.1.44)

<400> SEQUENCE: 24
atgtccaagc aacagatcgg cgtagtcggt atggcagtga tgggacgcaa ccttgcgctc      60
aacatcgaaa gccgtggtta taccgtctct attttcaacc gttcccgtga aagacggaa      120 gaagtgattg ccgaaaatcc aggcaagaaa ctggttcctt actatacggt gaaagagttt      180
gtcgaatctc tggaaacgcc tcgtcgcatc ctgttaatgg tgaaagcagg tgcaggcacg      240
gatgctgcta ttgattccct caaaccatat ctcgataaag gagacatcat cattgatggt      300
ggtaacacct tcttccagga cactattcgt cgtaatcgtg agctttcagc agagggcttt      360
aacttcatcg gtaccggtgt ttctggcggt gaagaggggg cgctgaaagg tccttctatt      420
atgcctggtg gccagaaaga agcctatgaa ttggtagcac cgatcctgac caaaatcgcc      480
gccgtagctg aagacggtga accatgcgtt acctatattg gtgccgatgg cgcaggtcac      540
tatgtgaaga tggttcacaa cggtattgaa tacggcgata tgcagctgat tgctgaagcc      600
tattctctgc ttaaaggtgg cctgaacctc accaacgaag aactggcgca gaccttttacc      660 gagtggaata cggtgaact gagcagttac ctgatcgaca tcaccaaaga tatcttcacc      720
aaaaaagatg aagacggtaa ctacctggtt gatgtgatcc tggatgaagc ggctaacaaa      780
ggtaccggta aatggaccag ccagagcgcg ctggatctcg gcgaaccgct gtcgctgatt      840
accgagtctg tgtttgcacg ttatatctct tctctgaaag atcagcgtgt tgccgcatct      900
aaagttctct ctggtccgca agcacagcca gcaggcgaca aggctgagtt catcgaaaaa      960
gttcgtcgtg cgctgtatct gggcaaaatc gtttcttacg cccagggctt ctctcagctg     1020
cgtgctgcgt ctgaagagta caactgggat ctgaactacg cgaaatcgc gaagattttc     1080 cgtgctggct gcatcatccg tgcgcagttc ctgcagaaaa tcaccgatgc ttatgccgaa     1140
aatccacaga tcgctaacct gttgctggct ccgtacttca gcaaattgc cgatgactac     1200 cagcaggcgc tgcgtgatgt cgttgcttat gcagtacaga acggtattcc ggttccgacc     1260
ttctccgcag cggttgccta ttacgacagc taccgtgctg ctgttctgcc tgcgaacctg     1320
atccaggcac agcgtgacta ttttggtgcg catacttata agcgtattga taaagaaggt     1380
gtgttccata ccgaatggct ggattaa                                         1407

<210> SEQ ID NO 25
<211> LENGTH: 416
<212> TYPE: PRT
<213> ORGANISM: Escherichia coli
<220> FEATURE:
```

<223> OTHER INFORMATION: isocitrate dehydrogenase (Icd, 1.1.1.41-42)

<400> SEQUENCE: 25

```
Met Glu Ser Lys Val Val Pro Ala Gln Gly Lys Lys Ile Thr Leu
1               5                   10                  15

Gln Asn Gly Lys Leu Asn Val Pro Glu Asn Pro Ile Ile Pro Tyr Ile
            20                  25                  30

Glu Gly Asp Gly Ile Gly Val Asp Val Thr Pro Ala Met Leu Lys Val
        35                  40                  45

Val Asp Ala Ala Val Glu Lys Ala Tyr Lys Gly Glu Arg Lys Ile Ser
    50                  55                  60

Trp Met Glu Ile Tyr Thr Gly Glu Lys Ser Thr Gln Val Tyr Gly Gln
65                  70                  75                  80

Asp Val Trp Leu Pro Ala Glu Thr Leu Asp Leu Ile Arg Glu Tyr Arg
                85                  90                  95

Val Ala Ile Lys Gly Pro Leu Thr Thr Pro Val Gly Gly Gly Ile Arg
            100                 105                 110

Ser Leu Asn Val Ala Leu Arg Gln Glu Leu Asp Leu Tyr Ile Cys Leu
        115                 120                 125

Arg Pro Val Arg Tyr Tyr Gln Gly Thr Pro Ser Pro Val Lys His Pro
    130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Ala Asp Ala Glu Lys Val Ile
                165                 170                 175

Lys Phe Leu Arg Glu Glu Met Gly Val Lys Lys Ile Arg Phe Pro Glu
            180                 185                 190

His Cys Gly Ile Gly Ile Lys Pro Cys Ser Glu Glu Gly Thr Lys Arg
        195                 200                 205

Leu Val Arg Ala Ala Ile Glu Tyr Ala Ile Ala Asn Asp Arg Asp Ser
    210                 215                 220

Val Thr Leu Val His Lys Gly Asn Ile Met Lys Phe Thr Glu Gly Ala
225                 230                 235                 240

Phe Lys Asp Trp Gly Tyr Gln Leu Ala Arg Glu Glu Phe Gly Gly Glu
                245                 250                 255

Leu Ile Asp Gly Gly Pro Trp Leu Lys Val Lys Asn Pro Asn Thr Gly
            260                 265                 270

Lys Glu Ile Val Ile Lys Asp Val Ile Ala Asp Ala Phe Leu Gln Gln
        275                 280                 285

Ile Leu Leu Arg Pro Ala Glu Tyr Asp Val Ile Ala Cys Met Asn Leu
    290                 295                 300

Asn Gly Asp Tyr Ile Ser Asp Ala Leu Ala Ala Gln Val Gly Gly Ile
305                 310                 315                 320

Gly Ile Ala Pro Gly Ala Asn Ile Gly Asp Glu Cys Ala Leu Phe Glu
                325                 330                 335

Ala Thr His Gly Thr Ala Pro Lys Tyr Ala Gly Gln Asp Lys Val Asn
            340                 345                 350

Pro Gly Ser Ile Ile Leu Ser Ala Glu Met Met Leu Arg His Met Gly
            355                 360                 365

Trp Thr Glu Ala Ala Asp Leu Ile Val Lys Gly Met Glu Gly Ala Ile
    370                 375                 380

Asn Ala Lys Thr Val Thr Tyr Asp Phe Glu Arg Leu Met Asp Gly Ala
385                 390                 395                 400
```

```
Lys Leu Leu Lys Cys Ser Glu Phe Gly Asp Ala Ile Ile Glu Asn Met
            405                 410                 415
```

```
<210> SEQ ID NO 26
<211> LENGTH: 1251
<212> TYPE: DNA
<213> ORGANISM: Escherichia coli
<220> FEATURE:
<223> OTHER INFORMATION: isocitrate dehydrogenase (Icd, 1.1.1.41-42)

<400> SEQUENCE: 26
atggaaagta aagtagttgt tccggcacaa ggcaagaaga tcaccctgca aaacggcaaa      60
ctcaacgttc ctgaaaatcc gattatccct tacattgaag gtgatggaat cggtgtagat     120
gtaaccccag ccatgctgaa agtggtcgac gctgcagtcg agaaagccta taaggcgag      180 cgtaaaatct cctggatgga aatttacacc ggtgaaaaat ccacacaggt ttatggtcag     240
gacgtctggc tgcctgctga aactcttgat ctgattcgtg aatatcgcgt tgccattaaa     300
ggtccgctga ccactccggt tggtggcggt attcgctctc tgaacgttgc cctgcgccag     360
gaactggatc tctacatctg cctgcgtccg gtacgttact atcagggcac tccaagcccg     420
gttaaacacc ctgaactgac cgatatggtt atcttccgtg aaaactcgga agacatttat     480
gcgggtatcg aatggaaagc agactctgcc gacgccgaga aagtgattaa attcctgcgt     540
gaagagatgg gggtgaagaa aattcgcttc ccggaacatt gtggtatcgg tattaagccg     600
tgttcggaag aaggcaccaa acgtctggtt cgtgcagcga tcgaatacgc aattgctaac     660
gatcgtgact ctgtgactct ggtgcacaaa ggcaacatca tgaagttcac cgaaggagcg     720
tttaaagact ggggctacca gctggcgcgt gaagagtttg gcggtgaact gatcgacggt     780
ggcccgtggc tgaaagttaa aaacccgaac actggcaaag agatcgtcat taaagacgtg     840
attgctgatg cattcctgca acagatcctg ctgcgtccgg ctgaatatga tgttatcgcc     900
tgtatgaacc tgaacggtga ctacatttct gacgccctgg cagcgcaggt tggcggtatc     960
ggtatcgccc ctggtgcaaa catcggtgac gaatgcgccc tgtttgaagc cacccacggt    1020
actgcgccga atatgccggt caggacaaa gtaaatcctg ctctattat tctctccgct    1080 gagatgatgc tgcgccacat gggttggacc gaagcggctg acttaattgt taaaggtatg    1140
gaaggcgcaa tcaacgcgaa aaccgtaacc tatgacttcg agcgtctgat ggatggcgct    1200
aaactgctga atgttcaga gtttggtgac gcgatcatcg aaaacatgta a            1251
```

```
<210> SEQ ID NO 27
<211> LENGTH: 759
<212> TYPE: PRT
<213> ORGANISM: Escherichia coli
<220> FEATURE:
<223> OTHER INFORMATION: malic enzyme (MaeB, EC 1.1.1.38-40)

<400> SEQUENCE: 27

Met Asp Asp Gln Leu Lys Gln Ser Ala Leu Asp Phe His Glu Phe Pro
1               5                   10                  15

Val Pro Gly Lys Ile Gln Val Ser Pro Thr Lys Pro Leu Ala Thr Gln
            20                  25                  30

Arg Asp Leu Ala Leu Ala Tyr Ser Pro Gly Val Ala Ala Pro Cys Leu
        35                  40                  45

Glu Ile Glu Lys Asp Pro Leu Lys Ala Tyr Lys Tyr Thr Ala Arg Gly
    50                  55                  60

Asn Leu Val Ala Val Ile Ser Asn Gly Thr Ala Val Leu Gly Leu Gly
65                  70                  75                  80
```

-continued

```
Asn Ile Gly Ala Leu Ala Gly Lys Pro Val Met Glu Gly Lys Gly Val
              85                  90                  95

Leu Phe Lys Lys Phe Ala Gly Ile Asp Val Phe Asp Ile Glu Val Asp
             100                 105                 110

Glu Leu Asp Pro Asp Lys Phe Ile Glu Val Val Ala Ala Leu Glu Pro
             115                 120                 125

Thr Phe Gly Gly Ile Asn Leu Glu Asp Ile Lys Ala Pro Glu Cys Phe
             130                 135                 140

Tyr Ile Glu Gln Lys Leu Arg Glu Arg Met Asn Ile Pro Val Phe His
145                 150                 155                 160

Asp Asp Gln His Gly Thr Ala Ile Ile Ser Thr Ala Ala Ile Leu Asn
             165                 170                 175

Gly Leu Arg Val Val Glu Lys Asn Ile Ser Asp Val Arg Met Val Val
             180                 185                 190

Ser Gly Ala Gly Ala Ala Ala Ile Ala Cys Met Asn Leu Leu Val Ala
             195                 200                 205

Leu Gly Leu Gln Lys His Asn Ile Val Val Cys Asp Ser Lys Gly Val
             210                 215                 220

Ile Tyr Gln Gly Arg Glu Pro Asn Met Ala Glu Thr Lys Ala Ala Tyr
225                 230                 235                 240

Ala Val Val Asp Asp Gly Lys Arg Thr Leu Asp Asp Val Ile Glu Gly
             245                 250                 255

Ala Asp Ile Phe Leu Gly Cys Ser Gly Pro Lys Val Leu Thr Gln Glu
             260                 265                 270

Met Val Lys Lys Met Ala Arg Ala Pro Met Ile Leu Ala Leu Ala Asn
             275                 280                 285

Pro Glu Pro Glu Ile Leu Pro Pro Leu Ala Lys Glu Val Arg Pro Asp
             290                 295                 300

Ala Ile Ile Cys Thr Gly Arg Ser Asp Tyr Pro Asn Gln Val Asn Asn
305                 310                 315                 320

Val Leu Cys Phe Pro Phe Ile Phe Arg Gly Ala Leu Asp Val Gly Ala
             325                 330                 335

Thr Ala Ile Asn Glu Glu Met Lys Leu Ala Ala Val Arg Ala Ile Ala
             340                 345                 350

Glu Leu Ala His Ala Glu Gln Ser Glu Val Val Ala Ser Ala Tyr Gly
             355                 360                 365

Asp Gln Asp Leu Ser Phe Gly Pro Glu Tyr Ile Ile Pro Lys Pro Phe
             370                 375                 380

Asp Pro Arg Leu Ile Val Lys Ile Ala Pro Ala Val Ala Lys Ala Ala
385                 390                 395                 400

Met Glu Ser Gly Val Ala Thr Arg Pro Ile Ala Asp Phe Asp Val Tyr
             405                 410                 415

Ile Asp Lys Leu Thr Glu Phe Val Tyr Lys Thr Asn Leu Phe Met Lys
             420                 425                 430

Pro Ile Phe Ser Gln Ala Arg Lys Ala Pro Lys Arg Val Val Leu Pro
             435                 440                 445

Glu Gly Glu Glu Ala Arg Val Leu His Ala Thr Gln Glu Leu Val Thr
             450                 455                 460

Leu Gly Leu Ala Lys Pro Ile Leu Ile Gly Arg Pro Asn Val Ile Glu
465                 470                 475                 480

Met Arg Ile Gln Lys Leu Gly Leu Gln Ile Lys Ala Gly Val Asp Phe
             485                 490                 495
```

```
Glu Ile Val Asn Asn Glu Ser Asp Pro Arg Phe Lys Glu Tyr Trp Thr
        500                 505                 510

Glu Tyr Phe Gln Ile Met Lys Arg Arg Gly Val Thr Gln Glu Gln Ala
        515                 520                 525

Gln Arg Ala Leu Ile Ser Asn Pro Thr Val Ile Gly Ala Ile Met Val
        530                 535                 540

Gln Arg Gly Glu Ala Asp Ala Met Ile Cys Gly Thr Val Gly Asp Tyr
545                 550                 555                 560

His Glu His Phe Ser Val Val Lys Asn Val Phe Gly Tyr Arg Asp Gly
                565                 570                 575

Val His Thr Ala Gly Ala Met Asn Ala Leu Leu Leu Pro Ser Gly Asn
        580                 585                 590

Thr Phe Ile Ala Asp Thr Tyr Val Asn Asp Glu Pro Asp Ala Glu Glu
        595                 600                 605

Leu Ala Glu Ile Thr Leu Met Ala Ala Glu Thr Val Arg Arg Phe Gly
        610                 615                 620

Ile Glu Pro Arg Val Ala Leu Leu Ser His Ser Asn Phe Gly Ser Ser
625                 630                 635                 640

Asp Cys Pro Ser Ser Ser Lys Met Arg Gln Ala Leu Glu Leu Val Arg
                645                 650                 655

Glu Arg Ala Pro Glu Leu Met Ile Asp Gly Glu Met His Gly Asp Ala
                660                 665                 670

Ala Leu Val Glu Ala Ile Arg Asn Asp Arg Met Pro Asp Ser Ser Leu
        675                 680                 685

Lys Gly Ser Ala Asn Ile Leu Val Met Pro Asn Met Glu Ala Ala Arg
        690                 695                 700

Ile Ser Tyr Asn Leu Leu Arg Val Ser Ser Ser Glu Gly Val Thr Val
705                 710                 715                 720

Gly Pro Val Leu Met Gly Val Ala Lys Pro Val His Val Leu Thr Pro
                725                 730                 735

Ile Ala Ser Val Arg Arg Ile Val Asn Met Val Ala Leu Ala Val Val
        740                 745                 750

Glu Ala Gln Thr Gln Pro Leu
        755
```

<210> SEQ ID NO 28
<211> LENGTH: 2280
<212> TYPE: DNA
<213> ORGANISM: Escherichia coli
<220> FEATURE:
<223> OTHER INFORMATION: malic enzyme (MaeB, EC 1.1.1.38-40)

<400> SEQUENCE: 28

```
atggatgacc agttaaaaca aagtgcactt gatttccatg aatttccagt tccagggaaa      60
atccaggttt ctccaaccaa gcctctggca acacagcgcg atctggcgct ggcctactca     120
ccaggcgttg ccgcaccttg tcttgaaatc gaaaaagacc cgttaaaagc ctacaaatat     180
accgcccgag gtaacctggt ggcggtgatc tctaacggta cggcggtgct ggggttaggc     240
aacattggcg cgctggcagg caaaccggtg atggaaggca agggcgttct gtttaagaaa     300
ttcgccggga ttgatgtatt tgacattgaa gttgacgaac tcgacccgga caaatttatt     360
gaagttgtcg ccgcgctcga accaaccttc ggcggcatca acctcgaaga cattaaagcg     420
ccagaatgtt ctatattga acagaaactg cgcgagcgga tgaatattcc ggtattccac     480
gacgatcagc acggcacggc aattatcagc actgccgcca tcctcaacgg cttgcgcgtg     540
```

```
gtggagaaaa acatctccga cgtgcggatg gtggtttccg gcgcgggtgc cgcagcaatc        600
gcctgtatga acctgctggt agcgctgggt ctgcaaaaac ataacatcgt ggtttgcgat        660
tcaaaaggcg ttatctatca gggccgtgag ccaaacatgg cggaaaccaa agccgcatat        720
gcggtggtgg atgacggcaa acgtaccctc gatgatgtga ttgaaggcgc ggatattttc        780
ctgggctgtt ccggcccgaa agtgctgacc caggaaatgg tgaagaaaat ggctcgtgcg        840
ccaatgatcc tggcgctggc gaacccggaa ccgaaattc tgccgccgct ggcgaaagaa         900
gtgcgtccgg atgccatcat ttgcaccggt cgttctgact atccgaacca ggtgaacaac        960
gtcctgtgct tcccgttcat cttccgtggc gcgctggacg ttggcgcaac cgccatcaac       1020
gaagagatga aactggcggc ggtacgtgcg attgcagaac tcgcccatgc ggaacagagc       1080
gaagtggtgg cttcagcgta tggcgatcag gatctgagct ttggtccgga atacatcatt       1140
ccaaaaccgt ttgatccgcg cttgatcgtt aagatcgctc ctgcggtcgc taaagccgcg       1200
atggagtcgg gcgtggcgac tcgtccgatt gctgatttcg acgtctacat cgacaagctg       1260
actgagttcg tttacaaaac caacctgttt atgaagccga ttttctccca ggctcgcaaa       1320
gcgccgaagc gcgttgttct gccggaaggg aagaggcgc gcgttctgca tgccactcag        1380
gaactggtaa cgctgggact ggcgaaaccg atccttatcg gtcgtccgaa cgtgatcgaa       1440
atgcgcattc agaaactggg cttgcagatc aaagcgggcg ttgattttga gatcgtcaat       1500
aacgaatccg atccgcgctt taaagagtac tggaccgaat acttccagat catgaagcgt       1560
cgcggcgtca ctcaggaaca ggcgcagcgg gcgctgatca gtaacccgac agtgatcggc       1620
gcgatcatgg ttcagcgtgg ggaagccgat gcaatgattt gcggtacggt gggtgattat       1680
catgaacatt ttagcgtggt gaaaaatgtc tttggttatc gcgatggcgt tcacaccgca       1740
ggtgccatga acgcgctgct gctgccgagt ggtaacacct ttattgccga tacatatgtt       1800
aatgatgaac cggatgcaga agagctggcg gagatcacct tgatggcggc agaaactgtc       1860
cgtcgttttg gtattgagcc gcgcgttgct ttgttgtcgc actccaactt tggttcttct       1920
gactgcccgt cgtcgagcaa aatgcgtcag gcgctggaac tggtcaggga acgtgcacca       1980
gaactgatga ttgatggtga aatgcacggc gatgcagcgc tggtggaagc gattcgcaac       2040
gaccgtatgc cggacagctc tttgaaaggt tccgccaata ttctggtgat gccgaacatg       2100
gaagctgccc gcattagtta caacttactg cgtgtttcca gctcggaagg tgtgactgtc       2160
ggcccggtgc tgatgggtgt ggcgaaaccg gttcacgtgt aacgccgat cgcatcggtg        2220 cgtcgtatcg tcaacatggt ggcgctggcc gtggtagaag cgcaaaccca accgctgtaa       2280
```

<210> SEQ ID NO 29
<211> LENGTH: 491
<212> TYPE: PRT
<213> ORGANISM: Escherichia coli
<220> FEATURE:
<223> OTHER INFORMATION: glucose 6-phosphate dehydrogenase
      (Zwf, EC 1.1.1.49)

<400> SEQUENCE: 29

```
Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Ala Gly Gln Leu Asn Pro Asp Thr Arg Ile Ile Gly Val
        35                  40                  45

Gly Arg Ala Asp Trp Asp Lys Ala Ala Tyr Thr Lys Val Val Arg Glu
```

-continued

```
              50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
                100                 105                 110

Thr Ile Asn Tyr Phe Ala Met Pro Pro Ser Thr Phe Gly Ala Ile Cys
                115                 120                 125

Lys Gly Leu Gly Glu Ala Lys Leu Asn Ala Lys Pro Ala Arg Val Val
                130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
                180                 185                 190

Ala Asn Ser Leu Phe Val Asn Asn Trp Asp Asn Arg Thr Ile Asp His
                195                 200                 205

Val Glu Ile Thr Val Ala Glu Glu Val Gly Ile Glu Gly Arg Trp Gly
                210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
                260                 265                 270

Arg Ile Asp Arg Ser Asn Val Arg Glu Lys Thr Val Arg Gly Gln Tyr
                275                 280                 285

Thr Ala Gly Phe Ala Gln Gly Lys Lys Val Pro Gly Tyr Leu Glu Glu
                290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

Thr Gly Lys Arg Leu Pro Thr Lys Cys Ser Glu Val Val Val Tyr Phe
                340                 345                 350

Lys Thr Pro Glu Leu Asn Leu Phe Lys Glu Ser Trp Gln Asp Leu Pro
                355                 360                 365

Gln Asn Lys Leu Thr Ile Arg Leu Gln Pro Asp Glu Gly Val Asp Ile
                370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
                420                 425                 430

Gln Ala Leu Phe Val Arg Arg Asp Glu Val Glu Glu Ala Trp Lys Trp
                435                 440                 445

Val Asp Ser Ile Thr Glu Ala Trp Ala Met Asp Asn Asp Ala Pro Lys
                450                 455                 460

Pro Tyr Gln Ala Gly Thr Trp Gly Pro Val Ala Ser Val Ala Met Ile
465                 470                 475                 480
```

Thr Arg Asp Gly Arg Ser Trp Asn Glu Phe Glu
                485                     490

<210> SEQ ID NO 30
<211> LENGTH: 1476
<212> TYPE: DNA
<213> ORGANISM: Escherichia coli
<220> FEATURE:
<223> OTHER INFORMATION: glucose 6-phosphate dehydrogenase
      (Zwf, EC 1.1.1.49)

<400> SEQUENCE: 30
atggcggtaa cgcaaacagc ccaggcctgt gacctggtca ttttcggcgc gaaaggcgac        60
cttgcgcgtc gtaaattgct gccttccctg tatcaactgg aaaaagccgg tcagctcaac       120
ccggacaccc ggattatcgg cgtagggcgt gctgactggg ataaagcggc atataccaaa       180
gttgtccgcg aggcgctcga aactttcatg aaagaaacca ttgatgaagg tttatgggac       240
accctgagtg cacgtctgga ttttgtaat ctcgatgtca atgacactgc tgcattcagc       300
cgtctcggcg cgatgctgga tcaaaaaaat cgtatcacca ttaactactt tgccatgccg       360
cccagcactt ttggcgcaat ttgcaaaggg cttggcgagg caaaactgaa tgctaaaccg       420
gcacgcgtag tcatggagaa accgctgggg acgtcgctgg cgacctcgca ggaaatcaat       480
gatcaggttg gcgaatactt cgaggagtgc caggtttacc gtatcgacca ctatcttggt       540
aaagaaacgg tgctgaacct gttggcgctg cgttttgcta actccctgtt tgtgaataac       600
tgggacaatc gcaccattga tcatgttgag attaccgtgg cagaagaagt ggggatcgaa       660
gggcgctggg gctattttga taaagccggt cagatgcgcg acatgatcca gaaccacctg       720
ctgcaaattc tttgcatgat tgcgatgtct ccgccgtctg acctgagcgc agacagcatc       780
cgcgatgaaa aagtgaaagt actgaagtct ctgcgccgca tcgaccgctc caacgtacgc       840 gaaaaaccg tacgcgggca atatactgcg ggcttcgccc agggcaaaaa agtgccggga       900
tatctggaag aagagggcgc gaacaagagc agcaatacag aaactttcgt ggcgatccgc       960
gtcgacattg ataactggcg ctgggccggt gtgccattct acctgcgtac tggtaaacgt      1020
ctgccgacca aatgttctga agtcgtggtc tatttcaaaa cacctgaact gaatctgttt      1080
aaagaatcgt ggcaggatct gccgcagaat aaactgacta tccgtctgca acctgatgaa      1140
ggcgtggata tccaggtact gaataaagtt cctggccttg accacaaaca taacctgcaa      1200
atcaccaagc tggatctgag ctattcagaa acctttaatc agacgcatct ggcggatgcc      1260
tatgaacgtt tgctgctgga aaccatgcgt ggtattcagg cactgtttgt acgtcgcgac      1320
gaagtggaag aagcctggaa atgggtagac tccattactg aggcgtgggc gatggacaat      1380
gatgcgccga aaccgtatca ggccggaacc tggggacccg ttgcctcggt ggcgatgatt      1440
acccgtgatg gtcgttcctg gaatgagttt gagtaa                               1476

<210> SEQ ID NO 31
<211> LENGTH: 117
<212> TYPE: DNA
<213> ORGANISM: Artificial Sequence
<220> FEATURE:
<223> OTHER INFORMATION: Promoter of mutated pntAB

<400> SEQUENCE: 31
tagggtgttt gttactaatt tattttaacg gagtaacatt tagctcgtac atgagcagct        60
tgtgtggctc ctgacacagg caaaccatca tcaataaaac cgatggaagg gaatatc         117

-continued

<210> SEQ ID NO 32
<211> LENGTH: 66
<212> TYPE: DNA
<213> ORGANISM: Artificial Sequence
<220> FEATURE:
<223> OTHER INFORMATION: UTR of mutated fdh

<400> SEQUENCE: 32
caggacgcaa tgaccgaatt cactagttaa tagaaataat tttgtttaac tttaaggagg        60
tttgga                                                                    66

<210> SEQ ID NO 33
<211> LENGTH: 339
<212> TYPE: PRT
<213> ORGANISM: Bacillus stearothermophilus
<220> FEATURE:
<223> OTHER INFORMATION: methanol dehydrogenases

<400> SEQUENCE: 33

Met Lys Ala Ala Val Val Asn Glu Phe Lys Lys Ala Leu Glu Ile Lys
1               5                   10                  15

Glu Val Glu Arg Pro Lys Leu Glu Glu Gly Glu Val Leu Val Lys Ile
            20                  25                  30

Glu Ala Cys Gly Val Cys His Thr Asp Leu His Ala Ala His Gly Asp
        35                  40                  45

Trp Pro Ile Lys Pro Lys Leu Pro Leu Ile Pro Gly His Glu Gly Val
    50                  55                  60

Gly Ile Val Val Glu Val Ala Lys Gly Val Lys Ser Ile Lys Val Gly
65                  70                  75                  80

Asp Arg Val Gly Ile Pro Trp Leu Tyr Ser Ala Cys Gly Glu Cys Glu
                85                  90                  95

Tyr Cys Leu Thr Gly Gln Glu Thr Leu Cys Pro His Gln Leu Asn Gly
            100                 105                 110

Gly Tyr Ser Val Asp Gly Gly Tyr Ala Glu Tyr Cys Lys Ala Pro Ala
            115                 120                 125

Asp Tyr Val Ala Lys Ile Pro Asp Asn Leu Asp Pro Val Glu Val Ala
        130                 135                 140

Pro Ile Leu Cys Ala Gly Val Thr Thr Tyr Lys Ala Leu Lys Val Ser
145                 150                 155                 160

Gly Ala Arg Pro Gly Glu Trp Val Ala Ile Tyr Gly Ile Gly Gly Leu
                165                 170                 175

Gly His Ile Ala Leu Gln Tyr Ala Lys Ala Met Gly Leu Asn Val Val
            180                 185                 190

Ala Val Asp Ile Ser Asp Glu Lys Ser Lys Leu Ala Lys Asp Leu Gly
            195                 200                 205

Ala Asp Ile Ala Ile Asn Gly Leu Lys Glu Asp Pro Val Lys Ala Ile
        210                 215                 220

His Asp Gln Val Gly Gly Val His Ala Ala Ile Ser Val Ala Val Asn
225                 230                 235                 240

Lys Lys Ala Phe Glu Gln Ala Tyr Gln Ser Val Lys Arg Gly Gly Thr
                245                 250                 255

Leu Val Val Val Gly Leu Pro Asn Ala Asp Leu Pro Ile Pro Ile Phe
            260                 265                 270

Asp Thr Val Leu Asn Gly Val Ser Val Lys Gly Ser Ile Val Gly Thr
        275                 280                 285

Arg Lys Asp Met Gln Glu Ala Leu Asp Phe Ala Ala Arg Gly Lys Val

<table>
<tr><td>290</td><td>295</td><td>300</td></tr>
</table>

```
                  290              295              300
Arg Pro Ile Val Glu Thr Ala Glu Leu Glu Glu Ile Asn Glu Val Phe
305              310              315              320

Glu Arg Met Glu Lys Gly Lys Ile Asn Gly Arg Ile Val Leu Lys Leu
                325              330              335

Lys Glu Asp
```

<210> SEQ ID NO 34
<211> LENGTH: 1020
<212> TYPE: DNA
<213> ORGANISM: Bacillus stearothermophilus
<220> FEATURE:
<223> OTHER INFORMATION: methanol dehydrogenases

<400> SEQUENCE: 34

```
atgaaagctg ctgttgttaa cgaatttaaa aaagctctgg aaatcaaaga agttgaacgt      60
ccgaaactgg aagaaggtga agttctggtt aaaatcgaag cttgcggtgt ttgccacacc     120
gacctgcacg ctgctcacgg tgactggccg atcaaaccga actgccgct gatcccgggt      180 cacgaaggtg ttggtatcgt tgttgaagtt gctaaaggtg ttaaatctat caaagttggt     240
gaccgtgttg gtatcccgtg gctgtactct gcttgcggtg aatgcgaata ctgcctgacc     300
ggtcaggaaa ccctgtgccc gcaccagctg aacggtggtt actctgttga cggtggttac     360
gctgaatact gcaaagctcc ggctgactac gttgctaaaa tcccggacaa cctggacccg     420
gttgaagttg ctccgatcct gtgcgctggt gttaccacct acaaagctct gaaagtttct     480
ggtgctcgtc gggtgaatg ggttgctatc tacggtatcg gtggtctggg tcacatcgct      540
ctgcaatacg ctaaagctat gggtctgaac gttgttgctg ttgacatctc tgacgaaaaa     600
tctaaactgg ctaaagacct gggtgctgac atcgctatca acggtctgaa agaagacccg     660
gttaaagcta tccacgacca ggttggtggt gttcacgctg ctatctctgt tgctgttaac     720
aaaaaagctt cgaacaggc ttaccagtct gttaaacgtg gtggtaccct ggttgttgtt      780
ggtctgccga acgctgacct gccgatcccg atcttcgaca ccgttctgaa cggtgtttct     840
gttaaaggtt ctatcgttgg tacccgtaaa gacatgcagg aagctctgga cttcgctgct     900
cgtggtaaag ttcgtccgat agttgaaacc gctgaactgg aagaaatcaa cgaagttttc     960
gaacgtatgg aaaaaggtaa aatcaacggt cgtatcgttc tgaaactgaa agaagactaa    1020
```

<210> SEQ ID NO 35
<211> LENGTH: 390
<212> TYPE: PRT
<213> ORGANISM: Cupriavidus necator
<220> FEATURE:
<223> OTHER INFORMATION: methanol dehydrogenases

<400> SEQUENCE: 35

```
Met Thr His Leu Asn Ile Ala Asn Arg Val Asp Ser Phe Phe Ile Pro
1               5                10               15

Cys Val Thr Leu Phe Gly Pro Gly Cys Ala Arg Glu Thr Gly Ala Arg
                20               25               30

Ala Arg Ser Leu Gly Ala Arg Lys Ala Leu Ile Val Thr Asp Ala Gly
        35               40               45

Leu His Lys Met Gly Leu Ser Glu Val Val Ala Gly His Ile Arg Glu
    50               55               60

Ala Gly Leu Gln Ala Val Ile Phe Pro Gly Ala Glu Pro Asn Pro Thr
65               70               75               80
```

-continued

```
Asp Val Asn Val His Asp Gly Val Lys Leu Phe Glu Arg Glu Glu Cys
                85              90                  95

Asp Phe Ile Val Ser Leu Gly Gly Gly Ser Ser His Asp Cys Ala Lys
            100             105             110

Gly Ile Gly Leu Val Thr Ala Gly Gly Gly His Ile Arg Asp Tyr Glu
            115             120             125

Gly Ile Asp Lys Ser Thr Val Pro Met Thr Pro Leu Ile Ser Ile Asn
        130             135             140

Thr Thr Ala Gly Thr Ala Ala Glu Met Thr Arg Phe Cys Ile Ile Thr
145             150             155                 160

Asn Ser Ser Asn His Val Lys Met Ala Ile Val Asp Trp Arg Cys Thr
                165             170             175

Pro Leu Ile Ala Ile Asp Asp Pro Ser Leu Met Val Ala Met Pro Pro
            180             185             190

Ala Leu Thr Ala Ala Thr Gly Met Asp Ala Leu Thr His Ala Ile Glu
            195             200             205

Ala Tyr Val Ser Thr Ala Ala Thr Pro Ile Thr Asp Ala Cys Ala Glu
        210             215             220

Lys Ala Ile Val Leu Ile Ala Glu Trp Leu Pro Lys Ala Val Ala Asn
225             230             235                 240

Gly Asp Ser Met Glu Ala Arg Ala Ala Met Cys Tyr Ala Gln Tyr Leu
            245             250             255

Ala Gly Met Ala Phe Asn Asn Ala Ser Leu Gly Tyr Val His Ala Met
            260             265             270

Ala His Gln Leu Gly Gly Phe Tyr Asn Leu Pro His Gly Val Cys Asn
            275             280             285

Ala Ile Leu Leu Pro His Val Ser Glu Phe Asn Leu Ile Ala Ala Pro
        290             295             300

Glu Arg Tyr Ala Arg Ile Ala Glu Leu Leu Gly Glu Asn Ile Gly Gly
305             310             315                 320

Leu Ser Ala His Asp Ala Ala Lys Ala Ala Val Ser Ala Ile Arg Thr
            325             330             335

Leu Ser Thr Ser Ile Gly Ile Pro Ala Gly Leu Ala Gly Leu Gly Val
            340             345             350

Lys Ala Asp Asp His Glu Val Met Ala Ser Asn Ala Gln Lys Asp Ala
        355             360             365

Cys Met Leu Thr Asn Pro Arg Lys Ala Thr Leu Ala Gln Val Met Ala
        370             375             380

Ile Phe Ala Ala Ala Met
385             390
```

```
<210> SEQ ID NO 36
<211> LENGTH: 1173
<212> TYPE: DNA
<213> ORGANISM: Cupriavidus necator
<220> FEATURE:
<223> OTHER INFORMATION: methanol dehydrogenases

<400> SEQUENCE: 36
atgacccacc tgaacatcgc taatcgcgtc gacagcttct tcattccctg cgtgaccctc      60
ttcggtccgg gctgcgcgcg cgaaacgggc gctcgcgcca gatcactcgg ggccaggaag     120
gctctcatcg tcacggatgc aggcttgcac aagatggggc tctccgaagt cgtcgcgggg     180
cacattcgcg aagccgggct ccaggccgtc atctttccgg gtgccgagcc caatcccacc     240
gacgttaacg ttcacgacgg cgtcaagttg ttcgagcggg aagaatgcga cttcatcgtt     300
```

```
tcgctcggcg gcggctcatc gcacgactgc gcgaaaggca tcggcctcgt taccgccgga      360
ggcggacata tccgcgacta cgaaggcatc gacaaatcaa cggtgccaat gacgccgctg      420
atttcgatca acacgaccgc tggcactgct gcggaaatga cacgcttttg catcatcact      480
aattcgagca atcatgtgaa gatggcaatc gtcgactggc gttgcacgcc attaatcgcc      540
atcgacgatc cgagcctgat ggtcgcgatg ccgcccgcct tgacggcggc gaccggcatg      600
gacgcgttga ctcacgccat cgaggcatac gtttccaccg ccgccacgcc aattaccgat      660
gcctgtgcgg agaaggcgat cgtgctgatc gccgaatggc tgcccaaagc tgtcgcgaac      720
ggggactcga tggaagcacg cgcggccatg tgctacgccc aataccttgc cggcatggcc      780
ttcaacaacg catcactcgg ttacgtgcac gcgatggccc atcaactcgg cggcttctac      840
aatttgcccc acggcgtgtg caacgcgatc ctgctgccgc acgtgtcgga attcaacctc      900
attgccgcgc cggagcgcta cgcgagaatc gccgaactgc taggcgagaa cattgggggc      960
ttgagcgcgc atgacgccgc caaagctgcc gtctcggcga tccggacccct ttccacgtcg     1020 attggcattc cggcgggtct ggcgggcctg ggcgtcaagg cggacgacca tgaagtgatg     1080
gcaagcaatg cgcaaaagga tgcttgcatg ctgacgaatc cgcgcaaggc cacgctggcg     1140
caagtcatgg caatcttcgc tgcggcgatg taa                                 1173
```

<210> SEQ ID NO 37
<211> LENGTH: 345
<212> TYPE: PRT
<213> ORGANISM: Corynebacterium glutamicum
<220> FEATURE:
<223> OTHER INFORMATION: methanol dehydrogenases

<400> SEQUENCE: 37

```
Met Thr Thr Ala Ala Pro Gln Glu Phe Thr Ala Ala Val Val Glu Lys
1               5                   10                  15

Phe Gly His Glu Val Thr Val Lys Asp Ile Asp Leu Pro Lys Pro Gly
            20                  25                  30

Pro Asn Gln Ala Leu Val Lys Val Leu Thr Ser Gly Ile Cys His Thr
        35                  40                  45

Asp Leu His Ala Leu Glu Gly Asp Trp Pro Val Lys Pro Glu Pro Pro
    50                  55                  60

Phe Val Pro Gly His Glu Gly Val Gly Glu Val Val Glu Leu Gly Pro
65                  70                  75                  80

Gly Glu His Asp Val Lys Val Gly Asp Ile Val Gly Asn Ala Trp Leu
                85                  90                  95

Trp Ser Ala Cys Gly Thr Cys Glu Tyr Cys Ile Thr Gly Arg Glu Thr
            100                 105                 110

Gln Cys Asn Glu Ala Glu Tyr Gly Gly Tyr Thr Gln Asn Gly Ser Phe
            115                 120                 125

Gly Gln Tyr Met Leu Val Asp Thr Arg Tyr Ala Ala Arg Ile Pro Asp
        130                 135                 140

Gly Val Asp Tyr Leu Glu Ala Ala Pro Ile Leu Cys Ala Gly Val Thr
145                 150                 155                 160

Val Tyr Lys Ala Leu Lys Val Ser Glu Thr Arg Pro Gly Gln Phe Met
                165                 170                 175

Val Ile Ser Gly Val Gly Gly Leu Gly His Ile Ala Val Gln Tyr Ala
            180                 185                 190

Ala Ala Met Gly Met Arg Val Ile Ala Val Asp Ile Ala Asp Asp Lys
        195                 200                 205
```

-continued

Leu Glu Leu Ala Arg Lys His Gly Ala Glu Phe Thr Val Asn Ala Arg
        210             215             220

Asn Glu Asp Pro Gly Glu Ala Val Gln Lys Tyr Thr Asn Gly Gly Ala
225             230             235             240

His Gly Val Leu Val Thr Ala Val His Glu Ala Ala Phe Gly Gln Ala
            245             250             255

Leu Asp Met Ala Arg Arg Ala Gly Thr Ile Val Phe Asn Gly Leu Pro
        260             265             270

Pro Gly Glu Phe Pro Ala Ser Val Phe Asn Ile Val Phe Lys Gly Leu
        275             280             285

Thr Ile Arg Gly Ser Leu Val Gly Thr Arg Gln Asp Leu Ala Glu Ala
        290             295             300

Leu Asp Phe Phe Ala Arg Gly Leu Ile Lys Pro Thr Val Ser Glu Cys
305             310             315             320

Ser Leu Asp Glu Val Asn Asp Val Leu Asp Arg Met Arg Asn Gly Lys
        325             330             335

Ile Asp Gly Arg Val Ala Ile Arg Tyr
        340             345

<210> SEQ ID NO 38
<211> LENGTH: 1038
<212> TYPE: DNA
<213> ORGANISM: Corynebacterium glutamicum
<220> FEATURE:
<223> OTHER INFORMATION: methanol dehydrogenases

<400> SEQUENCE: 38
atgaccaccg ctgctccgca ggaatttacc gctgctgttg ttgaaaaatt cggtcacgaa      60
gttaccgtta aagacatcga cctgccgaaa ccgggtccga accaggctct ggttaaagtt     120
ctgacctctg gtatctgcca caccgacctg cacgctctgg aaggtgactg gccggttaaa     180
ccggaaccgc cgttcgttcc gggtcacgaa ggtgttggtg aagttgttga actgggtccg     240
ggtgaacacg acgttaaagt tggtgacatc gttggtaacg cttggctgtg gtctgcttgc     300
ggtacctgcg aatactgcat caccggtcgt gaaacccagt gcaacgaagc tgaatacggt     360
ggttacaccc agaacggttc tttcggtcag tacatgctgg ttgacacccg ttacgctgct     420
cgtatcccgg acggtgttga ctacctggaa gctgctccga tcctgtgcgc tggtgttacc     480
gtttacaaag ctctgaaagt ttctgaaacc cgtccgggtc agttcatggt tatctctggt     540
gttggtggtc tgggtcacat cgctgttcag tacgctgctg ctatgggtat gcgtgttatc     600
gctgttgaca tcgctgacga caaactggaa ctggctcgta acacggtgc tgaatttacc     660 gttaacgctc gtaacgaaga cccgggtgaa gctgttcaga atacaccaa cggtggtgct     720 cacggtgttc tggttaccgc tgttcacgaa gctgctttcg gtcaggctct ggacatggct     780
cgtcgtgctg gtaccatcgt tttcaacggt ctgccgccgg gtgaatttcc ggcttctgtt     840
ttcaacatcg tttttcaaagg tctgaccatc cgtggttctc tggttggtac ccgtcaggac     900
ctggctgaag ctctggactt cttcgctcgt ggtctgatca aaccgaccgt ttctgaatgc     960
tctctggacg aagttaacga cgttctggac cgtatgcgta acggtaaaat cgacggtcgt    1020
gttgctatcc gttactaa                                                  1038

<210> SEQ ID NO 39
<211> LENGTH: 385
<212> TYPE: PRT
<213> ORGANISM: Bacillus methanolicus

```
<220> FEATURE:
<223> OTHER INFORMATION: methanol dehydrogenases

<400> SEQUENCE: 39

Met Thr Asn Thr Gln Ser Ala Phe Phe Met Pro Ser Val Asn Leu Phe
1               5                   10                  15

Gly Ala Gly Ser Val Asn Glu Val Gly Thr Arg Leu Ala Asp Leu Gly
                20                  25                  30

Val Lys Lys Ala Leu Leu Val Thr Asp Ala Gly Leu His Gly Leu Gly
            35                  40                  45

Leu Ser Glu Lys Ile Ser Ser Ile Ile Arg Ala Ala Gly Val Glu Val
        50                  55                  60

Ser Ile Phe Pro Lys Ala Glu Pro Asn Pro Thr Asp Lys Asn Val Ala
65                  70                  75                  80

Glu Gly Leu Glu Ala Tyr Asn Ala Glu Asn Cys Asp Ser Ile Val Thr
                85                  90                  95

Leu Gly Gly Gly Ser Ser His Asp Ala Gly Lys Ala Ile Ala Leu Val
            100                 105                 110

Ala Ala Asn Gly Gly Lys Ile His Asp Tyr Glu Gly Val Asp Val Ser
        115                 120                 125

Lys Glu Pro Met Val Pro Leu Ile Ala Ile Asn Thr Thr Ala Gly Thr
    130                 135                 140

Gly Ser Glu Leu Thr Lys Phe Thr Ile Ile Thr Asp Thr Glu Arg Lys
145                 150                 155                 160

Val Lys Met Ala Ile Val Asp Lys His Val Thr Pro Thr Leu Ser Ile
            165                 170                 175

Asn Asp Pro Glu Leu Met Val Gly Met Pro Pro Ser Leu Thr Ala Ala
            180                 185                 190

Thr Gly Leu Asp Ala Leu Thr His Ala Ile Glu Ala Tyr Val Ser Thr
            195                 200                 205

Gly Ala Thr Pro Ile Thr Asp Ala Leu Ala Ile Gln Ala Ile Lys Ile
    210                 215                 220

Ile Ser Lys Tyr Leu Pro Arg Ala Val Ala Asn Gly Lys Asp Ile Glu
225                 230                 235                 240

Ala Arg Glu Gln Met Ala Phe Ala Gln Ser Leu Ala Gly Met Ala Phe
                245                 250                 255

Asn Asn Ala Gly Leu Gly Tyr Val His Ala Ile Ala His Gln Leu Gly
            260                 265                 270

Gly Phe Tyr Asn Phe Pro His Gly Val Cys Asn Ala Val Leu Leu Pro
        275                 280                 285

Tyr Val Cys Arg Phe Asn Leu Ile Ser Lys Val Glu Arg Tyr Ala Glu
    290                 295                 300

Ile Ala Ala Phe Leu Gly Glu Asn Val Asp Gly Leu Ser Thr Tyr Asp
305                 310                 315                 320

Ala Ala Glu Lys Ala Ile Lys Ala Ile Glu Arg Met Ala Lys Asp Leu
            325                 330                 335

Asn Ile Pro Lys Gly Phe Lys Glu Leu Gly Ala Lys Glu Glu Asp Ile
        340                 345                 350

Glu Thr Leu Ala Lys Asn Ala Met Lys Asp Ala Cys Ala Leu Thr Asn
        355                 360                 365

Pro Arg Lys Pro Lys Leu Glu Glu Val Ile Gln Ile Ile Lys Asn Ala
    370                 375                 380

Met
385
```

<210> SEQ ID NO 40
<211> LENGTH: 1158
<212> TYPE: DNA
<213> ORGANISM: Bacillus methanolicus
<220> FEATURE:
<223> OTHER INFORMATION: methanol dehydrogenases

<400> SEQUENCE: 40

```
atgaccaaca cccagtctgc tttcttcatg ccgtctgtta acctgttcgg tgctggttct      60
gttaacgaag ttggtacccg tctggctgac ctgggtgtta aaaaagctct gctggttacc     120
gacgctggtc tgcacggtct gggtctgtct gaaaaaatct cttctatcat ccgtgctgct     180
ggtgttgaag tttctatctt cccgaaagct gaaccgaacc cgaccgacaa aaacgttgct     240
gaaggtctgg aagcttacaa cgctgaaaac tgcgactcta tcgttaccct gggtggtggt     300
tcttctcacg acgctggtaa agctatcgct ctggttgctg ctaacggtgg taaaatccac     360
gactacgaag tgttgacgt ttctaaagaa ccgatggttc cgctgatcgc tatcaacacc     420
accgctggta ccggttctga actgaccaaa ttcaccatca tcaccgacac cgaacgtaaa     480
gttaaaatgg ctatcgttga caaacacgtt accccgaccc tgtctatcaa cgacccggaa     540
ctgatggttg gtatgccgcc gtctctgacc gctgctaccg gtctggacgc tctgacccac     600
gctatcgaag cttacgtttc taccggtgct accccgatca ccgacgctct ggctatccag     660
gctatcaaaa tcatctctaa atacctgccg cgtgctgttg ctaacggtaa agacatcgaa     720
gctcgtgaac agatggcttt cgctcagtct ctggctggta tggctttcaa caacgctggt     780
ctgggttacg ttcacgctat cgctcaccag ctgggtggtt ctacaactt cccgcacggt     840 gtttgcaacg ctgttctgct gccgtacgtt tgccgtttca acctgatctc taaagttgaa     900
cgttacgctg aaatcgctgc tttcctgggt gaaaacgttg acggtctgtc tacctacgac     960
gctgctgaaa aagctatcaa agctatcgaa cgtatggcta agacctgaa catcccgaaa    1020 ggtttcaaag aactgggtgc taagaagaa gacatcgaaa ccctggctaa aaacgctatg    1080
aaagacgctt cgctctgac caacccgcgt aaaccgaaac tggaagaagt tatccagatc    1140
atcaaaaacg ctatgtaa                                                 1158
```

<210> SEQ ID NO 41
<211> LENGTH: 385
<212> TYPE: PRT
<213> ORGANISM: Bacillus methanolicus
<220> FEATURE:
<223> OTHER INFORMATION: methanol dehydrogenases

<400> SEQUENCE: 41

```
Met Thr Asn Thr Leu Ser Ala Phe Phe Met Pro Ser Val Asn Leu Phe
1               5                   10                  15

Gly Ala Gly Ser Val Asn Glu Val Gly Thr Arg Leu Ala Asp Leu Gly
            20                  25                  30

Val Lys Lys Ala Leu Leu Val Thr Asp Ala Gly Leu His Gly Leu Gly
        35                  40                  45

Leu Ser Glu Lys Ile Ser Ser Ile Ile Arg Ala Ala Gly Val Glu Val
    50                  55                  60

Ser Ile Phe Pro Lys Ala Glu Pro Asn Pro Thr Asp Lys Asn Val Ala
65                  70                  75                  80

Glu Gly Leu Glu Ala Tyr Asn Ala Glu Asn Cys Asp Ser Ile Val Thr
                85                  90                  95
```

```
Leu Gly Gly Gly Ser Ser His Asp Ala Gly Lys Ala Ile Ala Leu Val
            100                 105                 110

Ala Ala Asn Gly Gly Lys Ile His Asp Tyr Glu Gly Val Asp Val Ser
            115                 120                 125

Lys Glu Pro Met Val Pro Leu Ile Ala Ile Asn Thr Thr Ala Gly Thr
    130                 135                 140

Gly Ser Glu Leu Thr Lys Phe Thr Ile Ile Thr Asp Thr Glu Arg Lys
145                 150                 155                 160

Val Lys Met Ala Ile Val Asp Lys His Val Thr Pro Thr Leu Ser Ile
                165                 170                 175

Asn Asp Pro Glu Leu Met Val Gly Met Pro Pro Ser Leu Thr Ala Ala
            180                 185                 190

Thr Gly Leu Asp Ala Leu Thr His Ala Ile Glu Ala Tyr Val Ser Thr
            195                 200                 205

Gly Ala Thr Pro Ile Thr Asp Ala Leu Ala Ile Gln Ala Ile Lys Ile
    210                 215                 220

Ile Ser Lys Tyr Leu Pro Arg Ala Val Ala Asn Gly Lys Asp Ile Glu
225                 230                 235                 240

Ala Arg Glu Gln Met Ala Phe Ala Gln Ser Leu Ala Gly Met Ala Phe
            245                 250                 255

Asn Asn Ala Gly Leu Gly Tyr Val His Ala Ile Ala His Gln Leu Gly
            260                 265                 270

Gly Phe Tyr Asn Phe Pro His Gly Val Cys Asn Ala Val Leu Leu Pro
            275                 280                 285

Tyr Val Cys Arg Phe Asn Leu Ile Ser Lys Val Glu Arg Tyr Ala Glu
    290                 295                 300

Ile Ala Ala Phe Leu Gly Glu Asn Val Asp Gly Leu Ser Thr Tyr Asp
305                 310                 315                 320

Ala Ala Glu Lys Ala Ile Lys Ala Ile Glu Arg Met Ala Lys Asp Leu
            325                 330                 335

Asn Ile Pro Lys Gly Phe Lys Glu Leu Gly Ala Lys Glu Glu Asp Ile
            340                 345                 350

Glu Thr Leu Ala Lys Asn Ala Met Lys Asp Leu Cys Ala Leu Thr Asn
            355                 360                 365

Pro Arg Lys Pro Lys Leu Glu Glu Val Ile Gln Ile Ile Lys Asn Ala
    370                 375                 380

Met
385
```

```
<210> SEQ ID NO 42
<211> LENGTH: 1158
<212> TYPE: DNA
<213> ORGANISM: Bacillus methanolicus
<220> FEATURE:
<223> OTHER INFORMATION: methanol dehydrogenases

<400> SEQUENCE: 42
atgaccaaca ccctgtctgc tttcttcatg ccgtctgtta acctgttcgg tgctggttct      60
gttaacgaag ttggtacccg tctggctgac ctgggtgtta aaaaagctct gctggttacc     120
gacgctggtc tgcacggtct gggtctgtct gaaaaaatct cttctatcat ccgtgctgct     180
ggtgttgaag tttctatctt cccgaaagct gaaccgaacc gaccgacaa aaacgttgct     240 gaaggtctgg aagcttacaa cgctgaaaac tgcgactcta tcgttaccct gggtggtggt     300
tcttctcacg acgctggtaa agctatcgct ctggttgctg ctaacggtgg taaaatccac     360
```

```
gactacgaag gtgttgacgt ttctaaagaa ccgatggttc cgctgatcgc tatcaacacc      420
accgctggta ccggttctga actgaccaaa ttcaccatca tcaccgacac cgaacgtaaa      480
gttaaaatgg ctatcgttga caaacacgtt accccgaccc tgtctatcaa cgacccggaa      540
ctgatggttg gtatgccgcc gtctctgacc gctgctaccg gtctggacgc tctgacccac      600
gctatcgaag cttacgtttc taccggtgct accccgatca ccgacgctct ggctatccag      660
gctatcaaaa tcatctctaa atacctgccg cgtgctgttg ctaacggtaa agacatcgaa      720
gctcgtgaac agatggcttt cgctcagtct ctggctggta tggctttcaa caacgctggt      780
ctgggttacg ttcacgctat cgctcaccag ctgggtggtt ctacaacttc cccgcacggt      840
gtttgcaacg ctgttctgct gccgtacgtt tgccgtttca acctgatctc taaagttgaa      900
cgttacgctg aaatcgctgc tttcctgggt gaaaacgttg acggtctgtc tacctacgac      960
gctgctgaaa aagctatcaa agctatcgaa cgtatggcta aagacctgaa catcccgaaa     1020
ggtttcaaag aactgggtgc taaagaagaa gacatcgaaa ccctggctaa aaacgctatg     1080
aaagacctgt gcgctctgac caacccgcgt aaaccgaaac tggaagaagt tatccagatc     1140
atcaaaaacg ctatgtaa                                                    1158
```

```
<210> SEQ ID NO 43
<211> LENGTH: 12
<212> TYPE: DNA
<213> ORGANISM: Artificial Sequence
<220> FEATURE:
<223> OTHER INFORMATION: RBS-A

<400> SEQUENCE: 43
aggaggtttg ga                                                            12

<210> SEQ ID NO 44
<211> LENGTH: 22
<212> TYPE: DNA
<213> ORGANISM: Artificial Sequence
<220> FEATURE:
<223> OTHER INFORMATION: RBS-B

<400> SEQUENCE: 44
aacaaaatga ggaggtactg ag                                                 22

<210> SEQ ID NO 45
<211> LENGTH: 16
<212> TYPE: DNA
<213> ORGANISM: Artificial Sequence
<220> FEATURE:
<223> OTHER INFORMATION: RBS-C

<400> SEQUENCE: 45
aagttaagag gcaaga                                                        16

<210> SEQ ID NO 46
<211> LENGTH: 14
<212> TYPE: DNA
<213> ORGANISM: Artificial Sequence
<220> FEATURE:
<223> OTHER INFORMATION: RBS-D

<400> SEQUENCE: 46
ttcgcagggg gaag                                                          14

<210> SEQ ID NO 47
<211> LENGTH: 18
```

```
<212> TYPE: DNA
<213> ORGANISM: Artificial Sequence
<220> FEATURE:
<223> OTHER INFORMATION: RBS-E

<400> SEQUENCE: 47
taagcaggac cggcggcg                                                          18

<210> SEQ ID NO 48
<211> LENGTH: 12
<212> TYPE: DNA
<213> ORGANISM: Artificial Sequence
<220> FEATURE:
<223> OTHER INFORMATION: RBS-F

<400> SEQUENCE: 48
caccatacac tg                                                               12

<210> SEQ ID NO 49
<211> LENGTH: 399
<212> TYPE: PRT
<213> ORGANISM: Pseudomonas putida
<220> FEATURE:
<223> OTHER INFORMATION: Formaldehyde dehydrogenases

<400> SEQUENCE: 49

Met Ser Gly Asn Arg Gly Val Val Tyr Leu Gly Ser Gly Lys Val Glu
1               5                   10                  15

Val Gln Lys Ile Asp Tyr Pro Lys Met Gln Asp Pro Arg Gly Lys Lys
            20                  25                  30

Ile Glu His Gly Val Ile Leu Lys Val Val Ser Thr Asn Ile Cys Gly
        35                  40                  45

Ser Asp Gln His Met Val Arg Gly Arg Thr Thr Ala Gln Val Gly Leu
    50                  55                  60

Val Leu Gly His Glu Ile Thr Gly Glu Val Ile Glu Lys Gly Arg Asp
65                  70                  75                  80

Val Glu Asn Leu Gln Ile Gly Asp Leu Val Ser Val Pro Phe Asn Val
                85                  90                  95

Ala Cys Gly Arg Cys Arg Ser Cys Lys Glu Met His Thr Gly Val Cys
            100                 105                 110

Leu Thr Val Asn Pro Ala Arg Ala Gly Gly Ala Tyr Gly Tyr Val Asp
        115                 120                 125

Met Gly Asp Trp Thr Gly Gly Gln Ala Glu Tyr Leu Leu Val Pro Tyr
    130                 135                 140

Ala Asp Phe Asn Leu Leu Lys Leu Pro Asp Arg Asp Lys Ala Met Glu
145                 150                 155                 160

Lys Ile Arg Asp Leu Thr Cys Leu Ser Asp Ile Leu Pro Thr Gly Tyr
                165                 170                 175

His Gly Ala Val Thr Ala Gly Val Gly Pro Gly Ser Thr Val Tyr Val
            180                 185                 190

Ala Gly Ala Gly Pro Val Gly Leu Ala Ala Ala Ala Ser Ala Arg Leu
        195                 200                 205

Leu Gly Ala Ala Val Val Ile Val Gly Asp Leu Asn Pro Ala Arg Leu
    210                 215                 220

Ala His Ala Lys Ala Gln Gly Phe Glu Ile Ala Asp Leu Ser Leu Asp
225                 230                 235                 240

Thr Pro Leu His Glu Gln Ile Ala Ala Leu Leu Gly Glu Pro Glu Val
                245                 250                 255
```

-continued

```
Asp Cys Ala Val Asp Ala Val Gly Phe Glu Ala Arg Gly His Gly His
             260                 265                 270

Glu Gly Ala Lys His Glu Ala Pro Ala Thr Val Leu Asn Ser Leu Met
         275                 280                 285

Gln Val Thr Arg Val Ala Gly Lys Ile Gly Ile Pro Gly Leu Tyr Val
     290                 295                 300

Thr Glu Asp Pro Gly Ala Val Asp Ala Ala Ala Lys Ile Gly Ser Leu
305                 310                 315                 320

Ser Ile Arg Phe Gly Leu Gly Trp Ala Lys Ser His Ser Phe His Thr
             325                 330                 335

Gly Gln Thr Pro Val Met Lys Tyr Asn Arg Ala Leu Met Gln Ala Ile
             340                 345                 350

Met Trp Asp Arg Ile Asn Ile Ala Glu Val Val Gly Val Gln Val Ile
         355                 360                 365

Ser Leu Asp Asp Ala Pro Arg Gly Tyr Gly Glu Phe Asp Ala Gly Val
     370                 375                 380

Pro Lys Lys Phe Val Ile Asp Pro His Lys Thr Phe Ser Ala Ala
385                 390                 395
```

```
<210> SEQ ID NO 50
<211> LENGTH: 1200
<212> TYPE: DNA
<213> ORGANISM: Pseudomonas putida
<220> FEATURE:
<223> OTHER INFORMATION: Formaldehyde dehydrogenases

<400> SEQUENCE: 50
atgtctggta accgtggtgt tgtttacctg ggttctggta agttgaagt  tcagaaaatc      60 gactacccga aaatgcagga cccgcgtggt aaaaaaatcg aacacggtgt  tatcctgaaa     120
gttgtttcta ccaacatctg cggttctgac cagcacatgt tcgtggtcg  taccaccgct     180 caggttggtc tggttctggg tcacgaaatc accggtgaag ttatcgaaaa  aggtcgtgac     240
gttgaaaacc tgcaaatcgg tgacctggtt tctgttccgt tcaacgttgc  ttgcggtcgt     300
tgccgttctt gcaaagaaat gcacaccggt gtttgcctga ccgttaaccc  ggctcgtgct     360
ggtggtgctt acggttacgt tgacatgggg gactggaccg tggtcaggc  tgaatacctg     420 ctggttccgt acgctgactt caacctgctg aaactgccgg accgtgacaa  agctatggaa     480
aaaatccgtg acctgacctg cctgtctgac atcctgccga ccggttacca  cggtgctgtt     540
accgctggtg ttggtccggg ttctaccgtt tacgttgctg gtgctggtcc  ggttggtctg     600
gctgctgctg cttctgctcg tctgctgggt gctgctgttg ttatcgttgg  tgacctgaac     660
ccggctcgtc tggctcacgc taaagctcag ggtttcgaaa tcgctgacct  gtctctggac     720
accccgctgc acgaacagat cgctgctctg ctgggtgaac cggaagttga  ctgcgctgtt     780
gacgctgttg gtttcgaagc tcgtggtcac ggtcacgaag gtgctaaaca  cgaagctccg     840
gctaccgttc tgaactctct gatgcaggtt accgtgttg  ctggtaaaat  cggtatcccg     900
ggtctgtacg ttaccgaaga cccgggtgct gttgacgctg ctgctaaaat  cggttctctg     960
tctatccgtt tcggtctggg ttgggctaaa tctcactctt ccacaccgg  tcagaccccg    1020 gttatgaaat acaaccgtgc tctgatgcag gctatcatgt gggaccgtat  caacatcgct    1080
gaagttgttg gtgttcaggt tatctctctg gacgacgctc cgcgtggtta  cggtgaattt    1140
gacgctggtg ttccgaaaaa attcgttatc gacccgcaca aaaccttctc  tgctgcttaa    1200
```

```
<210> SEQ ID NO 51
```

```
<211> LENGTH: 399
<212> TYPE: PRT
<213> ORGANISM: Pseudomonas aeruginosa
<220> FEATURE:
<223> OTHER INFORMATION: Formaldehyde dehydrogenases

<400> SEQUENCE: 51

Met Ser Gly Asn Arg Gly Val Val Tyr Leu Gly Pro Gly Lys Val Glu
1               5                   10                  15

Val Gln Asn Ile Pro Tyr Pro Lys Met Gln Asp Pro Gln Gly Arg Gln
            20                  25                  30

Ile Asp His Gly Val Ile Leu Arg Val Val Ser Thr Asn Ile Cys Gly
        35                  40                  45

Ser Asp Gln His Met Val Arg Gly Arg Thr Thr Ala Pro Glu Gly Leu
    50                  55                  60

Val Leu Gly His Glu Ile Thr Gly Glu Val Val Glu Ile Gly Arg Gly
65                  70                  75                  80

Val Glu Thr Met Lys Ile Gly Asp Leu Val Ser Val Pro Phe Asn Val
                85                  90                  95

Ala Cys Gly His Cys Arg Thr Cys Lys Glu Gln His Thr Gly Val Cys
            100                 105                 110

Leu Thr Val Asn Pro Ala Arg Ala Gly Gly Ala Tyr Gly Tyr Val Asp
            115                 120                 125

Met Gly Gly Trp Val Gly Gly Gln Ala Glu Tyr Val Leu Val Pro Tyr
        130                 135                 140

Ala Asp Phe Asn Leu Leu Lys Leu Pro Asn Arg Glu Ala Ala Met Glu
145                 150                 155                 160

Lys Ile Arg Asp Leu Thr Cys Leu Ser Asp Ile Leu Pro Thr Gly Tyr
                165                 170                 175

His Gly Ala Val Thr Ala Gly Val Gly Pro Gly Ser Thr Val Tyr Ile
            180                 185                 190

Ala Gly Ala Gly Pro Val Gly Leu Ala Ala Ala Ala Ser Ala Arg Leu
            195                 200                 205

Leu Gly Ala Ala Val Val Ile Val Gly Asp Val Asn Pro Thr Arg Leu
    210                 215                 220

Ala His Ala Lys Lys Gln Gly Phe Glu Ile Ala Asp Leu Ser Lys Asp
225                 230                 235                 240

Thr Pro Leu His Glu Gln Ile Ala Ala Leu Leu Gly Glu Pro Glu Val
                245                 250                 255

Asp Cys Ala Val Asp Ala Val Gly Phe Glu Ala Arg Gly His Gly His
            260                 265                 270

Ser Gly Ser Gln Gln Glu Ala Pro Ala Thr Val Leu Asn Ser Leu Met
    275                 280                 285

Gly Ile Thr Arg Val Ala Gly Lys Ile Gly Ile Pro Gly Leu Tyr Val
    290                 295                 300

Thr Glu Asp Pro Gly Ala Val Asp Ala Ala Ala Lys His Gly Ala Leu
305                 310                 315                 320

Ser Ile Arg Phe Gly Leu Gly Trp Ala Lys Ser His Ser Phe His Thr
                325                 330                 335

Gly Gln Thr Pro Val Met Lys Tyr Asn Arg Gln Leu Met Gln Ala Ile
            340                 345                 350

Met Trp Asp Arg Ile Lys Ile Ala Asp Ile Val Gly Val Glu Val Ile
        355                 360                 365

Thr Leu Asp Asp Ala Pro Lys Gly Tyr Gly Glu Phe Asp Ala Gly Val
    370                 375                 380
```

```
Pro Lys Lys Phe Val Ile Asp Pro His Asn Leu Phe Arg Ala Ala
385               390                395

<210> SEQ ID NO 52
<211> LENGTH: 1200
<212> TYPE: DNA
<213> ORGANISM: Pseudomonas aeruginosa
<220> FEATURE:
<223> OTHER INFORMATION: Formaldehyde dehydrogenases

<400> SEQUENCE: 52
atgtctggca atcgtggtgt ggtctatctc ggcccgggca aggtcgaggt gcagaacatt      60
ccctatccga agatgcagga cccgcagggc cggcagatcg accacggggt gatcctgcgg     120
gtggtctcca ccaacatctg cggctccgac cagcacatgg tgcgcggccg caccaccgcg     180
ccggaaggcc tggtgctggg ccacgagatc accggcgagg tggtggagat cgggcgtggc     240
gtggaaacca tgaagatcgg cgacctggtc tcggtaccgt tcaacgtcgc ctgcggccac     300
tgccgtacct gcaaggaaca gcacaccggc gtctgcctga cggtcaatcc ggcgcgtgcc     360
ggcggcgcct acggctacgt cgacatgggt ggctgggtcg gcggccaggc cgaatacgtg     420
ctggtgccct acgccgactt caacctgctg aaactgccca accgcgaagc ggcgatggag     480
aagatccgcg acctgacctg cctttcggac atcctcccca ccggctacca cggcgcggtc     540
accgccggcg tcggcccggg cagcacggtc tacatcgccg cgccggtcc ggtcggcctg      600 gccgcggcgg cctcggcacg cctgctcggc gcggcggtgg tgatcgtcgg cgacgtcaac     660
ccgacccgcc tggcccacgc caagaaacag ggcttcgaga tcgccgacct gtccaaggac     720
accccgctgc acgaacagat cgccgctctg ctgggcgagc cggaggtcga ctgcgcggtc     780
gatgcggtcg gtttcgaggc gcgcggccac ggccattcgg gctcgcagca ggaagccccg     840
gccaccgtgc tcaactcgct gatgggcatc acccgggtcg ccggcaagat cggcattccc     900
ggcctgtacg tcaccgaaga cccgggcgca gtggacgcgg ccgccaagca cggcgccctg     960
agcatccgct tcggcctggg ctgggccaag tcgcacagct tccataccgg ccagaccccg    1020
gtgatgaagt acaaccgcca gctgatgcag gcgatcatgt gggaccggat caagatcgcc    1080
gacatcgtcg gggtggaagt catcaccctc gacgatgcgc cgaaaggcta tggcgagttc    1140
gacgccgggg tgccgaagaa attcgtcatc gacccacaca acctgttccg cgcggcctga    1200

<210> SEQ ID NO 53
<211> LENGTH: 84
<212> TYPE: DNA
<213> ORGANISM: Artificial Sequence
<220> FEATURE:
<223> OTHER INFORMATION: pntAB_MAGE

<400> SEQUENCE: 53
ttggcgctag atcacaggca taattttcag tacgttatag ggtgtttgtt actaatttat      60
tttaacggag taacatttag ctcg                                             84

<210> SEQ ID NO 54
<211> LENGTH: 84
<212> TYPE: DNA
<213> ORGANISM: Artificial Sequence
<220> FEATURE:
<223> OTHER INFORMATION: fdh_MAGE

<400> SEQUENCE: 54
agttaaacaa aattatttct attaactagt gaattcggtc attgcgtcct gcgcatatta      60
```

-continued

```
tatgtgaatc acagtgatat gtca                                              84

<210> SEQ ID NO 55
<211> LENGTH: 20
<212> TYPE: DNA
<213> ORGANISM: Artificial Sequence
<220> FEATURE:
<223> OTHER INFORMATION: pntA_forward

<400> SEQUENCE: 55
gccaatctgc aacagtgctc                                                   20

<210> SEQ ID NO 56
<211> LENGTH: 20
<212> TYPE: DNA
<213> ORGANISM: Artificial Sequence
<220> FEATURE:
<223> OTHER INFORMATION: pntA reverse

<400> SEQUENCE: 56
tttttggctg gatggcaagc                                                   20

<210> SEQ ID NO 57
<211> LENGTH: 21
<212> TYPE: DNA
<213> ORGANISM: Artificial Sequence
<220> FEATURE:
<223> OTHER INFORMATION: fdh forward

<400> SEQUENCE: 57
cgtgacgaat acctgatcgt t                                                 21

<210> SEQ ID NO 58
<211> LENGTH: 27
<212> TYPE: DNA
<213> ORGANISM: Artificial Sequence
<220> FEATURE:
<223> OTHER INFORMATION: fdh reverse

<400> SEQUENCE: 58
ggtagcgtta cctttagagt aagagtg                                           27

<210> SEQ ID NO 59
<211> LENGTH: 474
<212> TYPE: PRT
<213> ORGANISM: Escherichia coli
<220> FEATURE:
<223> OTHER INFORMATION: lipoamide dehydrogenase

<400> SEQUENCE: 59

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95
```

```
Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
            115                 120                 125

Gly Glu Asn Gly Lys Thr Val Ile Asn Phe Asp Asn Ala Ile Ile Ala
            130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
            195                 200                 205

Gln Val Ile Pro Ala Ala Asp Lys Asp Ile Val Lys Val Phe Thr Lys
            210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
            275                 280                 285

Val Asp Asp Arg Gly Phe Ile Arg Val Asp Lys Gln Leu Arg Thr Asn
            290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
            355                 360                 365

Glu Lys Gly Ile Ser Tyr Glu Thr Ala Thr Phe Pro Trp Ala Ala Ser
            370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
            435                 440                 445

His Glu Ser Val Gly Leu Ala Ala Glu Val Phe Glu Gly Ser Ile Thr
            450                 455                 460

Asp Leu Pro Asn Pro Lys Ala Lys Lys Lys
465                 470
```

<210> SEQ ID NO 60
<211> LENGTH: 1425
<212> TYPE: DNA
<213> ORGANISM: Escherichia coli
<220> FEATURE:
<223> OTHER INFORMATION: lipoamide dehydrogenase

```
<400> SEQUENCE: 60
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta aagcactgct gcacgtagca     180
aaagttatcg aagaagccaa agcgctggct gaacacggta tcgtcttcgg cgaaccgaaa     240
accgatatcg acaagattcg tacctggaaa gagaaagtga tcaatcagct gaccggtggt     300
ctggctggta tggcgaaagg ccgcaaagtc aaagtggtca acggtctggg taaattcacc     360
ggggctaaca ccctggaagt tgaaggtgag aacggcaaaa ccgtgatcaa cttcgacaac     420
gcgatcattg cagcgggttc tcgcccgatc caactgccgt ttattccgca tgaagatccg     480
cgtatctggg actccactga cgcgctggaa ctgaaagaag taccagaacg cctgctggta     540
atgggtggcg gtatcatcgg tctggaaatg ggcaccgttt accacgcgct gggttcacag     600
attgacgtgg ttgaaatgtt cgaccaggtt atcccggcag ctgacaaaga catcgttaaa     660
gtcttcacca agcgtatcag caagaaattc aacctgatgc tggaaaccaa agttaccgcc     720
gttgaagcga aagaagacgg catttatgtg acgatggaag gcaaaaaagc acccgctgaa     780
ccgcagcgtt acgacgccgt gctggtagcg attggtcgtg tgccgaacgg taaaaacctc     840
gacgcaggca aagcaggcgt ggaagttgac gaccgtggtt tcatccgcgt tgacaaacag     900
ctgcgtacca acgtaccgca tctctttgct atcggcgata tcgtcggtca accgatgctg     960
gcacacaaag gtgttcacga aggtcacgtt gccgctgaag ttatcgccgg taagaaacac    1020
tacttcgatc cgaaagttat cccgtccatc gcctataccg aaccagaagt tgcatgggtg    1080
ggtctgactg agaagaagc gaaagagaaa ggcatcagct atgaaaccgc caccttcccg    1140
tgggctgctt ctggtcgtgc tatcgcttcc gactgcgcag acggtatgac caagctgatt    1200
ttcgacaaag aatctcaccg tgtgatcggt ggtgcgattg tcggtactaa cggcggcgag    1260
ctgctgggtg aaatcggcct ggcaatcgaa atgggttgtg atgctgaaga catcgcactg    1320
accatccacg cgcacccgac tctgcacgag tctgtgggcc tggcggcaga agtgttcgaa    1380
ggtagcatta ccgacctgcc gaacccgaaa gcgaagaaga agtaa                    1425

<210> SEQ ID NO 61
<211> LENGTH: 79
<212> TYPE: DNA
<213> ORGANISM: Artificial Sequence
<220> FEATURE:
<223> OTHER INFORMATION: Mutation in the 5'UTR of FDH

<400> SEQUENCE: 61
atatgcgcag gacgcactga ccgaattcac tagttaatag aaataatttt gtttaacttt      60
aaggaggttt ggaatgcat                                                    79

<210> SEQ ID NO 62
<211> LENGTH: 78
<212> TYPE: DNA
<213> ORGANISM: Artificial Sequence
<220> FEATURE:
<223> OTHER INFORMATION: Mutation in the promoter of pntAB

<400> SEQUENCE: 62
tagggcgttt gttactaatt tattttaacg gagtaacatt tagctcgtac atgagcagct      60
atgcgaattg gcatacca                                                    78
```